(12) United States Patent
Prickett et al.

(10) Patent No.: US 7,691,963 B2
(45) Date of Patent: *Apr. 6, 2010

(54) EXENDINS AND EXENDIN AGONISTS MODIFIED WITH POLYAMINO ACIDS

(75) Inventors: Kathryn S. Prickett, San Diego, CA (US); Andrew A. Young, Rancho Santa Fe, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 12/101,818

(22) Filed: Apr. 11, 2008

(65) Prior Publication Data

US 2008/0200390 A1 Aug. 21, 2008

Related U.S. Application Data

(63) Continuation of application No. 12/046,038, filed on Mar. 11, 2008, which is a continuation of application No. 11/174,089, filed on Jun. 30, 2005, which is a continuation of application No. 09/561,226, filed on Apr. 28, 2000, now Pat. No. 6,924,264.

(60) Provisional application No. 60/132,018, filed on Apr. 30, 1999.

(51) Int. Cl.
- *A61K 38/28* (2006.01)
- *A61K 38/22* (2006.01)
- *A61K 38/00* (2006.01)

(52) U.S. Cl. ............ 530/308; 424/185.1; 424/278.1; 435/69.7; 530/300; 530/303; 530/322; 530/324; 514/2; 514/3; 514/23

(58) Field of Classification Search ................ None
See application file for complete search history.

(56) References Cited

U.S. PATENT DOCUMENTS

| | | | |
|---|---|---|---|
| 4,179,337 A | 12/1979 | Davis | |
| 4,766,106 A | 8/1988 | Katre | |
| 5,122,614 A | 6/1992 | Zalipsky | |
| 5,214,131 A | 5/1993 | Sano et al. | |
| 5,264,372 A | 11/1993 | Beaumont | |
| 5,424,286 A | 6/1995 | Eng | |
| 5,686,511 A | 11/1997 | Bobo | |
| 5,747,639 A | 5/1998 | Seeley | |
| 5,824,784 A | 10/1998 | Kinstler | |
| 5,839,443 A | 11/1998 | Rose et al. | |
| 6,051,557 A | 4/2000 | Drucker et al. | |
| 6,268,343 B1 | 7/2001 | Knudsen et al. | |
| 6,284,725 B1 | 9/2001 | Coolidge et al. | |
| 6,376,549 B1 | 4/2002 | Fine et al. | |
| 6,429,197 B1 | 8/2002 | Coolidge et al. | |
| 6,451,974 B1 | 9/2002 | Hansen | |
| 6,528,486 B1 | 3/2003 | Larsen et al. | |
| 6,723,530 B1 * | 4/2004 | Drucker ............ | 435/69.1 |
| 6,753,165 B1 | 6/2004 | Cox et al. | |
| 6,767,887 B1 | 7/2004 | Hoffmann et al. | |
| 6,872,700 B1 | 3/2005 | Young et al. | |
| 6,924,264 B1 | 8/2005 | Prickett et al. | |
| 6,956,026 B2 | 10/2005 | Beeley et al. | |
| 6,982,248 B2 | 1/2006 | Coolidge et al. | |
| 7,153,825 B2 | 12/2006 | Young et al. | |
| 7,157,555 B1 * | 1/2007 | Beeley et al. ............ | 530/324 |
| 7,189,690 B2 | 3/2007 | Rosen et al. | |
| 7,226,990 B2 | 6/2007 | Knudsen et al. | |
| 7,259,136 B2 | 8/2007 | Hathaway et al. | |
| 7,271,149 B2 | 9/2007 | Glaesner et al. | |
| 7,329,646 B2 * | 2/2008 | Sun et al. ............ | 514/12 |
| 2001/0047084 A1 | 11/2001 | Knudsen et al. | |
| 2002/0147131 A1 | 10/2002 | Coolidge et al. | |
| 2005/0026834 A1 | 2/2005 | Cox et al. | |
| 2005/0215475 A1 * | 9/2005 | Ong et al. ............ | 514/12 |
| 2006/0030528 A1 | 2/2006 | Hathaway et al. | |
| 2007/0037750 A1 | 2/2007 | Young et al. | |

FOREIGN PATENT DOCUMENTS

| | | |
|---|---|---|
| EP | 0619322 A2 | 10/1994 |
| WO | WO 95/70989 | 3/1995 |
| WO | WO 97/46584 | 12/1997 |

(Continued)

OTHER PUBLICATIONS

Crowe et al. (1994) 6xHis-Ni-NTA chromatography as a superior technique in recombinant protein expression/purification, Methods Mol. Biol., vol. 31, pp. 371-387.*

(Continued)

*Primary Examiner*—Andrew Wang
*Assistant Examiner*—Samuel W Liu
(74) *Attorney, Agent, or Firm*—Connolly Bove Lodge & Hutz LLP

(57) ABSTRACT

Modified exendins and exendin agonists having an exendin or exendin agonist linked to one or more molecular weight increasing compounds, for example, polyamino acids, polyethylene glycol polymers, and related formulations and dosages and methods of administration thereof are provided. These modified exendins and exendin agonists, compositions comprising the modified exendin or the agonist thereof are useful in treating diabetes and conditions that would be benefited by lowering plasma glucose or delaying and/or slowing gastric emptying or inhibiting food intake.

20 Claims, 20 Drawing Sheets

FOREIGN PATENT DOCUMENTS

| WO | WO 98/05351 | 2/1998 |
|---|---|---|
| WO | WO 98/08871 | 3/1998 |
| WO | WO 98/30231 | 7/1998 |
| WO | WO 99/07404 | 2/1999 |
| WO | WO 99/25727 | 5/1999 |
| WO | WO 99/25728 | 5/1999 |
| WO | WO 9925727 A2 * | 5/1999 |
| WO | WO 99/43708 | 9/1999 |
| WO | WO 99/46283 | 9/1999 |
| WO | WO 00/41548 | 7/2000 |
| WO | WO 00/66629 | 11/2000 |

OTHER PUBLICATIONS

Nordström et al. (1999) Generation of a new protein purification matrix by loading ceramic hydroxyapatite with metal ions—demonstration with poly-histidine tagged green fluorescent protein, J. Biotechnol., vol. 69, No. 2-3, pp. 125-133.*

O'Hagen; "Recent Advances in Vaccine Adjuvants for Systemic and Mucosal Administration"; J Pharma Pharmacol; vol. 49:pp. 1-10; (Sep. 1997).

Patentee Response to First Office Action issued by the United States Patent Office dated Jan. 17, 2008 for Inter Partes Reexamination of US Patent No. 6,924,264 ; (Apr. 2008).

Poznansky; "In Vitro and In Vivo Activity of Soluble Cross-Linked Uricase-Albumin Polymers: A Model for Enzyme Therapy"; Life Sciences; vol. 24:pp. 153-158; (1979).

Remy, et al.; "Immunogenicity and Antigenicity of Soluble Cross-Linked Ensyme/Albumin Polymers: Advantages for Enzyme Therapy"; The Lancet; vol. 2:pp. 68-70 (Jul. 1978).

Ruiz-Grande, et al.; Renal Catabolism of Human Glucagon-like Peptides 1 and 2; Can. J. Physiol. Pharmacol.; vol. 68; pp. 1568-1573 (1990).

Reexamination No. 95/000,276; Inter Partes Reexamination of US Patent No. 6,924,264; Second Declaration of Quraishi (May 15, 2008).

Shi, et al.; "Chronic Caffeine Alters the Density of Adenosine, Adrenergic, Cholinergic, GABA, and Serotonin Receptors and Calciuym Channels in Mouse Brain"; Cellular and Molecular Neurobiology; vol. 13, No. 3:pp. 247-261 (1993).

Reexamination No. 95/000,276; Inter Partes Reexamination of US Patent No. 6,924,264; Third Declaration of Poznansky (May 15, 2008).

Reexamination No. 95/000,276; Inter Partes Reexamination of US Patent No. 6,924,264; Third Party Requestor's Comments (May 15, 2008).

Wang, et al.; "Parenteral Formulation of Proteins and Peptides: Stability and Stabilizers" J. Paren. Sci. Tech., vol. 42:pp. S3-S26 (1988).

Wang et al.; Polythyfene Glycol-modified Chimeric TOxin Composed of Transforming Growth Factor and Psuedomonas Exotoxin; Cancer Res., vol. 53:pp. 4588-4594 (Dec. 1993).

Zimmerman et al.; "Schedule Dependency of hte Antitumor Activity and Toxicity of Polythylene Glycol-modified Interleukin 2 in Murine Tumor Models"; Cancer Res., 49:6521-6528 (Dec. 1989).

Capasso et al., J. Neuroedocrinology 220(Suppl. 1):39-46 (2008) "Gastrointestinal Regulation of Food Intake: General Aspects and Focus on Anandamide and Oleoylethyanolamide".

Raybould et al., Am. J. Physiol. 274:R1834-R1838 (1998) "Inhibition of gastric emptying in response to intestinal lipid is dependent on chylomicron formation".

Gaspar et al., Human Mol. Genet. 9(13):1957-1966 (2000) "CAG tract of MJD-1 may be prone to frameshifts causing polyalanine accumulation".

e-Medicine (2008, dated)—http://www.emedicine.com/MED/topic589.htm#section AuthorsandEditors, pp. 1 and 3 "Dumping Syndrome".

WD (2008,updated): http://www.wrongdiagnosis.com/igt.intro.htm, p. 1 "Impaired glucose tolorance".

Gin et al., Diabetes Metabol. 26(4):2265-272 (2000) "Post-prandial hyperglycemia. Post-prandial hyperglycemia and diabetes".

Merck Manual Professional (2008, updated): http://www.merck.com/mmpe/sec12/ch159/ch159b.htlm, pp. 1-2: "Dyslipidemia".

Devlin et al., Aj. J. Psychiatry 157(6):854-866 (2000) "Obesity: what mental health professionals need to know".

Chen et al, Diabetes, vol. 48, Supplement 1, Abstract No. 1884 (May 1999).

European Patent Application No. 00 928 685: Declaration of Andrew Young filed by Applicants in Proceedings for European Patent Application No. 00 928 685 (Jun. 6, 2008).

European Patent Application No. 00 928 685: European Patent Office Decision to Refuse European Patent Application (Jul. 16, 2008).

European Patent Application No. 00 928 685: Third Party Observations filed in European Patent Application No. 00 928 685 (Apr. 8, 2008).

Abuchowski, et al.; "Effect of Covalent Attachment of Polyethylene Glycol on Immunogenicity and Circulating Life of Bovine Liver Catalase"; Journal of Biological Chemistry; vol. 252; Issue 11;3582-3588 (Jun. 1977).

Chen, et al.; Diabetes, vol. 1, Supp.1: A426, Abstract No. 1884 (May 1999).

Declaration of Andrew Young attached to Request for Inter Partes Reexamination of US Patent No. 6,924,264 (Apr. 16, 2008).

Declaration of John Herich attached to Request for Inter Partes Reexamination of US Patent No. 6,924,264 (Apr. 15, 2008).

England, et al.; "Determination of the Packed Cell Volume Using I-Human Serum Albumin"; British Journal of Hermatology, vol. 30; pp. 365-370 (Dec. 1974).

Gennaro et al, Remington: The Science and Practice of Pharmacy, 19th Ed., Mack Printing Company, Easton, PA, pp. 1457, 1461, 1526, 1550 (1995).

Giberman; "Determination of the Trapped Volume in a Pellet of Red Blood Cells"; Section of Biological Ultrastructure, The Weismann Institute of Science, Rehovot (Israel); Experientia, 29: pp. 1083-1085; (Feb. 1973).

Gould; "Diabetes Mellitus in Cattle"; Veterinary Record; vol. 109; pp. 539 (Dec. 1981).

Harlow & Lane, Antibodies: A Laboratory Manual, Cold Spring Harbor Laboratory, Cold Spring Harbor, New York, pp. 53-137 (1988).

Maack, et al.; "Renal Fllatration, Transport, and Metabolism of Low-Molecular-Weight Proteins: A Review"; Kidney International; vol. 16; pp. 251-270 (Mar. 1979).

Alberts et al, Molecular Biology of the Cell, Third Edition, New York: Garland Publishing, p. G19 (1994).

Amylin Pharmaceuticals, Inc., Form 10-Q filed Aug. 7, 2007.

Amylin Pharmaceuticals, Inc., Form 10-Q filed Nov. 6, 2007.

Barragan et al, Regulatory Peptides, 67:63-68 (1996).

Binder et al, Diabetes Care, 7:188-199 (1984).

Breton et al, Eur. J. Biochem., 231:563-569 (1995).

Broca et al., "Hydroxyisoleucine: Experimental evidence of its insulinotropic and antidiabetic properties," Am. J. Physiol. 277:617 (1999).

Byrne et al., "Lessons from human studies with glucagon-like peptide-1: Potential of the gut hormone for clinical use," in: Insulintropic Gut Hormone Glucagon-Like Peptide 1, Fehmann, HC Editor, Basel, Switzerland: Karger, pp. 219-233 (1997).

Byetta Prescribing Information, (Oct. 2007).

Catalog, Shearwater Polymers, Inc., Functionalized Biocompatible Polymers for Research, Polyethylene Glycol Derivatives, 1993.

Chen et al., "Tissue-specific Expression of Unique mRNAs that Encode Proglucagon-derived Peptides or Exendin 4 in the Lizard," J. Biol. Chem. 272(7):4108-4115 (1997).

Chicchi et al. (1997) Fluorescein-Trp25S-exendin-4, a biologically active fluorescent probe for the human GLP-1 receptor. Peptides, vol. 18, pp. 319-321.

Cooper, The Cell: A Molecular Approach, ASM Press (Washington, DC), Sinauer Associates, Inc. (Sunderland, MA), pp. 296-298, 648 (1997).

Creutzfeldt et al., "Glucagonstatic Actions and Reduction of Fasting Hyperglycemia by Exogenous Glucagon-Like Peptide 1(7-36) Amide in Type I Diabetic Patients," Diabetes Care 19(6):580-586 (1996).

D'Alessio et al., "Elimination of the Action of Glucagon-Like Peptide 1 Causes an Impairment of Glucose Tolerance After Nutrient Ingestion by Healthy Baboons," J. Clin. Invest. 97:133-38 (1996).

Davis et al, Peptide and Protein and Drug Delivery, Marcel Dekker, Inc., New York, pp. 831-864 (1991).

Delgado et al., "The Uses and Properties of PEG-Linked Proteins," Critical Reviews in Therapeutic Drug Carrier Systems 9(3,4):249-304 (1992).

Drucker, Diabetes, 47:159-169 (1998).

Edwards et al, Diabetes, 48:86-93 (1998).

Edwards et al., Glucagon-Like Peptide 1 Has a Physiological Rote in the Control of postprandial Glucose in Humans—Studies with the Antagonist Exendin 9-39, Diabetes 48:86-93 (1999).

Egan et al., "Glucagon-Like Peptide-1 Restores Acute Phase Insulin Release to Aged Rats," Diabetologia 40(Supp 1):A130 (1997).

Eissele et al., "Rat Gastric Somatostatin and Gastrin Release: Interactions of Exendin-4 and Truncated Glucagon-Like Peptide-1 (GLP-1) Amide," Life Sci., 55:629-34 (1994).

Eng et al., "Isolation and Characterization of Exendin-4, an Exendin-3 Analogue, from Heloderma suspectum Venom," J. Biol. Chem. 267:7402-05 (1992).

Eng et al., "Purification and Structure of Exendin-3 a New Pancreatic Secretagogue Isolated from Heloderma horridum Venom," J. Biol. Chem. 265:20259-62 (1990).

Eng., "Prolonged Effect of Exendin-4 on Hyperglycemia of db/db mice," Diabetes 45(Supp 2):152A (abstract 554) (1996).

Francis et al., "PEGylation of cytokines and other Therapeutic Proteins and Peptides: The Importance of Biological Optimisation of Coupling Techniques," Intl J. Hematololgy 68:1-18 (1998).

Gennaro, Ed., Remington: The Science and Practice of Pharmacy, 19th Edition, pp. 898, 931-994 (1995).

Goke et al, J. Mol. Endocrinol., 2:93-98 (1989).

Goke etal, FEBS Lett., 300:232-236 (1992).

Goke et al., "Exendin-4 Is a High Potency Agonist and Truncated Exendin-(9-39)-amide an Antagonist at the Glucagon-like Peptife 1-(7-36)-amide Receptor of Insulin-secreting-Cells," J. Biol. Chem. 268:19650-55 (1993).

Goke et al, Eur. J. Neurosci., 7:2294-2300 (1995).

Gombotz et al., "Biodegradable Polymers for Protein and Peptide Drug Delivery," Bioconjugate Chemistry 6:332-351 (1995).

Grand, Biochem. J. 258:625-638 (1989).

Grieg et al, Diabetologia, 42:45-50 (1999).

Halaas et al., "weight-Reducing Effects of the Plasma Protein Encoded by the Obese Gene," Science 269:543-546 (1995).

Harlow & Lane, Antibodies: A Laboratory Manual, pp. 101, 129 (1988).

Heithier et al. (1988) Fluorescent Glucagon Derivatives. I. Synthesis and Characterisation of Fluorescent Glucagon Derivatives. Biochim. Biophys. Acta. vol. 971, pp. 298-306.

Hoist, Expert Opin. Emerg. Drugs, 9(1):155-166 (2004).

Hoshino et al, FEBS Lett., 178:233-239 (1984).

Hudecz et al., "Synthesis, Conformation, Biodistribution, and In Vitro Cytotoxicity of Daunomycin-Branced Polypeptide Conjugates," Bioconjugate Chemistry 3:49-57 (1992).

Isoai et al, Biochem. Biophys. Res. Comm., 192:7-14 (1993).

Lewis, Hawley's Condensed Chemical Dictionary, 13th Edition, John Wiley & Sons, Inc. (New York), pp. 487, 815 (1997).

Malhotra et al., "Exendin-4, a new peptide from Heloderma suspectum venom, potentiates cholecystokinin-induced amylase release from rat pancreatic acini," Regulatory Peptides 41:149-56 (1992).

Mattson et al, Mol. Biol. Reports, 17:167-183 (1993).

Meurer et al., Properties of native and in vitro glycosylated forms of the glucagons-like peptide-1 receptor antagonist exendin (9-39), Metabolism Clinical and Experimental 48(6):716-724 (1999).

Montrose-Rafizadeh et al., High Potency Antagonists of the pancreatic GlucagorHike Peptide-1 Receptor; J. Bm. Chem. 272(34):21201-21206 (1997).

O'Halloran et al., "Glucagon-like peptide-1 (7-36)-NH2 : A physiological inhibitor of gastric acid secretion in man," J.Endocrinol 126(1):169-73 (1990).

Orskov et al., "Biological Effects and Metabolic Rates of Glucagon-like Peptide-1 7-36 Amide and glucagonlike Peptide-1 7-37 in Health Subjects are Indistinguishable," Diabetes 42:658-61 (1993).

Pelleymounter et al., Effects of the obese gene product on body weight regulation in ob/ob mice, Science 269:540-543(1995).

Petrella et al, Diabetes, 48:A425 (1999).

Poznansky & Juliano, Pharmacological Reviews, 36:277-335 (1984).

Poznansky et al, FEBS Lett., 239:18-22 (1988).

Pratesi et al., "Poly-L-aspartic acid as a carrier for doxorubicin: a comparative in vivo study of free and polymer bound drug," Brit J. Cancer 52:841-848 (1985).

Raufman et al., "Exendin-3, a novel peptide from Heloderma horridum venom, interacts with vasoactiveintestinal peptide receptors and a newly described receptor on dispersed acini from guinea pig pancreas," J.Biol. Chem. 266:2897 (1991).

Raufman et al., "Truncated Glucagon-Like Peptide-1 Interacts with Exendin Receptors in Dispersed Acini from Guinea Pig Pancreas," J. Biol. Chem. 267:21432-37 (1992).

Raufman, Regulatory Peptides, 61:1-18 (1996).

Richter et al, FEBS Lett., 280:247-250 (1991).

Robberecht et al, Biochem. Biophys. Res. Comm., 130:333-342 (1985).

Sailer et al., "Improved Conjugation of Cytokines Using High Molecular Weight polyethylene glycol): PEG-GM-CSF as a Prototype," Polymer Reprints 38(1):576-577 (1997) (American Chemical Society).

Schepp et al., "Exendin-4 and exendin-(9-39) NH2 : agonist and antagonist, respectively, at the rat parietal cell receptor for glucagon-like peptide 1-(7-36) NH2," Eur. J. Pharm. 269:183-91 (1994).

Schirra etal, J. Clin. Invest, 101:1421-1430 (1988).

Schjoldager et al., "GLP-1 (Glucagon-like Peptide 1) and Truncated GLP-1, Fragments of Human Proglucagon, Inhibit Gastric Acid Secretion in Humans," Dig Dis Sci 34(5):703-8 (1989).

Schmidtler, Am. J. Physiol., 267:G423-432 (1994).

Singh et al. "Use of 123I-Y39) exendin-4 to characterize exendin receptors on dispersed pancreatic acini and gastric chief cells form guinea pig," Regul. Pept. 53:47-59 (1994).

Syed etal, Blood, 89:3243-3252 (1997).

Thorens, "Expression cloning of the pancreatic cell receptor for the gluco-incretin hormone glucagon-like peptide 1," Proc. Natl. Acad. Sci. USA 89:8641-45 (1992).

Thorens et al., "Cloning and Functional Expression of the Human Islet GUM Receptor—Demonstration that Exendin-4 is an Agonist and Exendin-(9-39) an Antagonist of the Receptor," Diabetes 42:1678-1682 (1993).

Tsukada et al., An Anti-<<-Fetoprotein Antibody-Deunorubicin Conjugate with a Novel Poly-L-flutamic Acid Derivative as Intermediate Drug Carrier, JNCI 73:721-729 (1984).

Turton et al., A role for glucagon-like peptide-1 in the central regulation of feeding, Nature 379(6560):69-72 (1996).

Vandermeers et al, FEBS Lett., 166:273-276 (1984).

Vandermeers etal, Eur. J. Biochem., 164:321-327 (1987).

Veale et al., "The presence of islet amyloid polypeptide/calcitonin gen-related peptide/salmon calcitonin binding sites in the rat nucleus accumbens," Eur, J. Pharmacol. 262:133-141 (1994).

Wettergren et al., "Truncated GLP-1 (Proglucagon 78-107-Amide) Inhibits Gastsric and Pancreatic Functions in Man," Dig Dis Sci 38(4):665-73 (1993).

Willms et al., Gastric Emptying, Glucose Responses, and Insulin Secretion after a Liquid Test Meal: Effects of Exogenous Glucagon-Like Peptide-1 (GLP-1)-(7-36) Amide on Type 2 (noninsulin-Dependent) Diabetic Patients. : J. Clin Endocrinol. And Metabolism 81(1κ:327-332 (1996).

Yeh et al, Proc. Natl. Acad. Sci. USA, 89:1904-1908 (1992).

Zalipsky, "Functionalized Poly (ethylene glycol) for Preparation of Biologically Relevant Conjugates," Bioconjugate Chem. 6:150-165(1995).

Request for Inter Partes Reexamination of US Patent No. 6,924,264 filed on Jul. 9, 2007, by ConjuChem Biotechnologies, Inc. (Jul. 9, 2007.

First Declaration of Mark J. Poznansky attached to Request for Inter Partes Reexamination of US Patent No. 6,624,264. (Jul. 6, 2007).

Second Declaration of Mark. J. Poznansky attached to Request for Inter Partes Reexamination of US Patent No. 6,924,264. (Jul. 6, 2007).

Declaration of Omar Quraishi attached to Request for Inter Partes Reexamination of US Patent No. 6,924,264, (Jul. 6, 2007).

U.S. Patent Office Communication dated Oct. 3, 2007, regarding Inter Partes Reexamination of US Patent No. 6,924,264.

U.S. Patent Office Non-Final Office Action dated Jan. 17, 2008, regarding Inter Partes Reexamination of US Patent No. 6,924,264.

U.S. Appl. No. 60/037,413, filed Feb. 5, 1997, Drucker.

U.S. Appl. No. 60/103,498, filed Oct. 8, 1998, Coolidge et al.

U.S. Appl. No. 10/913,309, filed Aug. 6, 2004, Coolidge et al.

Inter Partes Reexamination of U.S. Appl. No. 6,924,264: Petition Under 37 C.F.R. §1.182 for Correction of Second Declaration of Omar Quraishi, filed Jul. 11, 2008.

Inter Partes Reexamination of U.S. Appl. No. 6,924,264: United States Patent Office Action Closing Prosecution, date Mar. 5,2009.

Alberts et al., *Molecular Biology of the Cell. Third Edition* New York: Garland Publishing, pp. 589-591, 606-608 (1994).

Nucci et al., *The Therapeutic Value of Poly(Ethylene glycol)-Modified Proteins,* Adv. Drug Delivery Rev. 6:133-151 (1991).

Parkes et al., *Pharmacokinetic Actions of Exendin-4 in the Rat: Comparison with Glucagon-Like Peptide-1,* Drug Develop. Res. 53:260-267 (2001).

Praz et al., *Regulation of Immunoreactive-Insulin Release from a Rat Cell Line (RINm5F),* Biochem. J. 210:345-352 (1983).

Qiagen, *Q-proteome Plasma Membrane Protein Handbook* (QIAGEN, April 2006).

Simonsen et al., *Exendin-4, but Not Glucagon-like Peptide-1, is Cleared Exclusively by Glomerular Filtration in Anaesthetised Pigs,* Diabetologia 49(4):706-12 (2006).

Tota et al., *Interaction of [fluorescein-Trp25]glucagon with the human glucagon receptor expressed in Drosophila Schneider 2 cells,* J. Biol. Chem. 270:26466-26472 (1995).

Varshavsky, *The Ubiquitin System.* Trends Biochem.Sci . 22(10):383-387 (1997).

Zaidi et al., *Effects of Copper Chloride Toxicity on Corpus Striatum of Rat Brain—A Histological Study,* J.Anat.Soc. India 51(1):55-56 (2002).

* cited by examiner

His Ser Asp Gly Thr Phe Thr Ser Asp Leu Ser Lys Gln Met Glu Glu
1                       5                    10                  15
Glu Ala Val Arg Leu Phe Ile Glu Trp Leu Lys Asn Gly Gly Pro Ser
               20                       25                  30
Ser Gly Ala Pro Pro Pro Ser-NH₂
                  35

Fig. 1

His Gly Glu Gly Thr Phe Thr Ser Asp Leu Ser Lys Gln Met Glu Glu
1                       5                    10                  15
Glu Ala Val Arg Leu Phe Ile Glu Trp Leu Lys Asn Gly Gly Pro Ser
               20                       25                  30
Ser Gly Ala Pro Pro Pro Ser-NH₂
                  35

| SEQ. ID. NO. | Xaa1 | Xaa2 | Xaa3 | Xaa4 | Xaa5 | Xaa6 | Xaa7 | Xaa8 | Xaa9 | Xaa10 | Xaa11 | Xaa12 |
|---|---|---|---|---|---|---|---|---|---|---|---|---|
| 9 | His | Gly | Glu | Phe | Thr | Ser | Asp | Leu | pGly | Phe | Ile | Glu |
| 10 | His | Gly | Glu | Phe | Thr | Ser | Asp | Leu | Met | naph | Ile | Glu |
| 11 | His | Gly | Glu | Phe | Thr | Ser | Asp | Leu | Met | Phe | Val | Glu |
| 12 | His | Gly | Glu | Phe | Thr | Ser | Asp | Leu | Leu | Phe | Val | Glu |
| 13 | His | Gly | Glu | Phe | Thr | Ser | Asp | Leu | Met | Phe | tBuG | Glu |
| 14 | His | Gly | Glu | Phe | Thr | Ser | Asp | Leu | Leu | Phe | tBuG | Glu |
| 15 | His | Gly | Glu | Phe | Thr | Ser | Asp | Leu | Met | Phe | Ile | Asp |
| 16 | His | Ala | Glu | Phe | Thr | Ser | Asp | Leu | Leu | Phe | Ile | Glu |
| 17 | His | Gly | Glu | Phe | Thr | Ser | Asp | Leu | Met | Phe | Ile | Glu |
| 18 | His | Gly | Glu | Phe | Thr | Ser | Asp | Leu | Met | Phe | Ile | Glu |
| 19 | His | Gly | Glu | Phe | Thr | Ser | Asp | Leu | Met | Phe | Ile | Glu |
| 20 | His | Gly | Glu | Phe | Thr | Ser | Asp | Leu | Met | Phe | Ile | Glu |
| 21 | His | Gly | Glu | Phe | Thr | Ser | Asp | Leu | Leu | Phe | Ile | Glu |
| 22 | His | Gly | Glu | Phe | Thr | Ser | Asp | Leu | Leu | Phe | Ile | Glu |
| 23 | His | Gly | Glu | Phe | Thr | Ser | Asp | Leu | Met | Phe | Ile | Glu |
| 24 | His | Gly | Glu | Phe | Thr | Ser | Asp | Leu | Met | Phe | Ile | Glu |
| 25 | His | Gly | Glu | Phe | Thr | Ser | Asp | Leu | Leu | Phe | Ile | Glu |

FIGURE 3A2

| SEQ. ID. NO. | Xaa13 | Xaa14 | Xaa15 | Xaa16 | Xaa17 | Xaa18 | Z |
|---|---|---|---|---|---|---|---|
| 9 | Phe | Pro | Pro | Pro | Pro | Ser | NH$_2$ |
| 10 | Trp | Pro | Pro | Pro | Pro | Ser | NH$_2$ |
| 11 | Trp | Pro | Pro | Pro | Pro | Ser | NH$_2$ |
| 12 | Phe | Pro | Pro | Pro | Pro | Ser | NH$_2$ |
| 13 | Trp | Pro | Pro | Pro | Pro | Ser | NH$_2$ |
| 14 | Phe | Pro | Pro | Pro | Pro | Ser | NH$_2$ |
| 15 | Trp | Pro | Pro | Pro | Pro | Ser | NH$_2$ |
| 16 | Phe | tPro | tPro | tPro | tPro | Ser | NH$_2$ |
| 17 | Trp | Pro | tPro | tPro | tPro | Ser | NH$_2$ |
| 18 | Trp | hPro | hPro | hPro | hPro | Ser | NH$_2$ |
| 19 | Trp | Pro | hPro | hPro | hPro | Ser | NH$_2$ |
| 20 | Trp | tPro | tPro | tPro | tPro | Ser | NH$_2$ |
| 21 | Phe | hPro | hPro | hPro | hPro | Ser | NH$_2$ |
| 22 | Phe | MeAla | MeAla | MeAla | MeAla | Ser | NH$_2$ |
| 23 | Trp | Pro | MeAla | MeAla | MeAla | Ser | NH$_2$ |
| 24 | Trp | tPro | tPro | tPro | tPro | Ser | NH$_2$ |
| 25 | Phe | MeAla | MeAla | MeAla | MeAla | Ser | NH$_2$ |

FIGURE 4A1

| SEQ. ID. NO. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| 26 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 27 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 28 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 29 | His | Ala | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 30 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 31 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 32 | His | Gly | Glu | Gly | Thr | Phe | Thr | Ala | Asp | Leu | Ser | Lys | Gln | Leu | Glu | Glu | Glu | Ala | Val | Arg | Leu | Phe | Ile | Glu | Phe |
| 33 | His | Gly | Glu | Gly | Thr | Phe | Thr | Ser | Asp | Ala | Ser | Lys | Gln | Leu | Glu | Glu | Glu | Ala | Val | Arg | Leu | Phe | Ile | Glu | Phe |
| 34 | His | Gly | Glu | Gly | Thr | Phe | Thr | Ser | Asp | Leu | Ala | Lys | Gln | Leu | Glu | Glu | Glu | Ala | Val | Arg | Leu | Phe | Ile | Glu | Phe |
| 35 | His | Gly | Glu | Gly | Ala | Phe | Thr | Ser | Asp | Leu | Ser | Ala | Gln | Leu | Glu | Glu | Glu | Ala | Val | Arg | Leu | Phe | Ile | Glu | Phe |
| 36 | His | Gly | Glu | Gly | Thr | Phe | Thr | Ser | Asp | Leu | Ser | Lys | Ala | Leu | Glu | Glu | Glu | Ala | Val | Arg | Leu | Phe | Ile | Glu | Phe |
| 37 | His | Gly | Glu | Gly | Thr | Phe | Thr | Ser | Asp | Leu | Ser | Lys | Gln | Ala | Glu | Glu | Glu | Ala | Val | Arg | Leu | Phe | Ile | Glu | Phe |
| 38 | His | Gly | Glu | Gly | Thr | Phe | Thr | Ser | Asp | Leu | Ser | Lys | Gln | Leu | Ala | Glu | Glu | Ala | Val | Arg | Leu | Phe | Ile | Glu | Phe |
| 39 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 40 | His | Gly | Glu | Gly | Thr | Phe | Thr | Ser | Asp | Leu | Ser | Lys | Gln | Leu | Glu | Glu | Ala | Ala | Val | Arg | Leu | Phe | Ile | Glu | Phe |
| 41 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 42 | His | Gly | Glu | Gly | Thr | Phe | Thr | Ser | Asp | Leu | Ser | Lys | Gln | Leu | Glu | Glu | Glu | Ala | Ala | Arg | Leu | Phe | Ile | Glu | Phe |
| 43 | His | Gly | Glu | Gly | Thr | Phe | Thr | Ser | Asp | Leu | Ser | Lys | Gln | Leu | Glu | Glu | Glu | Ala | Val | Ala | Leu | Phe | Ile | Glu | Phe |
| 44 | His | Gly | Glu | Gly | Thr | Phe | Thr | Ser | Asp | Leu | Ser | Lys | Gln | Met | Glu | Glu | Glu | Ala | Val | Arg | Ala | Phe | Ile | Glu | Ala |
| 45 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 46 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 47 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 48 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 49 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 50 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 51 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 52 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 53 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 54 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Ala | Phe |
| 55 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 56 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 57 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 58 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 59 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 60 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 61 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp |
| 62 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |
| 63 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp |
| 64 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Phe |
| 65 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe |
| 66 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp |

FIGURE 4A2

| SEQ. ID. NO. | 26 | 27 | 28 | 29 | 30 | 31 | 32 | 33 | 34 | 35 | 36 | 37 | 38 | 39 |
|---|---|---|---|---|---|---|---|---|---|---|---|---|---|---|
| 26 | Leu | Lys | Asn | Gly | Gly | NH2 | | | | | | | | |
| 27 | Leu | Lys | Asn | NH2 | | | | | | | | | | |
| 28 | Leu | Lys | Asn | NH2 | | | | | | | | | | |
| 29 | Leu | Lys | Asn | NH2 | | | | | | | | | | |
| 30 | Leu | Lys | Asn | NH2 | | | | | | | | | | |
| 31 | Leu | Lys | Asn | NH2 | | | | | | | | | | |
| 32 | Leu | Lys | Asn | NH2 | | | | | | | | | | |
| 33 | Leu | Lys | Asn | NH2 | | | | | | | | | | |
| 34 | Leu | Lys | Asn | NH2 | | | | | | | | | | |
| 35 | Leu | Lys | Asn | NH2 | | | | | | | | | | |
| 36 | Leu | Lys | Asn | NH2 | | | | | | | | | | |
| 37 | Leu | Lys | Asn | NH2 | | | | | | | | | | |
| 38 | Leu | Lys | Asn | NH2 | | | | | | | | | | |
| 39 | Leu | Lys | Asn | NH2 | | | | | | | | | | |
| 40 | Leu | Lys | Asn | NH2 | | | | | | | | | | |
| 41 | Leu | Lys | Asn | NH2 | | | | | | | | | | |
| 42 | Leu | Lys | Asn | NH2 | | | | | | | | | | |
| 43 | Leu | Lys | Asn | NH2 | | | | | | | | | | |
| 44 | Leu | Lys | Asn | NH2 | | | | | | | | | | |
| 45 | Leu | Lys | Asn | NH2 | | | | | | | | | | |
| 46 | Ala | Lys | Asn | NH2 | | | | | | | | | | |
| 47 | Leu | Ala | Ala | NH2 | | | | | | | | | | |
| 48 | Leu | Lys | Asn | NH2 | | | | | | | | | | |
| 49 | Leu | Lys | Asn | Gly | Gly | Pro | Ser | Ser | Gly | Ala | Pro | Pro | Pro | NH2 |
| 50 | Leu | Lys | Asn | Gly | Gly | Pro | Ser | Ser | Gly | Ala | Pro | Pro | Pro | NH2 |
| 51 | Leu | Lys | Asn | Gly | Gly | Pro | Ser | Ser | Gly | Ala | Pro | Pro | NH2 | |
| 52 | Leu | Lys | Asn | Gly | Gly | Pro | Ser | Ser | Gly | Ala | Pro | Pro | NH2 | |
| 53 | Leu | Lys | Asn | Gly | Gly | Pro | Ser | Ser | Gly | Ala | Pro | NH2 | | |
| 54 | Leu | Lys | Asn | Gly | Gly | Pro | Ser | Ser | Gly | Ala | Pro | NH2 | | |
| 55 | Leu | Lys | Asn | Gly | Gly | Pro | Ser | Ser | Gly | Ala | NH2 | | | |
| 56 | Leu | Lys | Asn | Gly | Gly | Pro | Ser | Ser | Gly | Ala | NH2 | | | |
| 57 | Leu | Lys | Asn | Gly | Gly | Pro | Ser | Ser | Gly | NH2 | | | | |
| 58 | Leu | Lys | Asn | Gly | Gly | Pro | Ser | Ser | Gly | NH2 | | | | |
| 59 | Leu | Lys | Asn | Gly | Gly | Pro | Ser | Ser | NH2 | | | | | |
| 60 | Leu | Lys | Asn | Gly | Gly | Pro | Ser | Ser | NH2 | | | | | |
| 61 | Leu | Lys | Asn | Gly | Gly | Pro | Ser | NH2 | | | | | | |
| 62 | Leu | Lys | Asn | Gly | Gly | Pro | Ser | NH2 | | | | | | |
| 63 | Leu | Lys | Asn | Gly | Gly | Pro | NH2 | | | | | | | |
| 64 | Leu | Lys | Asn | Gly | Gly | Pro | NH2 | | | | | | | |
| 65 | Leu | Lys | Asn | Gly | Gly | NH2 | | | | | | | | |
| 66 | Leu | Lys | Asn | Gly | NH2 | | | | | | | | | |

FIGURE 4B1

| SEQ. ID. NO. | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 67 | His | Gly | Glu | Gly | Thr | Phe | Thr | Ser | Asp | Leu | Ser | Lys | Gln | Leu | Glu | Glu | Glu | Ala | Val | Arg | Leu | Phe |
| 68 | His | Gly | Glu | Gly | Thr | Phe | Thr | Ser | Asp | Leu | Ser | Lys | Gln | Met | Glu | Glu | Glu | Ala | Val | Arg | Leu | Phe |
| 69 | His | Gly | Glu | Gly | Thr | Phe | Thr | Ser | Asp | Leu | Ser | Lys | Gln | Met | Glu | Glu | Glu | Ala | Val | Arg | Leu | Phe |
| 70 | His | Gly | Glu | Gly | Thr | Phe | Thr | Ser | Asp | Leu | Ser | Lys | Gln | Met | Glu | Glu | Glu | Ala | Val | Arg | Leu | Phe |
| 71 | His | Gly | Glu | Gly | Thr | Phe | Thr | Ser | Asp | Leu | Ser | Lys | Gln | Met | Glu | Glu | Glu | Ala | Val | Arg | Leu | Phe |
| 72 | His | Gly | Glu | Gly | Thr | Phe | Thr | Ser | Asp | Leu | Ser | Lys | Gln | Met | Glu | Glu | Glu | Ala | Val | Arg | Leu | Phe |
| 73 | His | Gly | Glu | Gly | Thr | Phe | Thr | Ser | Asp | Leu | Ser | Lys | Gln | Met | Glu | Glu | Glu | Ala | Val | Arg | Leu | Phe |
| 74 | Arg | Gly | Glu | Gly | Thr | Phe | Thr | Ser | Asp | Leu | Ser | Lys | Gln | Met | Glu | Glu | Glu | Ala | Val | Arg | Leu | Phe |
| 75 | His | Gly | Asp | Gly | Thr | Phe | Thr | Ser | Asp | Leu | Ser | Lys | Gln | Leu | Glu | Glu | Glu | Ala | Val | Arg | Leu | Phe |
| 76 | His | Gly | Glu | Gly | Thr | naph | Thr | Ser | Asp | Leu | Ser | Lys | Gln | Met | Glu | Glu | Glu | Ala | Val | Arg | Leu | Phe |
| 77 | His | Gly | Glu | Gly | Thr | Phe | Ser | Ser | Asp | Leu | Ser | Lys | Gln | Met | Glu | Glu | Glu | Ala | Val | Arg | Leu | Phe |
| 78 | His | Gly | Glu | Gly | Thr | Phe | Ser | Thr | Asp | Leu | Ser | Lys | Gln | Leu | Glu | Glu | Glu | Ala | Val | Arg | Leu | Phe |
| 79 | His | Gly | Glu | Gly | Thr | Phe | Thr | Ser | Glu | Leu | Ser | Lys | Gln | Met | Glu | Glu | Glu | Ala | Val | Arg | Leu | Phe |
| 80 | His | Gly | Glu | Gly | Thr | Phe | Thr | Ser | Asp | pGly | Ser | Lys | Gln | Leu | Ala | Glu | Glu | Ala | Val | Arg | Leu | naph |
| 81 | His | Gly | Glu | Gly | Thr | Phe | Thr | Ser | Asp | Leu | Ser | Lys | Gln | Leu | Glu | Glu | Glu | Ala | Val | Arg | Leu | Phe |
| 82 | His | Gly | Glu | Gly | Thr | Phe | Thr | Ser | Asp | Leu | Ser | Lys | Gln | Met | Glu | Glu | Glu | Ala | Val | Arg | Leu | Phe |
| 83 | His | Gly | Glu | Gly | Thr | Phe | Thr | Ser | Asp | Leu | Ser | Lys | Gln | Leu | Glu | Glu | Glu | Ala | Val | Arg | Leu | Phe |
| 84 | His | Gly | Glu | Gly | Thr | Phe | Thr | Ser | Asp | Ala | Ser | Lys | Gln | Leu | Glu | Glu | Glu | Ala | Val | Arg | Leu | Phe |
| 85 | His | Gly | Glu | Gly | Thr | Phe | Thr | Ser | Asp | Ala | Ser | Lys | Gln | Met | Glu | Glu | Glu | Ala | Val | Arg | Leu | Phe |
| 86 | His | Gly | Glu | Gly | Thr | Phe | Thr | Ser | Asp | Ala | Ser | Lys | Gln | Met | Glu | Glu | Glu | Ala | Val | Arg | Leu | Phe |

FIGURE 4B2

| SEQ. ID. NO. | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|
| 67 | Ile | Glu | Phe | Leu | Lys | Asn | Gly | NH2 | | | | | | | | | |
| 68 | Ile | Glu | Trp | Leu | Lys | Asn | Gly | Gly | tPro | Ser | Ser | Gly | Ala | tPro | tPro | tPro | NH2 |
| 69 | Ile | Glu | Trp | Leu | Lys | Asn | Gly | Gly | tPro | Ser | Ser | Gly | Ala | tPro | tPro | tPro | NH2 |
| 70 | Ile | Glu | Trp | Leu | Lys | Asn | Gly | Gly | tPro | Ser | Ser | Gly | Ala | Pro | Pro | NH2 | |
| 71 | Ile | Glu | Trp | Leu | Lys | Asn | Gly | Gly | tPro | Ser | Ser | Gly | Ala | Nme | Nme | NH2 | |
| 2 | Ile | Glu | Trp | Leu | Lys | Asn | Gly | Gly | tPro | Ser | Ser | Gly | Ala | hPro | hPro | NH2 | |
| 73 | Ile | Glu | Trp | Leu | Lys | Asn | Gly | Gly | tPro | Ser | Ser | Gly | Ala | hPro | hPro | | |
| 74 | Ile | Glu | Trp | Leu | Lys | Asn | Gly | Gly | tPro | Ser | Ser | Gly | Ala | NH2 | NH2 | | |
| 75 | Ile | Glu | Trp | Leu | Lys | Asn | Gly | Gly | NH2 | | | | | | | | |
| 76 | Ile | Glu | Phe | Leu | Lys | Asn | NH2 | | | | | | | | | | |
| 77 | Ile | Glu | Trp | Leu | Lys | Asn | NH2 | | | | | | | | | | |
| 78 | Ile | Glu | Trp | Leu | Lys | Asn | NH2 | | | | | | | | | | |
| 79 | Ile | Glu | Trp | Leu | Lys | Asn | NH2 | | | | | | | | | | |
| 80 | Ile | Glu | Phe | Leu | Lys | Asn | NH2 | | | | | | | | | | |
| 81 | Ile | Glu | Phe | Leu | Lys | Asn | NH2 | | | | | | | | | | |
| 82 | tBug | Glu | Phe | Leu | Lys | Asn | NH2 | | | | | | | | | | |
| 83 | Ile | Asp | Phe | Leu | Lys | Asn | Gly | Gly | Pro | Ser | Ser | NH2 | | | | | |
| 84 | Ile | Glu | Phe | Leu | Lys | Asn | Gly | NH2 | | | | | | | | | |
| 85 | Ile | Glu | Trp | Leu | Lys | Asn | Gly | Gly | hPro | Ser | Ser | Gly | Ala | hPro | hPro | NH2 | |
| 86 | Ile | Glu | Trp | Leu | Lys | Asn | Gly | Gly | | | | | | | | | |

FIGURE 4C

SEQ. ID. NO.

87. 4-Imidazolylpropionyl-Gly Glu Gly Thr Phe Thr Ser Asp Leu Ser Lys Gln Met Glu Glu Glu Ala Val Arg Leu Phe Ile Glu Trp Leu Lys-NH$^E$octanoyl Asn-NH$_2$ 88. 4-Imidazolylpropionyl-Gly Glu Gly Thr Phe Thr Ser Asp Leu Ser Lys Gln Leu Glu Glu Glu Ala Val Arg Leu Phe Ile Glu Phe Leu Lys-NH$^E$octanoly Asn-NH$_2$ 89. 4-Imidazolylpropionyl-Gly Glu Gly Thr Phe Thr Ser Asp Leu Ser Lys Gln Met Glu Glu Glu Ala Val Arg Leu Phe Ile Glu Trp Leu Lys-NH$^E$octanoyl Asn Gly Gly-NH$_2$ 90. 4-Imidazolylpropionyl-Gly Glu Gly Thr Phe Thr Ser Asp Leu Ser Lys Gln Leu Glu Glu Glu Ala Val Arg Leu Phe Ile Glu Phe Leu Lys-NH$^E$octanoyl Asn Gly Gly-NH$_2$ 91. 4-Imidazolylpropionyl-Gly Glu Gly Thr Phe Thr Ser Asp Leu Ser Lys Gln Met Glu Glu Glu Ala Val Arg Leu Phe Ile Glu Trp Leu Asn Lys-NH$^E$octanoyl-NH$_2$

FIGURE 4D

SEQ. ID. NO.

92. 4-Imidazolylpropionyl-Gly Glu Gly Thr Phe Thr Ser Asp Leu Ser Lys Gln Leu Glu Glu Glu Ala Val Arg Leu Phe Ile Glu Phe Leu Asn Lys-NH$^E$octanoyl-NH$_2$ 93. 4-Imidazolylpropionyl-Gly Glu Gly Thr Phe Thr Ser Asp Leu Ser Lys Gln Met Glu Glu Glu Ala Val Arg Leu Phe Ile Glu Trp Leu Asn Lys-NH$^E$octanoly Gly Gly-NH$_2$ 94. 4-Imidazolylpropionyl-Gly Glu Gly Thr Phe Thr Ser Asp Leu Ser Lys Gln Leu Glu Glu Glu Ala Val Arg Leu Phe Ile Glu Phe Leu Asn Lys-NH$^E$octanoyl Gly Gly-NH$_2$

FIGURE 4E1

| SEQ. ID. NO. | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 95 | Ala | Gly | Glu | Gly | Thr | Phe | Thr | Ser | Asp | Leu | Ser | Lys | Gln | Leu | Glu | Glu | Glu | Ala | Val | Arg | Leu | Phe |
| 96 | His | Gly | Ala | Gly | Thr | Phe | Thr | Ser | Asp | Leu | Ser | Lys | Gln | Leu | Glu | Glu | Glu | Ala | Val | Arg | Leu | Phe |
| 97 | His | Gly | Glu | Ala | Thr | Phe | Thr | Ser | Asp | Leu | Ser | Lys | Gln | Leu | Glu | Glu | Glu | Ala | Val | Arg | Leu | Phe |
| 98 | His | Gly | Glu | Gly | Thr | Phe | Thr | Ser | Asp | Leu | Ser | Lys | Gln | Met | Glu | Glu | Glu | Ala | Val | Arg | Leu | Phe |
| 99 | His | Gly | Ala | Gly | Thr | Phe | Thr | Ser | Asp | Leu | Ser | Lys | Gln | Met | Glu | Glu | Glu | Ala | Val | Arg | Leu | Phe |
| 100 | His | Gly | Glu | Ala | Thr | Phe | Thr | Ser | Asp | Leu | Ser | Lys | Gln | Met | Glu | Glu | Glu | Ala | Val | Arg | Leu | Phe |
| 101 | His | Gly | Ala | Gly | Thr | Phe | Thr | Ser | Ala | Leu | Ser | Lys | Gln | Met | Glu | Glu | Glu | Ala | Val | Arg | Leu | Phe |
| 102 | His | Gly | Glu | Gly | Thr | Phe | Thr | Ser | Asp | Ala | Ser | Lys | Gln | Met | Glu | Glu | Glu | Ala | Val | Arg | Leu | Phe |
| 103 | His | Gly | Glu | Gly | Thr | Phe | Thr | Ser | Asp | Leu | Ser | Lys | Gln | Leu | Glu | Glu | Glu | Ala | Val | Arg | Leu | Phe |
| 104 | Ala | Ala | Glu | Gly | Thr | Phe | Thr | Ser | Asp | Leu | Ser | Lys | Gln | Met | Glu | Glu | Glu | Ala | Val | Arg | Leu | Phe |
| 105 | Ala | Ala | Glu | Gly | Thr | Phe | Thr | Ser | Asp | Leu | Ser | Lys | Gln | Leu | Glu | Glu | Glu | Ala | Val | Arg | Leu | Phe |
| 106 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 107 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 108 | Ala | Gly | Asp | Gly | Ala | Phe | Thr | Ala | Asp | Leu | Ser | Lys | Gln | Met | Glu | Glu | Glu | Ala | Val | Arg | Leu | Phe |
| 109 | Ala | Gly | Asp | Gly | Ala | Phe | Thr | Ala | Asp | Leu | Ser | Lys | Gln | Met | Glu | Glu | Glu | Ala | Val | Arg | Leu | Phe |
| 110 | Ala | Gly | Asp | Gly | Thr | Nala | Thr | Ser | Asp | Leu | Ser | Lys | Gln | Leu | Glu | Glu | Glu | Ala | Val | Arg | Leu | Phe |
| 111 | Ala | Gly | Asp | Gly | Thr | Nala | Thr | Ser | Asp | Leu | Ser | Lys | Gln | Met | Glu | Glu | Glu | Ala | Val | Arg | Leu | Phe |
| 112 | Ala | Gly | Asp | Gly | Thr | Phe | Ser | Ser | Ala | Leu | Ser | Lys | Gln | Leu | Glu | Glu | Glu | Ala | Val | Arg | Leu | Phe |
| 113 | Ala | Gly | Asp | Gly | Thr | Phe | Ser | Ser | Ala | Leu | Ser | Lys | Gln | Met | Glu | Glu | Glu | Ala | Val | Arg | Leu | Phe |
| 114 | Ala | Gly | Asp | Gly | Thr | Phe | Thr | Ser | Glu | Leu | Ser | Lys | Gln | Leu | Glu | Glu | Glu | Ala | Val | Arg | Leu | Phe |
| 115 | Ala | Gly | Asp | Gly | Thr | Phe | Thr | Ser | Glu | Leu | Ser | Lys | Gln | Met | Glu | Glu | Glu | Ala | Val | Arg | Leu | Phe |
| 116 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 117 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 118 | Ala | Gly | Asp | Gly | Thr | Phe | Thr | Ser | Asp | Leu | Ala | Lys | Gln | Leu | Glu | Glu | Glu | Ala | Val | Arg | Leu | Phe |
| 119 | Ala | Gly | Asp | Gly | Thr | Phe | Thr | Ser | Asp | Leu | Ala | Lys | Gln | Met | Glu | Glu | Glu | Ala | Val | Arg | Leu | Phe |
| 120 | Ala | Gly | Asp | Gly | Thr | Phe | Thr | Ser | Asp | Pgly | Ser | Lys | Gln | Leu | Glu | Glu | Glu | Ala | Val | Arg | Leu | Phe |
| 121 | Ala | Gly | Asp | Gly | Thr | Phe | Thr | Ser | Asp | Pgly | Ser | Lys | Gln | Met | Glu | Glu | Glu | Ala | Val | Arg | Leu | Phe |
| 122 | Ala | Gly | Asp | Gly | Thr | Phe | Thr | Ser | Asp | Leu | Ser | Ala | Gln | Leu | Glu | Glu | Glu | Ala | Val | Arg | Leu | Phe |
| 123 | Ala | Gly | Asp | Gly | Thr | Phe | Thr | Ser | Asp | Leu | Ser | Ala | Gln | Met | Glu | Glu | Glu | Ala | Val | Arg | Leu | Phe |
| 124 | Ala | Gly | Asp | Gly | Thr | Phe | Thr | Ser | Asp | Leu | Ser | Lys | Ala | Leu | Glu | Glu | Glu | Ala | Val | Arg | Leu | Phe |
| 125 | Ala | Gly | Asp | Gly | Thr | Phe | Thr | Ser | Asp | Leu | Ser | Lys | Ala | Met | Glu | Glu | Glu | Ala | Val | Arg | Leu | Phe |
| 126 | Ala | Gly | Asp | Gly | Thr | Phe | Thr | Ser | Asp | Leu | Ser | Lys | Gln | Leu | Glu | Glu | Glu | Ala | Val | Arg | Leu | P |
| 127 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 128 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 129 | Ala | Gly | Asp | Gly | Thr | Phe | Thr | Ser | Asp | Leu | Ser | Lys | Gln | Leu | Glu | Glu | Glu | Ala | Val | Arg | Leu | Phe |

FIGURE 4E2

| SEQ. ID. NO. | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|
| 95 | Ile | Glu | Phe | Leu | Lys | Asn | NH2 | | | | | | | | | | |
| 96 | Ile | Glu | Phe | Leu | Lys | Asn | NH2 | | | | | | | | | | |
| 97 | Ile | Glu | Phe | Leu | Lys | Asn | NH2 | | | | | | | | | | |
| 98 | Ile | Glu | Phe | Leu | Lys | Asn | NH2 | | | | | | | | | | |
| 99 | Ile | Glu | Trp | Leu | Lys | Asn | NH2 | | | | | | | | | | |
| 100 | Ile | Glu | Trp | Leu | Lys | Asn | NH2 | | | | | | | | | | |
| 101 | Ile | Glu | Trp | Leu | Lys | Asn | NH2 | | | | | | | | | | |
| 102 | Ile | Glu | Trp | Leu | Lys | Asn | NH2 | | | | | | | | | | |
| 103 | Ile | Glu | Trp | Leu | Lys | Asn | NH2 | | | | | | | | | | |
| 104 | Ile | Glu | Trp | Leu | Lys | Asn | NH2 | | | | | | | | | | |
| 105 | Ile | Glu | Phe | Leu | Lys | Asn | NH2 | | | | | | | | | | |
| 106 | Ile | Glu | Trp | Leu | Lys | Asn | NH2 | | | | | | | | | | |
| 107 | Ile | Glu | Phe | Leu | Lys | Asn | NH2 | | | | | | | | | | |
| 108 | Ile | Glu | Trp | Leu | Lys | Asn | NH2 | | | | | | | | | | |
| 109 | Ile | Glu | Phe | Leu | Lys | Asn | NH2 | | | | | | | | | | |
| 110 | Ile | Glu | Trp | Leu | Lys | Asn | NH2 | | | | | | | | | | |
| 111 | Ile | Glu | Phe | Leu | Lys | Asn | NH2 | | | | | | | | | | |
| 112 | Ile | Glu | Trp | Leu | Lys | Asn | NH2 | | | | | | | | | | |
| 113 | Ile | Glu | Trp | Leu | Lys | Asn | NH2 | | | | | | | | | | |
| 114 | Ile | Glu | Trp | Leu | Lys | Asn | NH2 | | | | | | | | | | |
| 115 | Ile | Glu | Trp | Leu | Lys | Asn | NH2 | | | | | | | | | | |
| 116 | Ile | Glu | Trp | Leu | Lys | Asn | NH2 | | | | | | | | | | |
| 117 | Ile | Glu | Phe | Leu | Lys | Asn | NH2 | | | | | | | | | | |
| 118 | Ile | Glu | Trp | Leu | Lys | Asn | NH2 | | | | | | | | | | |
| 119 | Ile | Glu | Phe | Leu | Lys | Asn | NH2 | | | | | | | | | | |
| 120 | Ile | Glu | Trp | Leu | Lys | Asn | NH2 | | | | | | | | | | |
| 121 | Ile | Glu | Phe | Leu | Lys | Asn | NH2 | | | | | | | | | | |
| 122 | Ile | Glu | Trp | Leu | Lys | Asn | NH2 | | | | | | | | | | |
| 123 | Ile | Glu | Trp | Leu | Lys | Asn | NH2 | | | | | | | | | | |
| 124 | Ile | Glu | Trp | Leu | Lys | Asn | NH2 | | | | | | | | | | |
| 125 | Ile | Glu | Phe | Leu | Lys | Asn | NH2 | | | | | | | | | | |
| 126 | Ile | Glu | Trp | Leu | Lys | Asn | NH2 | | | | | | | | | | |
| 127 | Ile | Glu | Phe | Leu | Lys | Asn | NH2 | | | | | | | | | | |
| 128 | Ile | Glu | Trp | Leu | Lys | Asn | NH2 | | | | | | | | | | |
| 129 | Ile | Glu | Phe | Leu | Lys | Asn | NH2 | | | | | | | | | | |

FIGURE 4F1

| SEQ. ID. NO. | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 130 | Ala | Gly | Asp | Gly | Thr | Phe | Thr | Ser | Asp | Leu | Ser | Lys | Gln | Ala | Glu | Glu | Glu | Ala | Val | Arg | Leu | Phe |
| 131 | Ala | Gly | Asp | Gly | Thr | Phe | Thr | Ser | Asp | Leu | Ser | Lys | Gln | Ala | Glu | Glu | Glu | Ala | Val | Arg | Leu | Phe |
| 132 | Ala | Gly | Asp | Gly | Thr | Phe | Thr | Ser | Asp | Leu | Ser | Lys | Gln | pGly | Glu | Glu | Glu | Ala | Val | Arg | Leu | Phe |
| 133 | Ala | Gly | Asp | Gly | Thr | Phe | Thr | Ser | Asp | Leu | Ser | Lys | Gln | pGly | Glu | Glu | Glu | Ala | Val | Arg | Leu | Phe |
| 134 | Ala | Gly | Asp | Gly | Thr | Phe | Thr | Ser | Asp | Leu | Ser | Lys | Gln | Met | Ala | Glu | Glu | Ala | Val | Arg | Leu | Phe |
| 135 | Ala | Gly | Asp | Gly | Thr | Phe | Thr | Ser | Asp | Leu | Ser | Lys | Gln | Leu | Ala | Ala | Ala | Ala | Ala | Arg | Leu | Phe |
| 136 | Ala | Gly | Asp | Gly | Thr | Phe | Thr | Ser | Asp | Leu | Ser | Lys | Gln | Met | Glu | Ala | Ala | Ala | Ala | Ala | Ala | Phe |
| 137 | Ala | Gly | Asp | Gly | Thr | Phe | Thr | Ser | Asp | Leu | Ser | Lys | Gln | Leu | Glu | Glu | Glu | Ala | Val | Ala | Ala | Phe |
| 138 | Ala | Gly | Asp | Gly | Thr | Phe | Thr | Ser | Asp | Leu | Ser | Lys | Gln | Met | Glu | Glu | Glu | Ala | Ala | Arg | Leu | Phe |
| 139 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 140 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 141 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 142 | Ala | Gly | Asp | Gly | Thr | Phe | Thr | Ser | Asp | Leu | Ser | Lys | Gln | Met | Glu | Glu | Glu | Ala | Val | Arg | Ala | Phe |
| 143 | Ala | Gly | Asp | Gly | Thr | Phe | Thr | Ser | Asp | Leu | Ser | Lys | Gln | Leu | Glu | Glu | Glu | Ala | Val | Ala | Ala | Phe |
| 144 | Ala | Gly | Asp | Gly | Thr | Phe | Thr | Ser | Asp | Leu | Ser | Lys | Gln | Met | Glu | Glu | Glu | Ala | Ala | Ala | Ala | Nala |
| 145 | Ala | Gly | Asp | Gly | Thr | Phe | Thr | Ser | Asp | Leu | Ser | Lys | Gln | Leu | Glu | Glu | Glu | Ala | Val | Arg | Ala | Nala |
| 146 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 147 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 148 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 149 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 150 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 151 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 152 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 153 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 154 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 155 | Ala | Gly | Asp | Ala | Thr | Phe | Thr | Ser | Asp | Leu | Ser | Lys | Gln | Leu | Glu | Glu | Glu | Ala | Val | Arg | Leu | Phe |
| 156 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 157 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 158 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 159 | Ala | Gly | Asp | Gly | Thr | Phe | Thr | Ser | Asp | Leu | Ser | Lys | Gln | Leu | Glu | Glu | Glu | Ala | Val | Arg | Leu | Phe |
| 160 | Ala | Gly | Asp | Gly | Thr | Phe | Thr | Ser | Asp | Leu | Ser | Lys | Gln | Met | Glu | Glu | Glu | Ala | Val | Arg | Leu | Phe |
| 161 | Ala | Gly | Asp | Gly | Thr | Phe | Thr | Ser | Ala | Leu | Ser | Lys | Gln | Leu | Glu | Glu | Glu | Ala | Val | Arg | Leu | Phe |
| 162 | Ala | Gly | Glu | Gly | Thr | Phe | Thr | Ser | Asp | Leu | Ser | Lys | Gln | Met | Glu | Glu | Glu | Ala | Val | Arg | Leu | Phe |
| 163 | His | Gly | Ala | Gly | Thr | Phe | Thr | Ser | Asp | Leu | Ser | Lys | Gln | Leu | Glu | Glu | Glu | Ala | Val | Arg | Leu | Phe |
| 164 | His | Gly | Glu | Gly | Thr | Phe | Thr | Ser | Asp | Leu | Ser | Lys | Gln | Met | Glu | Glu | Glu | Ala | Val | Arg | Leu | Phe |
| 165 | His | Gly | Glu | Gly | Thr | Phe | Thr | Ser | Asp | Leu | Ser | Lys | Gln | Met | Glu | Glu | Glu | Ala | Val | Arg | Leu | Phe |

FIGURE 4F2

| SEQ. ID. NO. | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|
| 130 | Ile | Glu | Trp | Leu | Lys | Asn | NH2 | | | | | | | | | | |
| 131 | Ile | Glu | Phe | Leu | Lys | Asn | NH2 | | | | | | | | | | |
| 132 | Ile | Glu | Trp | Leu | Lys | Asn | NH2 | | | | | | | | | | |
| 133 | Ile | Glu | Phe | Leu | Lys | Asn | NH2 | | | | | | | | | | |
| 134 | Ile | Glu | Trp | Leu | Lys | Asn | NH2 | | | | | | | | | | |
| 135 | Ile | Glu | Phe | Leu | Lys | Asn | NH2 | | | | | | | | | | |
| 136 | Ile | Glu | Trp | Leu | Lys | Asn | NH2 | | | | | | | | | | |
| 137 | Ile | Glu | Phe | Leu | Lys | Asn | NH2 | | | | | | | | | | |
| 138 | Ile | Glu | Trp | Leu | Lys | Asn | NH2 | | | | | | | | | | |
| 139 | Ile | Glu | Phe | Leu | Lys | Asn | NH2 | | | | | | | | | | |
| 140 | Ile | Glu | Trp | Leu | Lys | Asn | NH2 | | | | | | | | | | |
| 141 | Ile | Glu | Phe | Leu | Lys | Asn | NH2 | | | | | | | | | | |
| 142 | Ile | Glu | Trp | Leu | Lys | Asn | NH2 | | | | | | | | | | |
| 143 | Ile | Glu | Phe | Leu | Lys | Asn | NH2 | | | | | | | | | | |
| 144 | Ile | Glu | Trp | Leu | Lys | Asn | NH2 | | | | | | | | | | |
| 145 | Ile | Glu | Phe | Leu | Lys | Asn | NH2 | | | | | | | | | | |
| 146 | Val | Glu | Trp | Leu | Lys | Asn | NH2 | | | | | | | | | | |
| 147 | Val | Glu | Phe | Leu | Lys | Asn | NH2 | | | | | | | | | | |
| 148 | Val | Glu | Ala | Leu | Lys | Asn | NH2 | | | | | | | | | | |
| 149 | tGly | Glu | Ala | Leu | Lys | Asn | NH2 | | | | | | | | | | |
| 150 | tGly | Glu | Trp | Leu | Lys | Asn | NH2 | | | | | | | | | | |
| 151 | Ile | Glu | Phe | Leu | Lys | Asn | NH2 | | | | | | | | | | |
| 152 | Ile | Asp | Trp | Leu | Lys | Asn | NH2 | | | | | | | | | | |
| 153 | Ile | Asp | Phe | Ala | Ala | Ala | NH2 | | | | | | | | | | |
| 154 | Ile | Glu | Ala | Leu | Ala | Ala | NH2 | | | | | | | | | | |
| 155 | Ile | Glu | Ala | Leu | Ala | Ala | NH2 | | | | | | | | | | |
| 156 | Ile | Glu | Trp | Leu | Ala | Ala | NH2 | | | | | | | | | | |
| 157 | Ile | Glu | Phe | Ala | Lys | Asn | NH2 | | | | | | | | | | |
| 158 | Ile | Glu | Trp | Leu | Lys | Asn | NH2 | | | | | | | | | | |
| 159 | Ile | Glu | Phe | Leu | Ala | Ala | NH2 | | | | | | | | | | |
| 160 | Ile | Glu | Trp | Leu | Lys | Ala | NH2 | | | | | | | | | | |
| 161 | Ile | Glu | Phe | Leu | Lys | Ala | NH2 | | | | | | | | | | |
| 162 | Ile | Glu | Trp | Leu | Lys | Asn | Gly | Gly | Pro | Ser | Ser | Gly | Ala | Pro | Pro | Pro | NH2 |
| 163 | Ile | Glu | Phe | Leu | Lys | Asn | Gly | Gly | Pro | Ser | Ser | Gly | Ala | Pro | Pro | Pro | NH2 |
| 164 | Ile | Glu | Trp | Leu | Lys | Asn | Gly | Gly | Pro | Ser | Ser | Gly | Ala | Pro | Pro | NH2 | |
| 165 | Ile | Glu | Trp | Leu | Lys | Asn | Gly | Gly | Pro | Ser | Ser | Gly | Ala | Pro | NH2 | | |

FIGURE 4G1

| SEQ. ID. NO. | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 166 | Ala | Gly | Glu | Gly | Thr | Phe | Thr | Ser | Asp | Ala | Ser | Lys | Gln | Leu | Glu | Glu | Glu | Ala | Val | Arg | Leu | Phe |
| 167 | Ala | Gly | Glu | Gly | Thr | Phe | Thr | Ser | Asp | Leu | Ser | Lys | Gln | Met | Glu | Glu | Glu | Ala | Val | Arg | Leu | Phe |
| 168 | His | Gly | Ala | Ala | Thr | Phe | Thr | Ser | Asp | Leu | Ser | Lys | Gln | Leu | Glu | Glu | Glu | Ala | Val | Arg | Leu | Phe |
| 169 | His | Gly | Glu | Gly | Thr | Phe | Thr | Ser | Asp | Leu | Ser | Lys | Gln | Met | Glu | Glu | Glu | Ala | Val | Arg | Leu | Phe |
| 170 | His | Gly | Glu | Gly | Thr | Phe | Thr | Ser | Ala | Leu | Ser | Lys | Gln | Met | Glu | Glu | Glu | Ala | Val | Arg | Leu | Phe |
| 171 | Ala | Gly | Glu | Gly | Thr | Phe | Thr | Ser | Asp | Leu | Ser | Lys | Gln | Leu | Glu | Glu | Glu | Ala | Val | Arg | Leu | Phe |
| 172 | His | Gly | Ala | Ala | Thr | Phe | Thr | Ser | Asp | Leu | Ser | Lys | Gln | Met | Glu | Glu | Glu | Ala | Val | Arg | Leu | Phe |
| 173 | His | Gly | Glu | Gly | Thr | Phe | Thr | Ser | Asp | Leu | Ser | Lys | Gln | Leu | Glu | Glu | Glu | Ala | Val | Arg | Leu | Phe |
| 174 | His | Gly | Glu | Ala | Thr | Phe | Thr | Ser | Ala | Leu | Ser | Lys | Gln | Met | Glu | Glu | Glu | Ala | Val | Arg | Leu | Phe |
| 175 | Ala | Gly | Glu | Gly | Thr | Phe | Thr | Ser | Asp | Leu | Ser | Lys | Gln | Leu | Glu | Glu | Glu | Ala | Val | Arg | Leu | Phe |
| 176 | His | Gly | Glu | Gly | Ala | Phe | Thr | Ser | Asp | Leu | Ser | Lys | Gln | Met | Glu | Glu | Glu | Ala | Val | Arg | Leu | Phe |
| 177 | His | Gly | Glu | Ala | Thr | Phe | Thr | Ser | Asp | Leu | Ser | Lys | Gln | Met | Glu | Glu | Glu | Ala | Val | Arg | Leu | Phe |
| 178 | Ala | Gly | Glu | Gly | Thr | Phe | Thr | Ser | Asp | Leu | Ser | Lys | Gln | Met | Glu | Glu | Glu | Ala | Val | Arg | Leu | Phe |
| 179 | His | Gly | Ala | Ala | Thr | Phe | Thr | Ser | Asp | Leu | Ser | Lys | Gln | Met | Glu | Glu | Glu | Ala | Val | Arg | Leu | Phe |
| 180 | His | Gly | Glu | Gly | Thr | Phe | Thr | Ser | Asp | Leu | Ser | Lys | Gln | Met | Glu | Glu | Glu | Ala | Val | Arg | Leu | Phe |
| 181 | His | Gly | Asp | Ala | Thr | Phe | Thr | Ser | Asp | Leu | Ser | Lys | Gln | Met | Glu | Glu | Glu | Ala | Val | Arg | Leu | Phe |
| 182 | Ala | Gly | Glu | Gly | Thr | Phe | Thr | Ser | Asp | Leu | Ser | Lys | Gln | Met | Glu | Glu | Glu | Ala | Val | Arg | Leu | Phe |
| 183 | Ala | Gly | Ala | Gly | Thr | Phe | Thr | Ser | Asp | Leu | Ser | Lys | Gln | Leu | Glu | Glu | Glu | Ala | Val | Arg | Leu | Phe |

FIGURE 4G2

| SEQ. ID. NO. | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|
| 166 | Ile | Glu | Phe | Leu | Lys | Asn | Gly | Gly | Pro | Ser | Ser | Gly | Ala | Pro | NH2 | | | |
| 167 | Ile | Glu | Trp | Leu | Lys | Asn | Gly | Gly | Pro | Ser | Ser | Gly | Ala | NH2 | | | | |
| 168 | Ile | Glu | Phe | Leu | Lys | Asn | Gly | Gly | Pro | Ser | Ser | Gly | Ala | NH2 | | | | |
| 169 | Ile | Glu | Trp | Leu | Lys | Asn | Gly | Gly | Pro | Ser | Ser | Gly | NH2 | | | | | |
| 170 | Ile | Glu | Trp | Leu | Lys | Asn | Gly | Gly | Pro | Ser | Ser | NH2 | | | | | | |
| 171 | Ile | Glu | Trp | Leu | Lys | Asn | Gly | Gly | Pro | Ser | NH2 | | | | | | | |
| 172 | Ile | Glu | Phe | Leu | Lys | Asn | Gly | Gly | Pro | Ser | NH2 | | | | | | | |
| 173 | Ile | Glu | Trp | Leu | Lys | Asn | Gly | Gly | Pro | NH2 | | | | | | | | |
| 174 | Ile | Glu | Phe | Leu | Lys | Asn | Gly | Gly | NH2 | | | | | | | | | |
| 175 | Ile | Glu | Phe | Leu | Lys | Asn | Gly | NH2 | | | | | | | | | | |
| 176 | Ile | Glu | Trp | Leu | Lys | Asn | Gly | Gly | tPro | Ser | Ser | Gly | Ala | tPro | tPro | tPro | NH2 | |
| 177 | Ile | Glu | Trp | Leu | Lys | Asn | Gly | Gly | Pro | Ser | Ser | Gly | Ala | tPro | tPro | tPro | NH2 | |
| 178 | Ile | Glu | Trp | Leu | Lys | Asn | Gly | Gly | Nme | Ser | Ser | Gly | Ala | Nme | Nme | NH2 | | |
| 179 | Ile | Glu | Trp | Leu | Lys | Asn | Gly | Gly | hPro | Ser | Ser | Gly | Ala | hPro | NH2 | | | |
| 180 | Ile | Glu | Trp | Leu | Lys | Asn | Gly | Gly | Pro | Ser | Ser | Gly | Ala | NH2 | | | | |
| 181 | Ile | Glu | Trp | Leu | Lys | Asn | Gly | Gly | NH2 | | | | | | | | | |
| 182 | Ile | Glu | Trp | Leu | Lys | Asn | Gly | Gly | Pro | Ser | Ser | Gly | Ala | Pro | Pro | Pro | Ser | NH2 |
| 183 | Ile | Glu | Phe | Leu | Lys | Asn | Gly | Gly | Pro | Ser | Ser | Gly | Ala | Pro | Pro | Pro | Ser | NH2 |

FIGURE 4H

SEQ ID NO.

184  4-Imidazolylpropionyl-Gly Glu Gly Thr Phe Thr Ser Ala Leu Ser Lys Gln Met Glu Glu Glu
     Ala Val Arg Leu Phe Ile Glu Trp Leu Lys-NH$^E$octanoyl Asn-NH$_2$ 185  4-Imidazolylpropionyl-Gly Glu Gly Thr Phe Thr Ser Ala Leu Ser Lys Gln Leu Glu Glu Glu
     Ala Val Arg Leu Phe Ile Glu Phe Leu Lys-NH$^E$octanoyl Asn-NH$_2$ 186  4-Imidazolylpropionyl-Gly Glu Gly Thr Phe Thr Ser Ala Leu Ser Lys Gln Met Glu Glu Glu
     Ala Val Arg Leu Phe Ile Glu Trp Leu Lys-NH$^E$octanoyl Asn Gly Gly-NH$_2$ 187  4-Imidazolylpropionyl-Gly Glu Gly Thr Phe Thr Ser Ala Leu Ser Lys Gln Leu Glu Glu Glu
     Ala Val Arg Leu Phe Ile Glu Phe Leu Lys-NH$^E$octanoyl Asn Gly Gly-NH$_2$ 188  4-Imidazolylpropionyl-Gly Glu Gly Thr Phe Thr Ser Ala Leu Ser Lys Gln Met Glu Glu Glu
     Ala Val Arg Leu Phe Ile Glu Trp Leu Asn Lys-NH$^E$octanoyl-NH$_2$ 189  4-Imidazolylpropionyl-Gly Glu Gly Thr Phe Thr Ser Ala Leu Ser Lys Gln Leu Glu Glu Glu
     Ala Val Arg Leu Phe Ile Glu Phe Leu Asn Lys-NH$^E$octanoyl-NH$_2$

FIGURE 4I

SEQ ID NO.

190. 4-Imidazolylpropionyl-Gly Glu Gly Thr Phe Thr Ser Ala Leu Ser Lys Gln Met Glu Glu Glu Ala Val Arg Leu Phe Ile Glu Trp Leu Asn Lys-NH$^E$octanoyl Gly Gly-NH$_2$ 191. 4-Imidazolylpropionyl-Gly Glu Gly Thr Phe Thr Ser Ala Leu Ser Lys Gln Leu Glu Glu Glu Ala Val Arg Leu Phe Ile Glu Phe Leu Asn Lys-NH$^E$octanoyl Gly Gly-NH$_2$ 192. Ala Gly Glu Gly Thr Phe Thr Ser Asp Leu Ser Lys Gln Met Glu Glu Ala Val Arg Leu Phe Ile Glu Trp Leu Lys-NH$^E$octanoyl Asn-NH$_2$ 193. Ala Gly Glu Gly Thr Phe Thr Ser Asp Leu Ser Lys Gln Leu Glu Glu Ala Val Arg Leu Phe Ile Glu Phe Leu Lys-NH$^E$octanoyl Asn-NH$_2$ 194. Ala Gly Glu Gly Thr Phe Thr Ser Asp Leu Ser Lys Gln Met Glu Glu Ala Val Arg Leu Phe Ile Glu Trp Leu Lys-NH$^E$octanoyl Asn Gly Gly-NH$_2$ 195. Ala Gly Glu Gly Thr Phe Thr Ser Asp Leu Ser Lys Gln Leu Glu Glu Ala Val Arg Leu Phe Ile Glu Phe Leu Lys-NH$^E$octanoyl Asn Gly Gly-NH$_2$

FIGURE 4J

SEQ ID NO.

196 Ala Gly Glu Gly Thr Phe Thr Ser Asp Leu Ser Lys Gln Met Glu Glu Ala Val Arg Leu Phe
Ile Glu Trp Leu Asn Lys-NH$^E$octanoyl-NH$_2$ 197 Ala Gly Glu Gly Thr Phe Thr Ser Asp Leu Ser Lys Gln Leu Glu Glu Ala Val Arg Leu Phe
Ile Glu Phe Leu Asn Lys-NH$^E$octanoyl-NH$_2$ 198 Ala Gly Glu Gly Thr Phe Thr Ser Asp Leu Ser Lys Gln Met Glu Glu Ala Val Arg Leu Phe
Ile Glu Trp Leu Asn Lys-NH$^E$octanoyl Gly Gly-NH$_2$ 199 Ala Gly Glu Gly Thr Phe Thr Ser Asp Leu Ser Lys Gln Leu Glu Glu Ala Val Arg Leu Phe
Ile Glu Phe Leu Asn Lys-NH$^E$octanoyl Gly Gly-NH$_2$

EXENDINS AND EXENDIN AGONISTS MODIFIED WITH POLYAMINO ACIDS

RELATED APPLICATIONS

This application is a continuation of U.S. application Ser. No. 12/046,038 filed 11 Mar. 2008, which is a continuation of U.S. application Ser. No. 11/174,089 filed 30 Jun. 2005, which is a continuation of U.S. application Ser. No. 09/561,226 filed 28 Apr. 2000, issued as U.S. Pat. No. 6,924,264, which claims priority to U.S. Application No. 60/132,018 filed 30 Apr. 1999, which applications are hereby incorporated by reference in their entirety. This application is related to PCT/US00/11814 filed 28 Apr. 2000, published as WO 00/66629.

FIELD OF THE INVENTION

The present invention relates to novel modified exendins and exendin agonists having an exendin or exendin agonist peptide linked to one or more polyethylene glycol polymers (or other molecular weight increasing agents), and related products and methods that are useful, for example, in the treatment of diabetes, including Type 1 and 2 diabetes, in the treatment of disorders which would be benefited by agents which modulate plasma glucose levels, and in the treatment of disorders which would be benefited by the administration of agents useful in modulating glucagon or triglyceride levels, or the rate of gastric emptying or food intake, including obesity, eating disorders, and insulin-resistance syndrome.

BACKGROUND

The following description includes information that may be useful in understanding the present invention. It is not an admission that any of the information provided herein is prior art to the presently claimed invention, nor that any of the publications specifically or implicitly referenced are prior art to that invention.

The exendins are peptides that are found in the salivary secretions of the Gila monster and the Mexican Bearded Lizard, reptiles that are endogenous to Arizona and Northern Mexico. Exendin-3 (SEQ ID NO: 1) is present in the salivary secretions of *Heloderma horridum* (Mexican Beaded Lizard), and exendin-4 (SEQ ID NO: 2) is present in the salivary secretions of *Heloderm suspectum* (Gila monster)(Eng et al, J. Biol. Chem., 265:20259-62 (1990); Eng et al, J. Biol. Chem., 267:7402-05 (1992). The amino acid sequence of exendin-3 is shown in FIG. 1. The amino acid sequence of exendin-4 is shown in FIG. 2. Exendin-4 was first thought to be a (potentially toxic) component of the venom. It now appears that exendin-4 is devoid of toxicity, and that it instead is made in salivary glands in the Gila monster.

The exendins have some sequence similarity to several members of the glucagon-like peptide family, with the highest homology, 53%, being to GLP-1[7-36]NH$_2$ (SEQ ID NO: 3) (Goke et al, J. Biol. Chem., 268:19650-55 (1993). GLP-1 [7-36]NH$_2$, also sometimes referred to as proglucagon[78-107] or simply "GLP-1", has an insulinotropic effect, stimulating insulin secretion from pancreatic beta-cells; GLP-1 has also been reported to inhibit glucagon secretion from pancreatic alpha-cells (Ørsov et al, Diabetes, 42:658-61 (1993); D'Alessio et al, J. Clin. Invest., 97:133-38 (1996)). GLP-1 has been reported to inhibit gastric emptying (Willms et al, J. Clin. Endocrinol. Metab., 81(1):327-32 (1996); Wettergren et al, Dig. Dis. Sci., 38(4):665-73 (1993)), and gastric acid secretion (Schjoldager et al, Dig. Dis. Sci., 34(5):703-8 (1989); O'Halloran et al, J. Endocrinol., 126(1):169-73 (1990); Wettergren et al, Dig. Dis. Sci., 38(4):665-73 (1993)). GLP-1[7-37], which has an additional glycine residue at its carboxy terminus, is reported to stimulate insulin secretion in humans (Ørsov et al, Diabetes, 42:658-61 (1993)). Other reports relate to the inhibition of glucagon secretion (Creutzfeldt et al, "Glucagonostatic actions and reduction of fasting hyperglycemia by exogenous glucagon-like peptide I(7-36) amide in Type 1 diabetic patients," Diabetes Care, 19(6):580-6 (1996)), and a purported role in appetite control (Turton et al, "A role for glucagon-like peptide-1 in the central regulation of feeding," Nature, 379(6560):69-72 (1996)). A transmembrane G-protein adenylate-cyclase-coupled receptor, said to be responsible at least in part for the insulinotropic effect of GLP-1, has reportedly been cloned from a beta-cell line (Thorens, Proc. Natl. Acad. Sci. USA, 89:8641-45 (1992)). GLP-1 has been the focus of significant investigation in recent years due to its reported action on the amplification of stimulated insulin production (Byrne M M, Goke B. *Lessons from human studies with glucagon-like peptide-1: Potential of the gut hormone for clinical use*. In: Fehmann H C, Goke B. *Insulinotropic Gut Hormone Glucagon-Like Peptide* 1. Basel, Switzerland: Karger, 1997:219-33).

GLP-1 has also been reported to restore islet glucose sensitivity in aging rats, restoring their glucose tolerance to that of younger rats (Egan J M, et al., Diabetologia 1997 June; 40(Suppl 1):A130). However, the short duration of biological action of GLP-1 in vivo is one feature of the peptide that has hampered its development as a therapeutic agent. Various methods have been tried to prolong the half-life of GLP-1 or GLP-1 (7-37), including attempts to alter their amino acid sequences and to deliver them using certain formulations (see, e.g., European Patent Application, entitled "Prolonged Delivery of Peptides," by Darley, et al., publication number 0 619 322 A2, regarding the inclusion of polyethylene glycol in formulations containing GLP-1 (7-37)).

Pharmacological studies have led to reports that exendin-4 can act at GLP-1 receptors in vitro on certain insulin-secreting cells, at dispersed acinar cells from guinea pig pancreas, and at parietal cells from stomach; the peptide is also reported to stimulate somatostatin release and inhibit gastrin release in isolated stomachs (Goke, et al., J. Biol. Chem. 268:19650-55, 1993; Schepp, et al., Eur. J. Pharmacol., 69:183-91, 1994; Eissele, et al., Life Sci., 55:629-34, 1994). Exendin-3 and exendin-4 were reportedly found to stimulate cAMP production in, and amylase release from, pancreatic acinar cells (Malhotra, R., et al., Regulatory Peptides, 41:149-56, 1992; Raulman, et al., J. Biol. Chem. 267:21432-37, 1992; Singh, et al., Regul Pept. 53:47-59, 1994). Exendin-4 has a significantly longer duration of action than GLP-1. For example, in one experiment, glucose lowering by exendin-4 in diabetic mice was reported to persist for several hours, and, depending on dose, for up to 24 hours (Eng, J. Prolonged effect of exendin-4 on hyperglycemia of db/db mice, Diabetes 1996 May; 45(Suppl 2):152A (abstract 554)). Based on their insulinotropic activities, the use of exendin-3 and exendin-4 for the treatment of diabetes mellitus and the prevention of hyperglycemia has been proposed (Eng, U.S. Pat. No. 5,424,286).

The results of an investigation which showed that exendins are not the species homolog of mammalian GLP-1 was reported by Chen and Drucker who cloned the exendin gene from the Gila monster (J. Biol. Chem. 272(7):4108-15 (1997)). The observation that the Gila monster also has separate genes for proglucagons (from which GLP-1 is processed), that are more similar to mammalian proglucagon than exendin, indicated that exendins are not merely species homologs of GLP-1.

Methods for regulating gastrointestinal motility using exendin agonists are described in U.S. Pat. No. 6,858,576 (i.e., based on U.S. application Ser. No. 08/908,867 filed Aug. 8, 1997, which is a continuation-in-part of U.S. application Ser. No. 08/694,954 filed Aug. 8, 1996). Methods for reducing food intake using exendin agonists are described in U.S. Pat. No. 6,956,026 (i.e., based on U.S. application Ser. No. 09/003,869, filed Jan. 7, 1998, which claims the benefit of U.S. Application Nos. 60/034,905 filed Jan. 7, 1997, 60/055, 404 filed Aug. 7, 1997, 60/065,442 filed Nov. 14, 1997, and 60/066,029 filed Nov. 14, 1997.

Novel exendin agonist compounds are described in WO 99/07404 (i.e., PCT/US98/16387 filed Aug. 6, 1998, which claims the benefit of U.S. Patent Application Ser. No. 60/055, 404, filed Aug. 8, 1997). Other novel exendin agonists are described in WO 99/25727 (i.e., PCT/US98/24210, filed Nov. 13, 1998, which claims the benefit of U.S. Provisional Application No. 60/065,442 filed Nov. 14, 1997). Still other novel exendin agonists are described in WO 99/25728 (i.e., PCT/US98/24273, filed Nov. 13, 1998, which claims the benefit of U.S. Provisional Application No. 60/066,029 filed Nov. 14, 1997). Other recent advances in exendin related technology are described in WO 99/40788 (i.e., which claims priority to U.S. Application No. 60/075,122, filed Feb. 13, 1998); and in WO 00/41546, and WO 00/41548 (i.e., which claim priority to U.S. Application No. 60/116,380, filed Jan. 14, 1998).

Polyethylene glycol (PEG) modification of therapeutic peptides and proteins may yield both advantages and disadvantages. While PEG modification may lead to improved circulation time, reduced antigenicity and immunogenicity, improved solubility, resistance to proteolysis, improved bioavailability, reduced toxicity, improved stability, and easier formulation of peptides (See, Francis et al., *International Journal of Hematology*, 68:1-18, 1998) problems with PEGylation in most cases is substantial reduction in bioactivity. Id. In addition, most methods involve use of linkers that have several types of adverse effects including immunogenicity, instability, toxicity, and reactivity. Id.

Modified exendins and exendin agonists and related formulations, dosage formulations, and methods that solve these problems and that are useful in the delivery of therapeutically effective amounts of exendins and exendin agonists are described and claimed herein.

The contents of the above-identified articles, patents, and patent applications, and all other documents mentioned or cited herein, are hereby incorporated by reference in their entirety. The inventors reserve the right to physically incorporate into this application any and all materials and information from any such articles, patents, patent applications, or other documents mentioned or cited herein.

SUMMARY OF THE INVENTION

The present invention relates to novel modified exendins and exendin agonists having an exendin or exendin agonist linked to one or more molecular weight increasing compounds, of which polyethylene glycol polymers (or other molecular weight increasing agents), and related products and methods. Such products and methods that are useful for many applications, including, for example, in the treatment of diabetes, including Type 1 and 2 diabetes, gestational diabetes (see U.S. Pat. No. 6,506,724 which issued from U.S. application Ser. No. 09/323,867, filed Jun. 1, 1999), in the treatment of disorders which would be benefited by agents which modulate plasma glucose levels, in the treatment of disorders which would be benefited by the administration of agents useful in modulating the rate of gastric emptying or food intake, including obesity, eating disorders, and insulin-resistance syndrome, and to modulate triglyceride levels and to treat subjects suffering from dyslipidemia (i.e., increased low-density lipoprotien (LDL) cholesterol, increased very-low-density lipoprotien (VLDL) cholesterol, and/or decreased high-density lipoprotien (HDL) cholesterol) (see WO 00/41546, WO 00/41548, and WO 01/51078, each of which claim priority to U.S. Application No. 60/175,365, filed Jan. 10, 2000). The methods are also useful for lowering plasma lipid levels, reducing cardiac risk, reducing the appetite, and reducing the weight of subjects. Still other embodiments concern methods for suppressing glucagon secretion (see WO 00/41546, WO 00/41548, and WO 01/51078, each of which claim priority to 60/132,017, filed Apr. 30, 1999). Pharmaceutical compositions for use in the methods of the invention are also disclosed.

The present invention is related to the surprising discovery that exendin is cleared from the plasma almost entirely by renal filtration, and not primarily by proteolytic degradation, as occurs for many other biologically active peptides, for example, GLP-1. This surprising discovery supports the determination that PEGylation or other modification of exendin or exendin agonists to increase molecular size, will have pharmaceutical benefit.

Thus, the present invention provides a modified exendin or exendin agonist having an exendin or exendin agonist linked to one or more polyethylene glycol polymers or other molecular weight increasing compounds. A "molecular weight increasing compound" is one that can be conjugated to an exendin or exendin agonist and thereby increase the molecular weight of the resulting conjugate. Representative examples of molecular weight increasing compounds, in addition to PEG, are polyamino acids (e.g., poly-lysine, poly-glutamic acid, and poly-aspartic acid; see Gombotz, et al. (1995), *Bioconjugate Chem.*, vol. 6: 332-351; Hudecz, et al. (1992), *Bioconjugate Chem.*, vol. 3, 49-57; Tsukada, et al. (1984), *J. Natl. Cancer Inst.*, vol 73,: 721-729; Pratesi, et al. (1985), *Br. J. Cancer*, vol. 52: 841-848), particularly those of the L conformation, pharmacologically inactive proteins (e.g., albumin; see Gombotz, et al. (1995) and the references cited therein), gelatin (see Gombotz, et al. (1995) and the references cited therein), succinyl-gelatin (see Gombotz, et al. (1995) and the references cited therein), (hydroxypropyl)-methacrylamide (see Gombotz, et al. (1995) and the references cited therein), a fatty acid, a polysaccharide, a lipid amino acid, and dextran.

In preferred embodiments, the modified exendin or exendin agonist has a molecular weight that is greater than the molecular weight of the exendin or exendin agonist (preferably about 10%, 50% or 90% greater), the modified exendin or exendin agonist has a negative charge that is greater than the negative charge of the exendin or exendin agonist (preferably about 10%, 50% or 90% greater), the modified exendin or exendin agonist has a kidney clearance that is less than the kidney clearance of the exendin or exendin agonist (preferably about 10%, 50% or 90% less), the modified exendin or exendin agonist has a half-life that is greater than the half-life of the exendin or exendin agonist (preferably about 10%, 50% or 90% greater), the modified exendin or exendin agonist has a immunogenicity/antigenicity that is less than the immunogenicity/antigenicity of the exendin or exendin agonist, the modified exendin or exendin agonist has a solubility that is greater than the solubility of the exendin or exendin agonist (preferably about 10%, 50% or 90% greater), the modified exendin or exendin agonist has a proteolysis rate that is less than the proteolysis rate of the exendin or exendin agonist (preferably about 10%, 50% or 90% less), the modified exendin or exendin agonist has a toxicity that is less than the toxicity of the exendin or exendin agonist, the modified exendin or exendin agonist has a stability that is greater than the stability of the exendin or exendin agonist, and/or the modified exendin or exendin agonist has a permeability/biological function that is greater or less than the permeability/biological function of the exendin or exendin agonist (preferably about 10%, 50% or 90% greater or less).

The exendin or exendin agonist may be linked to one, two or three polyethylene glycol polymers or other molecular weight increasing agents. The polyethylene glycol polymers (or other molecular weight increasing agents) may preferably have molecular weights between 500 and 20,000. In a preferred embodiment, the modified exendin or exendin agonist is one of compounds 201-230, more preferably one of compounds 209, 210 and 213, or one of compounds 201 and 202, or one of compounds 216 and 217 (See Example 4 below).

The polyethylene glycol polymers (or other molecular weight increasing agents) are preferably linked to an amino, carboxyl, or thio group, and may be linked by N or C termini of side chains of lysine, aspartic acid, glutamic acid, or cysteine, or alternatively, the polyethylene glycol polymers or other molecular weight increasing agents may be linked with diamine and dicarboxylic groups. The exendin or exendin agonist is preferably linked to the polyethylene glycol polymers or other molecular weight increasing agents through an epsilon amino group on a lysine amino acid of the exendin or exendin agonist.

The present invention also features a method of making a modified exendin or exendin agonist. The method involves linking one or more polyethylene glycol polymers or other molecular weight increasing agents to an exendin or exendin agonist. In preferred embodiments, the linking is performed by solid-phase synthesis.

The present invention also provides a method of treating a disease benefited by administration of an exendin or exendin agonist. The method involves providing a modified exendin or exendin agonist of the invention to a patient having such a disease and thereby treating the disease. Exemplary diseases include postprandial dumping syndrome, postprandial hyperglycemia, impaired glucose tolerance, a condition or disorder which can be alleviated by reducing food intake, obesity, an eating disorder, insulin-resistance syndrome, diabetes mellitus, and a hyperglycemic condition. In a preferred embodiment, the postprandial hyperglycemia is a consequence of Type 2 diabetes mellitus. In other preferred embodiments, the postprandial hyperglycemia is a consequence of Type 1 diabetes mellitus or impaired glucose tolerance.

Also featured in the present invention is a pharmaceutical composition. The composition contains a modified exendin or exendin agonist and a pharmaceutically acceptable carrier.

The invention also provides a kit. The kit contains a modified exendin or exendin agonist and instructions and/or packaging for use. The kit may also include a document indicating that the kit, its components, or the methods of using them, has received regulatory approval.

The present invention also provides a method of beneficially regulating gastro-intestinal motility in a subject. The method involves administering to the subject a therapeutically effective amount of a modified exendin or exendin agonist of the present invention.

Also featured are methods of treatment for ingestion of a toxin. The methods involve: (a) administering an amount of a modified exendin or exendin agonist of the present invention effective to prevent or reduce the passage of stomach contents to the intestines; and (b) aspirating the contents of the stomach.

The invention also provides methods for reducing the appetite or weight, or lowering plasma lipids, of a subject, as well as methods for treating gestational diabetes. The invention also provides methods for reducing the appetite or weight, or lowering plasma lipids, of a subject, as well as methods for treating gestational diabetes. Additional methods include modulating triglyceride levels, and treating subjects suffering from dyslipidemia, as well as suppressing glucagon levels. These and other methods of the invention involve administering to the subject a therapeutically effective amount of a modified exendin or exendin agonist of the present invention.

Modified exendins and exendin agonists are useful, for example, as inhibitors of gastric emptying for the treatment of, for example, diabetes mellitus, and obesity. Thus, the present invention is also directed to novel methods for reducing gastric motility and slowing gastric emptying. The methods involve the administration of a modified exendin or exendin agonist, for example one or more PEG polymers linked to exendin-3 (SEQ ID NO: 1), exendin-4 (SEQ ID NO: 2), or other compounds which effectively bind to the receptor at which exendins exert their action on gastric motility and gastric emptying. These methods will be useful in the treatment of, for example, post-prandial hyperglycemia, a complication associated with type 1 (insulin dependent) and type 2 (non-insulin dependent) diabetes mellitus, as well as gestational diabetes, dyslipidemia, to modulate triglyceride levels, and to suppress glucagon secretion.

By "exendin agonist" is meant a compound which mimics the effects of exendins, e.g., on gastric motility and gastric emptying (namely, a compound which effectively binds to the receptor at which exendins exert their action on gastric motility and gastric emptying, preferably an analog or derivative of an exendin) or a compound, e.g., that mimics the effects of exendin on the reduction of food intake by binding to the receptor or receptors where exendin causes this effect. Preferred exendin agonist compounds include those described in U.S. Pat. No. 5,956,026, filed as US Application No. 90/003,869 on Jan. 7, 1998 (and the priority applications thereto) which enjoys common ownership with the present application and which is incorporated by this reference into the present application as though fully set forth herein. Effects of exendins or exendin agonists on reducing food intake can be identified, evaluated, or screened for, using the methods described herein, or other methods known in the art for determining exendin effects, e.g., on food intake or appetite.

In another aspect, a therapeutically effective amount of an amylin agonist is also administered to the subject. In a preferred aspect, the amylin agonist is an amylin or an amylin agonist analog such as $^{25,28,29}$Pro-human-amylin. The use of amylin agonists to treat post-prandial hyperglycemia, as well as to beneficially regulate gastrointestinal motility, is described in International Application No. PCT/US94/10225, published Mar. 16, 1995 which has been incorporated by reference herein.

In yet another aspect, a therapeutically effective amount of an insulin or insulin analog is also administered, separately or together with a modified exendin or exendin agonist, to the subject.

Preferably, the subject is a vertebrate, more preferably a mammal, and most preferably a human. In preferred aspects, the modified exendin or exendin agonist of the invention is administered parenterally, more preferably by injection. In a most preferred aspect, the injection is a peripheral injection. Preferably, about 1 µg-30 µg to about 5 mg of the modified exendin or exendin agonist of the invention is administered per day. More preferably, about 1-30 µg to about 2 mg, or about 1-30 µg to about 1 mg of the modified exendin or exendin agonist of the invention is administered per day. Most preferably, about 3 µg to about 500 µg of the modified exendin or exendin agonist of the invention is administered per day.

Preferred exendins or exendin agonists for modification and use include: exendin-4 (1-30) (SEQ ID NO:3 His Gly Glu Gly Thr Phe Thr Ser Asp Leu Ser Lys Gln Met Glu Glu Glu Ala Val Arg Leu Phe Ile Glu Trp Leu Lys Asn Gly Gly); exendin-4 (1-30) amide (SEQ ID NO:4 His Gly Glu Gly Thr Phe Thr Ser Asp Leu Ser Lys Gln Met Glu Glu Glu Ala Val Arg Leu Phe Ile Glu Trp Leu Lys Asn Gly Gly-$NH_2$); exendin-4 (1-28) amide (SEQ ID NO:5 His Gly Glu Gly Thr Phe Thr Ser Asp Leu Ser Lys Gln Met Glu Glu Glu Ala Val Arg Leu Phe Ile Glu Trp Leu Lys Asn-$NH_2$); $^{14}$Leu, $^{25}$Phe exendin-4 amide (SEQ ID NO:6 His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-$NH_2$); $^{14}$Leu, $^{25}$Phe exendin-4 (1-28) amide (SEQ ID NO:7 His Gly Glu Gly Thr Phe Thr Ser Asp Leu Ser Lys Gln Leu Glu Glu Glu Ala Val Arg Leu Phe Ile Glu Phe Leu Lys Asn-$NH_2$); and $^{14}$Leu, $^{22}$Ala, $^{25}$Phe exendin-4 (1-28) amide (SEQ ID NO:8 His Gly Glu Gly Thr Phe Thr Ser Asp Leu Ser Lys Gln Leu Glu Glu Glu Ala Val Arg Leu Ala Ile Glu Phe Leu Lys Asn-$NH_2$).

In the methods of the present invention, the modified exendins or exendin agonists may be administered separately or together with one or more other compounds and compositions that exhibit a long term or short-term satiety action, including, but not limited to other compounds and compositions that include an amylin agonist, cholecystokinin (CCK), or a leptin (ob protein). Suitable amylin agonists include, for example, [$^{25,28,29}$Pro-]-human amylin (also known as "pramlintide," and previously referred to as "AC-137") as described in U.S. Pat. No. 5,686,511, and salmon calcitonin. The CCK used is preferably CCK octopeptide (CCK-8). Leptin is discussed in, for example, Pelleymounter, M. A., et al. *Science* 269:540-43 (1995); Halaas, J. L., et al. *Science* 269:543-46 (1995); and Campfield, L. A., et al. *Eur. J. Pharmac.* 262:133-41 (1994).

The invention also provides compositions and methods for providing therapeutically effective amounts of the modified exendins or exendin agonists of the invention in order to increase urine flow in an individual, decrease the amount of potassium in the urine of an individual, prevent or alleviate a condition or disorder associated with hypervolemia or toxic hypervolemia in an individual, induce rapid diuresis, prepare an individual for a surgical procedure, increase renal plasma flow and glomerular filtration rates, or treat pre-eclampsia or eclampsia of pregnancy.

DEFINITIONS

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on 1-hydroxybenzotriazole monohydrate. "homoP" or "hPro" refers to homoproline. "MeAla" or "Nme" refers to N-methylalanine. "naph" refers to naphthylalanine. "pG" or pGly" refers to pentylglycine. "tBuG" refers to tertiary-butylglycine. "ThioP" or tPro" refers to thioproline. "3Hyp" refers to 3-hydroxyproline. "4Hyp" refers to 4-hydroxyproline. "NAG" refers to N-alkylglycine. "NAPG" refers to N-alkylpentylglycine. "Norval" refers to norvaline. "Norleu" refers to norleucine.

Other features and advantages of the invention will be apparent from the following description of the preferred embodiments thereof, and from the claims.

BRIEF DESCRIPTION OF THE DRAWINGS

FIG. 1 depicts the amino acid sequence for exendin-3 (SEQ ID NO: 1).

FIG. 2 depicts the amino acid sequence for exendin-4 (SEQ ID NO: 2).

FIG. 3 depicts the amino acid sequences for certain exendin agonist compounds useful in the present invention (SEQ ID NOs:9-25).

FIG. 4 depicts the amino acid sequences for certain compounds of the present invention, Compounds 1-174 (SEQ ID NOs:26-199).

DETAILED DESCRIPTION OF THE INVENTION

Figure 5:
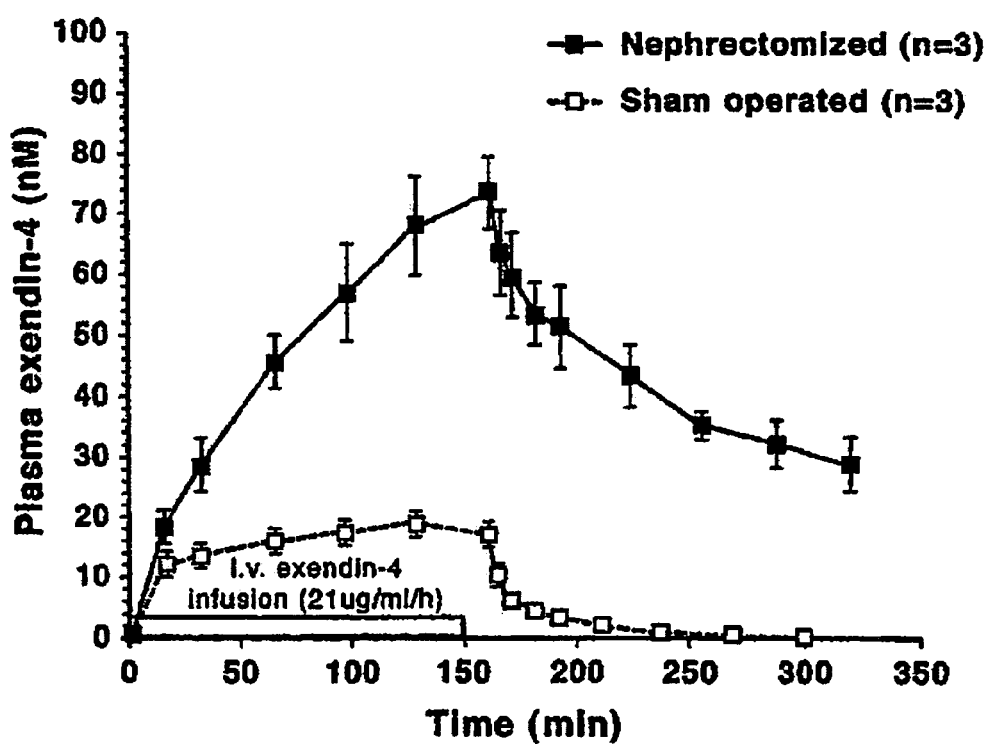
FIG. 5 is a graph showing the effect of functional nephrectomy on exendin-4 clearance.

The present invention relates to novel modified exendins and exendin agonists having an exendin or exendin agonist linked to one or more polyethylene glycol polymers, and related products and methods that are useful, for example, in the treatment of diabetes, including Type 1, Type 2, and gestational diabetes, in the treatment of disorders which would be benefited by agents which modulate plasma glucose levels or suppress glucagon secretion, and in the treatment of disorders which would be benefited by the administration of agents useful in modulating the rate of gastric emptying or food intake, including obesity, eating disorders, insulin-resistance syndrome, and triglyceride levels, and to treat subjects suffering from dyslipidemia. The methods are also useful for lowering plasma lipid levels, reducing cardiac risk, reducing appetite, and reducing the weight of subjects. Pharmaceutical compositions for use in the methods of the invention are also disclosed.

Modified Exendins And Exendin Agonists

The modified exendins and exendin agonists of the present invention include one or more PEG polymers linked to an exendin or exendin agonist, such as a naturally occurring exendin, a synthetic exendin or an exendin agonist.

Exendin-4

Exendin-4 is a naturally occurring peptide isolated from the salivary secretions of the Gila monster. Animal testing of exendin-4 has shown that its ability to lower blood glucose persists for several hours. Exendin-4, a 39-amino acid polypeptide, is synthesized using solid phase synthesis as described herein.

As described herein, the nonclinical pharmacology of exendin-4 has been studied. In the brain, exendin-4 binds principally to the area postrema and nucleus tractus solitarius region in the hindbrain and to the subfornical organ in the forebrain. Exendin-4 binding has been observed in the rat and mouse brain and kidney. The structures to which exendin-4 binds in the kidney are unknown.

Various experiments have compared the biologic actions of exendin-4 and GLP-1 and demonstrated a more favorable spectrum of properties for exendin-4. A single subcutaneous dose of exendin-4 lowered plasma glucose in db/db (diabetic) and ob/ob (diabetic obese) mice by up to 40%. In Diabetic Fatty Zucker (ZDF) rats, 5 weeks of treatment with exendin-4 lowered HbA, (a measure of glycosylated hemoglobin used to evaluate plasma glucose levels) by up to 41%. Insulin sensitivity was also improved by 76% following 5 weeks of treatment in obese ZDF rats. In glucose intolerant primates, dose-dependent decreases in plasma glucose were also observed.

An insulinotropic action of exendin-4 has also been observed in rodents, improving insulin response to glucose by over 100% in non-fasted Harlan Sprague Dawley (HSD) rats, and by up to ~10-fold in non-fasted db/db mice. Higher pretreatment plasma glucose concentrations were associated with greater glucose-lowering effects. Thus the observed glucose lowering effect of exendin-4 appears to be glucose-dependent, and minimal if animals are already euglycemic.

Exendin-4 dose dependently slowed gastric emptying in HSD rats and was ~90-fold more potent than GLP-1 for this action. Exendin-4 has also been shown to reduce food intake in NIH/Sw (Swiss) mice following peripheral administration, and was at least 1000 times more potent than GLP-1 for this action. Exendin-4 reduced plasma glucagon concentrations by approximately 40% in anesthetized ZDF rats during hyperinsulinemic, hyperglycemic clamp conditions, but did not affect plasma glucagon concentrations during euglycemic conditions in normal rats. Exendin-4 has been shown to dose-dependently reduce body weight in obese ZDF rats, while in lean ZDF rats, the observed decrease in body weight appears to be transient.

Through effects on augmenting and restoring insulin secretion, modified exendins or exendin agonists containing exendin-4, for example, will be useful in people with type 2 diabetes who retain the ability to secrete insulin. Its effects on food intake, gastric emptying, other mechanisms that modulate nutrient absorption, and glucagon secretion also support the utility of such modified exendins and exendin agonists containing exendin-4, for example, in the treatment of, for example, obesity, type 1 diabetes, and people with type 2 diabetes who have reduced insulin secretion.

The toxicology of exendin-4 has been investigated in single-dose studies in mice, rats and monkeys, repeated-dose (up to 28 consecutive daily doses) studies in rats and monkeys and in vitro tests for mutagenicity and chromosomal alterations. To date, no deaths have occurred, and there have been no observed treatment-related changes in hematology, clinical chemistry, or gross or microscopic tissue changes. Exendin-4 was demonstrated to be non-mutagenic, and did not cause chromosomal aberrations at the concentrations tested (up to 5000 μg/mL).

In support of the investigation of the nonclinical pharmacokinetics and metabolism of exendin-4, a number of immunoassays have been developed. A radioimmunoassay with limited sensitivity (~100 μM) was used in initial pharmacokinetic studies. A two-site IRMA assay for exendin-4 was subsequently validated with a lower limit of quantitation of 15 μM. The bioavailability of exendin-4, given subcutaneously, was found to be approximately 50-80% using the radioimmunoassay. This was similar to that seen following intraperitoneal administration (48-60%). Peak plasma concentrations ($C_{max}$) occurred between 30 and 43 minutes ($T_{max}$). Both $C_{max}$ and AUC values were monotonically related to dose. The apparent terminal half-life for exendin-4 given subcutaneously was approximately 90-110 minutes. This was significantly longer than the 14-41 minutes seen following intravenous dosing. Similar results were obtained using the IRMA assay. Degradation studies with exendin-4 compared to GLP-1 indicate that exendin-4 is relatively resistant to degradation.

Exendin Agonists

Exendin agonists include exendin peptide analogs in which one or more naturally occurring amino acids are eliminated or replaced with another amino acid(s). Preferred exendin agonists are agonist analogs of exendin-4. Particularly preferred exendin agonists are described in PCT/US98/16387 filed Aug. 6, 1998 (published as WO 99/07404), which claims the benefit of U.S. Patent Application Ser. No. 60/055,404, filed Aug. 8, 1997; PCT/US98/24210, filed Nov. 13, 1998 (published as WO 99/24210), which claims the benefit of U.S. Application No. 60/065,442 filed Nov. 14, 1997; and PCT/US98/24273, filed Nov. 13, 1998 (published as WO 99/25728), which claims the benefit of U.S. Application No. 60/066,029 filed Nov. 14, 1997, all of which are incorporated herein by reference in their entirety, including any drawings.

Activity as exendin agonists can be indicated, for example, by activity in the assays described below. Effects of exendins or exendin agonists on gastric motility and gastric emptying can be identified, evaluated, or screened for, using the methods described herein, or other art-known or equivalent methods for determining gastric motility. For example, see U.S. patent application Ser. No. 60/166,899, entitled, "High Affinity Exendin Receptor," filed Nov. 22, 1999. Negative receptor assays or screens for exendin agonist compounds or candidate exendin agonist compounds, such as an amylin receptor assay/screen using an amylin receptor preparation as described in U.S. Pat. No. 5,264,372, issued Nov. 23, 1993, the contents of which are incorporated herein by reference, one or more calcitonin receptor assays/screens using, for example, T47D and MCF7 breast carcinoma cells, which contain calcium receptors coupled to the stimulation of adenyl cyclase activity, and/or a CGRP receptor assay/screen using, for example, SK-N-MC cells.

One such method for use in identifying or evaluating the ability of a compound to slow gastric motility, involves: (a) bringing together a test sample and a test system, the test sample containing one or more test compounds, the test system containing a system for evaluating gastric motility, the system being characterized in that it exhibits, for example, elevated plasma glucose in response to the introduction to the system of glucose or a meal; and, (b) determining the presence or amount of a rise in plasma glucose in the system. Positive and/or negative controls may be used as well.

Also included within the scope of the present invention are pharmaceutically acceptable salts of the modified compounds of formula (I-VIII) and pharmaceutical compositions including said compounds and salts thereof.

Formula I

Exendin agonist compounds also include those described in U.S. Application No. 60/065,442 (see also WO 99/25727), including compounds of the formula (I) (SEQ ID NO: 200):

```
Xaa1 Xaa2 Xaa3 Gly Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28-Z1;
``` wherein
$Xaa_1$ is His, Arg or Tyr;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Ala, Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is OH,

```
                                    (SEQ ID NO: 201)
NH2

Gly-Z2,

Gly Gly-Z2,

Gly Gly Xaa31-Z2,

Gly Gly Xaa31 Ser-Z2,

Gly Gly Xaa31 Ser Ser-Z2,

Gly Gly Xaa31 Ser Ser Gly-Z2,

Gly Gly Xaa31 Ser Ser Gly Ala-Z2,

Gly Gly Xaa31 Ser Ser Gly Ala Xaa36-Z2,

Gly Gly Xaa31 Ser Ser Gly Ala Xaa36 Xaa37-Z2
or

Gly Gly Xaa31 Ser Ser Gly Ala Xaa36 Xaa37

Xaa38-Z2;
```

$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is OH or $NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_{14}$ is Leu, pentylglycine or Met.

Preferred compounds are those wherein $Xaa_{25}$ is Trp or Phe.

Preferred compounds are those where $Xaa_6$ is Phe or naphthylalanine; $Xaa_{22}$ is Phe or naphthylalanine and $Xaa_{23}$ is Ile or Val.

Preferred are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.
Preferably $Z_2$ is —$NH_2$.

According to one aspect, preferred are compounds of formula (I) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to an especially preferred aspect, especially preferred compounds include those of formula (I) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or naphthylalanine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_1$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Especially preferred compounds include those set forth in PCT/US98/24210, filed Nov. 13, 1998, (published as WO 99/25727) identified therein as compounds 2-23.

According to an especially preferred aspect, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative degradation, both in vitro and in vivo, as well as during synthesis of the compound.

Formula II

Exendin agonist compounds also include those described in U.S. Application No. 60/066,029 (see also WO 99/25728), including compounds of the formula (II) (SEQ ID NO: 202):

```
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28-Z1;
``` wherein
$Xaa_1$ is His, Arg, Tyr, Ala, Norval, Val or Norleu;
$Xaa_2$ is Ser, Gly, Ala or Thr;
$Xaa_3$ is Ala, Asp or Glu;
$Xaa_4$ is Ala, Norval, Val, Norleu or Gly;
$Xaa_5$ is Ala or Thr;
$Xaa_6$ is Phe, Tyr or naphthylalanine;
$Xaa_7$ is Thr or Ser;
$Xaa_8$ is Ala, Ser or Thr;
$Xaa_9$ is Ala, Norval, Val, Norleu, Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is OH,

```
                                        (SEQ ID NO: 203)
NH2,

Gly-Z2,

Gly Gly-Z2,

Gly Gly Xaa31-Z2,

Gly Gly Xaa31 Ser-Z2,

Gly Gly Xaa31 Ser Ser-Z2,

Gly Gly Xaa31 Ser Ser Gly-Z2,

Gly Gly Xaa31 Ser Ser Gly Ala-Z2,

Gly Gly Xaa31 Ser Ser Gly Ala Xaa36-Z2,

Gly Gly Xaa31 Ser Ser Gly Ala Xaa36 Xaa37-Z2,

Gly Gly Xaa31 Ser Ser Gly Ala Xaa36 Xaa37 Xaa38-Z2
or

Gly Gly Xaa31 Ser Ser Gly Ala Xaa36 Xaa37 Xaa38

Xaa39-Z2;
``` wherein $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is OH or $NH_2$;

provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (II) include those described in application Serial No. PCT/US98/24273, filed Nov. 13, 1998 (published as WO 99/25728), identified therein in Examples 1-89 ("Compounds 1-89," respectively), as well as those corresponding compounds identified therein in Examples 104 and 105.

Preferred such exendin agonist compounds include those wherein $Xaa_1$ is His, Ala or Norval. More preferably $Xaa_1$ is His or Ala. Most preferably $Xaa_1$ is His.

Preferred are those compounds of formula (II) wherein $Xaa_2$ is Gly.

Preferred are those compounds of formula (II) wherein $Xaa_3$ is Ala.

Preferred are those compounds of formula (II) wherein $Xaa_4$ is Ala.

Preferred are those compounds of formula (II) wherein $Xaa_9$ is Ala.

Preferred are those compounds of formula (II) wherein $Xaa_{14}$ is Leu, pentylglycine or Met.

Preferred compounds of formula (II) are those wherein $Xaa_{25}$ is Trp or Phe.

Preferred compounds of formula (II) are those where $Xaa_6$ is Ala, Phe or naphthylalanine; $Xaa_{22}$ is Phe or naphthylalanine; and $Xaa_{23}$ is Ile or Val.

Preferred are compounds of formula (II) wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.
Preferably $Z_2$ is —$NH_2$.

According to one aspect, preferred are compounds of formula (II) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably $Z_1$ is —$NH_2$.

According to an especially preferred aspect, especially preferred compounds include those of formula (II) wherein: $Xaa_1$ is His or Ala; $Xaa_2$ is Gly or Ala; $Xaa_3$ is Ala, Asp or Glu; $Xaa_4$ is Ala or Gly; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{11}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala. Especially preferred compounds of formula (II) include those described in application Serial No. PCT/US98/24273, filed Nov. 13, 1998 (published as WO 99/25728) as having the amino acid sequence of SEQ ID NOs:5-93 therein.

According to an especially preferred aspect, provided are compounds of formula (II) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degradation, both in vitro and in vivo, as well as during synthesis of the compound.

Formula III

Also within the scope of the present invention are narrower genera of compounds having peptides of various lengths, for example genera of compounds which do not include peptides having a length of 28, 29 or 30 amino acid residues, respectively. Additionally, the present invention includes narrower genera of compounds described in PCT application Serial No. PCT/US98/24210, filed Nov. 13, 1998 (published as WO 99/25727) and having particular amino acid sequences, for example, compounds of the formula (III) (SEQ ID NO: 204):

Xaa$_1$ Xaa$_2$ Xaa$_3$ Gly Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala Xaa$_{18}$

Xaa$_{19}$ Xaa$_{20}$ Xaa$_{21}$ Xaa$_{22}$ Xaa$_{23}$ Xaa$_{24}$ Xaa$_{25}$ Xaa$_{26}$

Xaa$_{27}$ Xaa$_{28}$-Z$_1$;

wherein
Xaa$_1$ is His or Arg;
Xaa$_2$ is Gly or Ala;
Xaa$_3$ is Asp or Glu;
Xaa$_5$ is Ala or Thr;
Xaa$_6$ is Ala, Phe or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu or pentylglycine;
Xaa$_{11}$ is Ala or Ser;
Xaa$_{12}$ is Ala or Lys;
Xaa$_{13}$ is Ala or Gln;
Xaa$_{14}$ is Ala, Leu or pentylglycine;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe or naphthylalanine;
Xaa$_{23}$ is Ile, Val or tert-butylglycine;
Xaa$_{24}$ is Ala, Glu or Asp;
Xaa$_{25}$ is Ala, Trp, or Phe;
Xaa$_{26}$ is Ala or Leu;
Xaa$_{27}$ is Ala or Lys;
Xaa$_{28}$ is Ala or Asn;
Z$_1$ is OH,

NH$_2$,

Gly-Z$_2$,

Gly Gly -Z$_2$,

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$ or

Gly Gly Xaa$_{31}$ Ser Ser Gly Ala Xaa$_{36}$ Xaa$_{37}$ Xaa$_{38}$-Z$_2$;

wherein Xaa$_{31}$, Xaa$_{36}$, Xaa$_{37}$ and Xaa$_{38}$ are independently selected from the group
consisting of Pro, homoproline, thioproline and N-methylalanine; and Z$_2$ is OH or NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and pharmaceutically acceptable salts thereof.

Formula IV

Additionally, the present invention includes narrower genera of peptide compounds described in PCT Application Serial No. PCT/US98/24273, filed Nov. 13, 1998 (published as WO 99/25728) as having particular amino acid sequences, for example, compounds of the formula IV (SEQ ID NO: 205):

Xaa$_1$ Xaa$_2$ Xaa$_3$ Xaa$_5$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{18}$ Xaa$_{19}$ Xaa$_{20}$ Xaa$_{21}$ Xaa$_{22}$ Xaa$_{23}$ Xaa$_{24}$ Xaa$_{25}$

Xaa$_{26}$ Xaa$_{27}$ Xaa$_{28}$-Z$_1$;

wherein
Xaa$_1$ is His or Ala;
Xaa$_2$ is Gly or Ala;
Xaa$_3$ is Ala, Asp or Glu;
Xaa$_4$ is Ala or Gly;
Xaa$_5$ is Ala or Thr;
Xaa$_6$ is Phe or naphthylalanine;
Xaa$_7$ is Thr or Ser;
Xaa$_8$ is Ala, Ser or Thr;
Xaa$_9$ is Ala, Asp or Glu;

$Xaa_{10}$ is Ala, Leu or pentylglycine;
$Xaa_{11}$ is Ala or Ser;
$Xaa_{12}$ is Ala or Lys;
$Xaa_{13}$ is Ala or Gln;
$Xaa_{14}$ is Ala, Leu, Met or pentylglycine;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe or naphthylalanine;
$Xaa_{23}$ is Ile, Val or tert-butylglycine;
$Xaa_{24}$ is Ala, Glu or Asp;
$Xaa_{25}$ is Ala, Trp or Phe;
$Xaa_{26}$ is Ala or Leu;
$Xaa_{27}$ is Ala or Lys;
$Xaa_{28}$ is Ala or Asn;
$Z_1$ is OH, (SEQ ID NO: 206):
$NH_2$, $Gly-Z_2$, $Gly\ Gly-Z_2$ $Gly\ Gly\ Xaa_{31}-Z_2$, $Gly\ Gly\ Xaa_{31}\ Ser-Z_2$, $Gly\ Gly\ Xaa_{31}\ Ser\ Ser-Z_2$, $Gly\ Gly\ Xaa_{31}\ Ser\ Ser\ Gly-Z_2$, $Gly\ Gly\ Xaa_{31}\ Ser\ Ser\ Gly\ Ala-Z_2$, $Gly\ Gly\ Xaa_{31}\ Ser\ Ser\ Gly\ Ala\ Xaa_{36}-Z_2$, $Gly\ Gly\ Xaa_{31}\ Ser\ Ser\ Gly\ Ala\ Xaa_{36}\ Xaa_{37}-Z_2$ $Gly\ Gly\ Xaa_{31}\ Ser\ Ser\ Gly\ Ala\ Xaa_{36}\ Xaa_{37}\ Xaa_{38}-Z_2$ $Gly\ Gly\ Xaa_{31}\ Ser\ Ser\ Gly\ Ala\ Xaa_{36}\ Xaa_{37}\ Xaa_{38}$ $Ser-Z_2$;

wherein $Xaa_{31}$, $Xaa_{36}$, $Xaa_{37}$ and $Xaa_{38}$ are independently Pro, homoproline, thioproline, or N-methylylalanine; and $Z_2$ is OH or $NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and provided that, if $Xaa_1$ is His, Arg or Tyr, then at least one of $Xaa_3$, $Xaa_4$ and $Xaa_9$ is Ala; and pharmaceutically acceptable salts thereof.

Preferred compounds of formula (IV) include those wherein $Xaa_1$ is His, Ala, Norval or 4-imidazopropionyl. Preferably, $Xaa_1$ is His, or 4-imidazopropionyl or Ala, more preferably His or 4-imidazopropionyl.

Preferred compounds of formula (IV) include those wherein $Xaa_2$ is Gly.

Preferred compounds of formula (IV) include those wherein $Xaa_4$ is Ala.

Preferred compounds of formula (IV) include those wherein $Xaa_9$ is Ala.

Preferred compounds of formula (IV) include those wherein $Xaa_{14}$ is Leu, pentylglycine or Met.

Preferred compounds of formula (IV) include those wherein $Xaa_{25}$ is Trp or Phe.

Preferred compounds of formula (IV) include those wherein $Xaa_6$ is Ala, Phe or naphthylalanine; $Xaa_{22}$ is Phe or naphthylalanine; and $Xaa_{23}$ is Ile or Val.

Preferred compounds of formula (IV) include those wherein $Z_1$ is $—NH_2$.

Preferred compounds of formula (IV) include those wherein $Xaa_{31}$, $Xaa_{36}$, $Xaa_{37}$ and $Xaa_{38}$ are independently selected from the group consisting of Pro, homoproline, thioproline and N-alkylalanine.

Preferred compounds of formula (IV) include those wherein $Xaa_{39}$ is Ser or Tyr, preferably Ser. Preferred compounds of formula (IV) include those wherein $Z_2$ is $—NH_2$.

Preferred compounds of formula (IV) include those wherein $Z_1$ is $—NH_2$.

Preferred compounds of formula (IV) include those wherein $Xaa_{21}$ is Lys-$NH^\epsilon$—R where R is Lys, Arg, $C_1$-$C_{10}$ straight chain or branched alkanoyl.

Preferred compounds of formula (IV) include those wherein $X_1$ is Lys Asn, Lys-$NH^\epsilon$—R Asn, or Lys-$NH^\epsilon$—R Ala where R is Lys, Arg, $C_1$-$C_{10}$ straight chain or branched alkanoyl. Preferred compounds of formula (IV) include those having an amino acid sequence described in PCT application Serial No. PCT/US98/24273, filed Nov. 13, 1998 (published as WO 99/25728) as being selected from SEQ ID NOs:95-110 therein.

Formula V

Also provided are compounds described in PCT application PCT/US98/24210, filed Nov. 13, 1998 (published as WO 99/25727) including compounds of the formula V (SEQ ID NO: 207):

$Xaa_1\ Xaa_2\ Xaa_3\ Gly\ Xaa_5\ Xaa_6\ Xaa_7\ Xaa_8\ Xaa_9\ Xaa_{10}$ $Xaa_{11}\ Xaa_{12}\ Xaa_{13}\ Xaa_{14}\ Xaa_{15}\ Xaa_{16}\ Xaa_{17}\ Ala$ $Xaa_{19}\ Xaa_{20}\ Xaa_{21}\ Xaa_{22}\ Xaa_{23}\ Xaa_{24}\ Xaa_{25}\ Xaa_{26}$ $X_1$-$Z_1$;

wherein
$Xaa_1$ is His, Arg or Tyr or 4-imidazopropionyl;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala, Leu or Lys-$NH^\epsilon$—R where R is Lys, Arg, $C_1$-$C_{10}$ straight chain or branched alkanoyl or cycloalkylalkanoyl;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;

$X_1$ is Lys Asn, Asn Lys, Lys-NH$^\epsilon$—R Asn, Asn Lys-NH$^\epsilon$—R, Lys-NH$^\epsilon$—R Ala, Ala Lys-NH$^\epsilon$—R where R is Lys, Arg, $C_1$-$C_{10}$ straight chain or branched alkanoyl or cycloalkylalkanoyl $Z_1$ is OH,

```
NH2,

Gly-Z2,

Gly Gly-Z2,

Gly Gly Xaa31-Z2,

Gly Gly Xaa31 Ser-Z2,

Gly Gly Xaa31 Ser Ser-Z2,

Gly Gly Xaa31 Ser Ser Gly-Z2,

Gly Gly Xaa31 Ser Ser Gly Ala-Z2,

Gly Gly Xaa31 Ser Ser Gly Ala Xaa36-Z2,

Gly Gly Xaa31 Ser Ser Gly Ala Xaa36 Xaa37-Z2
or

Gly Gly Xaa31 Ser Ser Gly Ala Xaa36 Xaa37

Xaa38-Z2;
``` wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; and $Z_2$ is OH or NH$_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, and $Xaa_{26}$ are Ala. Also within the scope of the present invention are pharmaceutically acceptable salts of the compound of formula (V) and pharmaceutical compositions including said compounds and salts thereof.

Preferred exendin agonist compounds of formula (V) include those wherein $Xaa_1$ is His, Tyr or 4-imidazopropionyl. More preferably $Xaa_1$ is His.

Preferred are those compounds of formula (V) wherein $Xaa_1$ is 4-imidazopropionyl. Preferred are those compounds of formula (V) wherein $Xaa_2$ is Gly.

Preferred compounds of formula (V) are those wherein $Xaa_{14}$ is Leu, pentylglycine or Met.

Preferred compounds of formula (V) are those wherein $Xaa_{25}$ is Trp or Phe.

According to one aspect, preferred are compounds of formula (V) wherein $Xaa_6$ is Phe or naphthylalanine; and $Xaa_{22}$ is Phe or naphthylalanine; and $Xaa_{23}$ is Ile or Val. More preferably, $Z_1$ is —NH$_2$. According to one aspect, especially preferred are such compounds of formula (V) wherein $Xaa_{31}$, $Xaa_{36}$, $Xaa_{37}$ and $Xaa_{38}$ are independently selected from the group consisting of Pro, homoproline, thioproline and N-alkylalanine. More preferred, $Z_2$ is —NH$_2$.

Preferred compounds of formula (V) include those wherein $X_1$ is Lys Asn, Lys-NH$^\epsilon$—R Asn, or Lys-NH$^\epsilon$—R Ala where R is Lys, Arg, $C_1$-$C_{10}$ straight chain or branched alkanoyl.

Preferred compounds of formula (V) include compounds described in PCT/US98/24210, filed Nov. 13, 1998 (published as WO 99/25727) and identified therein as Compound Nos. 62-69.

Preferred such exendin agonist compounds include those wherein $Xaa_1$ is His, Ala or Norval. More preferably $Xaa_1$ is His or Ala. Most preferably $Xaa_1$ is His.

Preferred are those compounds of formula (V) wherein $Xaa_2$ is Gly.

Preferred are those compounds of formula (V) wherein $Xaa_3$ is Ala.

Preferred are those compounds of formula (V) wherein $Xaa_4$ is Ala.

Preferred are those compounds of formula (V) wherein $Xaa_9$ is Ala.

Preferred are those compounds of formula (V) wherein $Xaa_{14}$ is Leu, pentylglycine or Met.

Preferred compounds of formula (V) are those wherein $Xaa_{25}$ is Trp or Phe.

Preferred compounds of formula (V) are those where $Xaa_6$ is Ala, Phe or naphthylalanine; $Xaa_{22}$ is Phe or naphthylalanine; and $Xaa_{23}$ is Ile or Val.

Preferred are compounds of formula (V) wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —NH$_2$.
Preferably $Z_2$ is —NH$_2$.

According to one aspect, preferred are compounds of formula (V) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably $Z_1$ is —NH$_2$.

According to an especially preferred aspect, especially preferred compounds include those of formula (V) wherein: $Xaa_1$ is His or Ala; $Xaa_2$ is Gly or Ala; $Xaa_3$ is Ala, Asp or Glu; $Xaa_4$ is Ala or Gly; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala. Especially preferred compounds of formula (V) include those described in PCT application Serial No. PCT/US98/24210, filed Nov. 13, 1998 (published as WO 99/25727) and having the amino acid sequences identified therein as SEQ ID NOs:5-93.

According to an especially preferred aspect, provided are compounds of formula (V) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degradation, both in vitro and in vivo, as well as during synthesis of the compound.

Formula VI

Also provided are peptide compounds described in PCT Application Serial No. PCT/US98/24273, filed Nov. 13, 1998 (published as WO 99/25728), including compounds of the formula (VI) (SEQ ID NO: 208):

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

X$_1$-Z$_1$;

wherein

Xaa$_1$ is His, Arg, Tyr, Ala, Norval, Val, Norleu or 4-imidazopropionyl;
Xaa$_2$ is Ser, Gly, Ala or Thr;
Xaa$_3$ is Ala, Asp or Glu;
Xaa$_4$ is Ala, Norval, Val, Norleu or Gly;
Xaa$_5$ is Ala or Thr;
Xaa$_6$ is Phe, Tyr or naphthylalanine;
Xaa$_7$ is Thr or Ser;
Xaa$_8$ is Ala, Ser or Thr;
Xaa$_9$ is Ala, Norval, Val, Norleu, Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala, Leu or Lys-NH$^\epsilon$—R where R is Lys, Arg, C$^{1-10}$ straight chain or branched alkanoyl or cycloalleyl-alkanoyl;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
X$_1$ is Lys Asn, Asn Lys, Lys-NH$^\epsilon$—R Asn, Asn Lys-NH$^\epsilon$—R, Lys-NH$^\epsilon$—R Ala, Ala Lys-NH$^\epsilon$—R where R is Lys, Arg, C$_1$-C$_{10}$ straight chain or branched alkanoyl or cycloalkylalkanoyl Z$_1$ is OH,

NH$_2$,

Gly-Z$_2$,

Gly Gly-Z$_2$,

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$,

Gly Gly Xaa$_{31}$ Ser Ser Gly Ala Xaa$_{36}$ Xaa$_{37}$ Xaa$_{38}$-Z$_2$ or

Gly Gly Xaa$_{31}$ Ser Ser Gly Ala Xaa$_{36}$ Xaa$_{37}$ Xaa$_{38}$

Xaa$_{39}$-Z$_2$;

wherein Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; and Z$_2$ is OH or NH$_2$;

provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, are Ala; and provided also that, if Xaa$_1$ is His, Arg, Tyr, or 4-imidazopropionyl then at least one of Xaa$_3$, Xaa$_4$ and Xaa$_9$ is Ala.

Preferred compounds of formula (VI) include those wherein Xaa$_1$ is His, Ala, Norval or 4-imidazopropionyl. Preferably, Xaa$_1$ is His, or 4-imidazopropionyl or Ala, more preferably His or 4-imidazopropionyl.

Preferred compounds of formula (VI) include those wherein Xaa$_2$ is Gly.

Preferred compounds of formula (VI) include those wherein Xaa$_4$ is Ala.

Preferred compounds of formula (VI) include those wherein Xaa$_9$ is Ala.

Preferred compounds of formula (VI) include those wherein Xaa$_{14}$ is Leu, pentylglycine or Met.

Preferred compounds of formula (VI) include those wherein Xaa$_{25}$ is Trp or Phe.

Preferred compounds of formula (VI) include those wherein Xaa$_6$ is Ala, Phe or naphthylalanine; Xaa$_{22}$ is Phe or naphthylalanine; and Xaa$_{23}$ is Ile or Val.

Preferred compounds of formula (VI) include those wherein Z$_1$ is —NH$_2$.

Preferred compounds of formula (VI) include those wherein Xaa$_{31}$, Xaa$_{36}$, Xaa$_{37}$ and Xaa$_{38}$ are independently selected from the group consisting of Pro, homoproline, thioproline and N-alkylalanine.

Preferred compounds of formula (VI) include those wherein Xaa$_{39}$ is Ser or Tyr, preferably Ser. Preferred compounds of formula (VI) include those wherein Z$_2$ is —NH$_2$.

Preferred compounds of formula (VI) include those 42 wherein Z$_1$ is —NH$_2$.

Preferred compounds of formula (VI) include those wherein Xaa$_{21}$ is Lys-NH$^\epsilon$—R where R is Lys, Arg, C$_1$-C$_{10}$ straight chain or branched alkanoyl.

Preferred compounds of formula (VI) include those wherein X$_1$ is Lys Asn, Lys-NH$^\epsilon$—R Asn, or Lys-NH$^\epsilon$—R Ala where R is Lys, Arg, C$_1$-C$_{10}$ straight chain or branched alkanoyl.

Preferred compounds of formula (VI) include those described in PCT Application Serial No. PCT/US98/24273, filed Nov. 13, 1998 (published as WO 99/25728) as having an amino acid sequence selected from those identified therein as SEQ ID NOs:95-110.

Formula VII

Compounds particularly useful according to the present invention are exendin agonist compounds described in U.S. application Ser. No. 09/003,869, filed Jan. 7, 1998 (published as U.S. Pat. No. 5,956,026 and WO 98/30231), including compounds of the formula (VII) (SEQ ID NO: 209):

```
Xaa₁ Xaa₂ Xaa₃ Gly Thr Xaa₄ Xaa₅ Xaa₆ Xaa₇ Xaa₈

Ser Lys Gln Xaa₉ Glu Glu Glu Ala Val Arg Leu

Xaa₁₀ Xaa₁₁ Xaa₁₂ Xaa₁₃ Leu Lys Asn Gly Gly Xaa₁₄

Ser Ser Gly Ala Xaa₁₅ Xaa₁₆ Xaa₁₇ Xaa₁₈-Z
``` wherein $Xaa_1$ is His, Arg or Tyr; $Xaa_2$ is Ser, Gly, Ala or Thr; $Xaa_3$ is Asp or Glu; $Xaa_4$ is Phe, Tyr or naphthalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —NH₂; with the proviso that the compound does not have the formula of either SEQ ID NOs 1 or 2. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds include those having amino acid sequences of SEQ ID NOs: 10 to 40. Also useful in the present invention are pharmaceutically acceptable salts of the compounds of formula (VII).

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_9$ is Leu, pentylglycine or Met.

Preferred compounds include those wherein $Xaa_{13}$ is Trp or Phe.

Also preferred are compounds where $Xaa_4$ is Phe or naphthalanine; $Xaa_1$ is Ile or Val and $Xaa_{14}$, $Xaa_{15}$, $Xaa_{16}$ and $Xaa_{17}$ are independently selected from Pro, homoproline, thioproline or N-alkylalanine. Preferably N-alkylalanine has a N-alkyl group of 1 to about 6 carbon atoms.

According to an especially preferred aspect, $Xaa_{15}$, $Xaa_{16}$ and $Xaa_{17}$ are the same amino acid reside.

Preferred are compounds wherein $Xaa_{18}$ is Ser or Tyr, more preferably Ser.

Preferably Z is —NH₂.

According to one aspect, preferred are compounds of formula (VII) wherein $Xaa_1$ is His or Tyr, more preferably His; $Xaa_2$ is Gly; $Xaa_4$ is Phe or naphthalanine; $Xaa_9$ is Leu, pentylglycine or Met; $Xaa_{10}$ is Phe or naphthalanine; $Xaa_{11}$ is Ile or Val; $Xaa_{14}$, $Xaa_{15}$, $Xaa_{16}$ and $Xaa_{17}$ are independently selected from Pro, homoproline, thioproline or N-alkylalanine; and $Xaa_{18}$ is Ser or Tyr, more preferably Ser. More preferably Z is —NH₂.

According to an especially preferred aspect, especially preferred compounds include those of formula (VII) wherein: $Xaa_1$ is His or Arg; $Xaa_2$ is Gly; $Xaa_3$ is Asp or Glu; $Xaa_4$ is Phe or napthylalanine; $Xaa_5$ is Thr or Ser; $Xaa_6$ is Ser or Thr; $Xaa_7$ is Asp or Glu; $Xaa_8$ is Leu or pentylglycine; $Xaa_9$ is Leu or pentylglycine; $Xaa_{10}$ is Phe or naphthalanine; $Xaa_1$ is Ile, Val or t-butylglycine; $Xaa_{12}$ is Glu or Asp; $Xaa_{13}$ is Trp or Phe; $Xaa_{14}$, $Xaa_{15}$, $Xaa_{16}$, and $Xaa_{17}$ are independently Pro, homoproline, thioproline, or N-methylalanine; $Xaa_{18}$ is Ser or Tyr: and Z is OH or NH₂; with the proviso that the compound does not have the formula of either SEQ. ID. NOS. 1 or 2. More preferably Z is —NH₂. Especially preferred compounds include those having the amino acid sequence of SEQ ID NOs:10, 11, 22, 23, 24, 27, 29, 36, 37 and 40.

According to an especially preferred aspect, provided are compounds where $Xaa_9$ is Leu, Ile, Val or pentylglycine, more preferably Leu or pentylglycine, and $Xaa_{13}$ is Phe, Tyr or naphthylalanine, more preferably Phe or naphthylalanine. These compounds are believed to exhibit advantageous duration of action and to be less subject to oxidative degradation, both in vitro and in vivo, as well as during synthesis of the compound.

Formula VIII

Also provided are compounds described in PCT/US98/16387, filed Aug. 6, 1998 (published as WO 99/07404), including compounds of the formula (VIII) (SEQ ID NO: 210):

```
Xaa₁ Xaa₂ Xaa₃ Gly Thr Xaa₄ Xaa₅ Xaa₆ Xaa₇ Xaa₈

Ser Lys Gln Xaa₉ Glu Glu Glu Ala Val Arg Leu

Xaa₁₀ Xaa₁₁ Xaa₁₂ Xaa₁₃ Leu X₁ Gly Gly Xaa₁₄

Ser Ser Gly Ala Xaa₁₅ Xaa₁₆ Xaa₁₇ Xaa₁₈-Z;
``` wherein $Xaa_1$ is His, Arg, Tyr or 4-imidazopropionyl; $Xaa_2$ is Ser, Gly, Ala or Thr; $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $X_1$ is Lys Asn, Asn Lys, Lys-NH$^\epsilon$—R Asn, Asn Lys-NH$^\epsilon$—R where R is Lys, Arg, $C_1$-$C_{10}$ straight chain or branched alkanoyl or cycloalkylalkanoyl; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —NH₂; with the proviso that the compound does not have the formula of either SEQ ID NOs 1 or 2. Suitable compounds of formula (VIII) include compounds described in PCT/US98/16387, filed Aug. 6, 1998 (published as WO 99/07404), having the amino acid sequences of SEQ ID NOs: 37-40 therein.

Preferred exendin agonist compounds of formula (VIII) include those wherein $Xaa_1$ is His, Tyr or 4-imidazopropionyl. More preferably, $Xaa_1$ is His or 4-imidazopropionyl.

Preferred are those compounds of formula (VIII) wherein $Xaa_2$ is Gly.

Preferred are those compounds of formula (VIII) wherein $Xaa_9$ is Leu, pentylglycine or Met.

Preferred are those compounds of formula (VIII) wherein $Xaa_{13}$ is Trp or Phe.

Preferred are those compounds of formula (VIII) wherein $X_1$ is Lys Asn, or Lys-NH$^\epsilon$—R Asn, where R is Lys, Arg, $C_1$-$C_{10}$ straight chain or branched alkanoyl.

Also preferred are compounds of formula (VIII) wherein $Xaa_4$ is Phe or naphthylalanine; $Xaa_{10}$ is Phe or naphthylalanine; $Xaa_{11}$ is Ile or Val and $Xaa_{14}$, $Xaa_{15}$, $Xaa_{16}$ and $Xaa_{17}$ are independently selected from Pro, homoproline, thioproline or N-alkylalanine. According to an especially preferred aspect, $Xaa_{18}$ is Ser or Tyr. Preferred are those such compounds wherein $Xaa_{18}$ is Ser. Preferably, Z is —NH₂.

According to one preferred aspect, preferred are compounds of formula (VIII) wherein $Xaa_4$ is Phe or naphthylalanine; $Xaa_{10}$ is Phe or naphthylalanine; $Xaa_{11}$ is Ile or Val, $X_1$ is Lys Asn, or Lys-NH$^\epsilon$—R Asn, where R is Lys, Arg, $C_1$-$C_{10}$ straight chain or branched alkanoyl and $Xaa_{14}$, $Xaa_{15}$, $Xaa_{16}$ and $Xaa_{17}$ are independently selected from Pro, homoproline, thioproline or N-alkylalanine.

Preparation of Modified Exendins and Exendin Agonists

The modified exendins and exendin agonists of the present invention may be made by linking one or more polyethylene glycol polymers or other molecular weight increasing agents to an exendin or exendin agonist. The synthesis of exendins and exendin agonists is thus described first, followed by methodology for linking the polyethylene glycol polymer(s) to the exendin or exendin agonist.

Preparation of Exendins and Exendin Agonists

Exendins and exendin agonist compounds such as exendin analogs and exendin derivatives, described herein may be prepared through peptide purification as described in, for example, Eng, et al., *J. Biol. Chem.* 265:20259-62, 1990; and Eng, et al., *J. Biol. Chem.* 267:7402-05, 1992, hereby incorporated by reference herein. Alternatively, exendins and exendin agonist peptides may be prepared by methods known to those skilled in the art, for example, as described in Raufman, et al., *J. Biol. Chem.* 267:21432-37, 1992, hereby incorporated by reference herein, using standard solid-phase peptide synthesis techniques and preferably an automated or semiautomated peptide synthesizer. The compounds that constitute active ingredients of the formulations and dosages of the present invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side chain-protected amino acids may be purchased from Applied Biosystems, Inc.: BSD-112344.1-Arg (Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His (Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−50° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6-12). Peptides may also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., *The Pico Tag Method: A Manual of Advanced Techniques for Amino Acid Analysis*, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Peptide active ingredient compounds useful in the formulations and dosages of the invention may also be prepared using recombinant DNA techniques, using methods now known in the art. See, e.g., Sambrook et al, *Molecular Cloning: A Laboratory Manual,* 2d Ed., Cold Spring Harbor (1989). Alternatively, such compounds may be prepared by homogeneous phase peptide synthesis methods. Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356-377 (1986).

Conjugation of Polyethylene Glycol Polymers (or Other Molecular Weight Increasing Agents)

There are several strategies for coupling PEG to peptides/proteins. See, Francis et al, *Int. J. Hematology* 68:1 (1998); Gombotz et al, *Bioconjugate Chem.* 6:150 (1995); and Delgado et al, *Crit. Rev. Therap. Drug Carrier Sys.* 9:249 (1992), all of which are incorporated herein by reference in their entirety. Those skilled in the art, therefore, will be able to utilize such well known techniques for linking one or more polyethylene glycol polymers to the exendins and exendin agonists described herein. Suitable polyethylene glycol polymers typically are commercially available or may be made by techniques well known to those skilled in the art. The polyethylene glycol polymers or other molecular weight increasing agents preferably have molecular weights between 500 and 20,000 and may be branched or straight chain polymers.

The attachment of a PEG on an intact peptide or protein can be accomplished by coupling to amino, carboxyl or thiol groups. These groups will typically be the N and C termini and on the side chains of such naturally occurring amino acids as lysine, aspartic acid, glutamic acid and cysteine. Since exendin-4 and other exendins and exendin agonists can be prepared by solid phase peptide chemistry techniques, a variety of moieties containing diamino and dicarboxylic groups with orthogonal protecting groups can be introduced for conjugation to PEG.

The present invention also provides for conjugation of an exendin or exendin agonist to one or more polymers other than polyethylene glycol which can regulate kidney clearance in a manner similar to polyethylene glycol. Examples of such polymers include albumin and gelatin. See, Gombotz and Pettit, *Bioconjugate Chem.*, 6:332-351, 1995, which is incorporated herein by reference in its entirety.

Utility

The formulations and dosages described herein are useful in view of their pharmacological properties. In particular, the compounds of the invention possess activity as agents to reduce food intake and as agents to regulate gastric motility and to slow gastric emptying, as evidenced by the ability to inhibit gastric emptying levels in mammals. They can be used to treat conditions or diseases which can be alleviated by reducing food intake or regulating gastric motility. The formulations and dosages of the invention are also effective as exendins and exendin agonists, and possess activity as agents to lower blood glucose, and to regulate gastric motility and to slow gastric emptying, as evidenced by the ability to reduce post-prandial glucose levels in mammals. The compounds of the present invention are useful in in vitro and in vivo scientific methods for investigation of exendins and exendin agonists for example in methods such as those described herein.

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Formulation and Administration

Modified exendin and exendin agonist formulations and dosages of the invention are useful in view of their exendin-like effects, and may conveniently be provided in the form of formulations suitable for parenteral (including intravenous, intramuscular and subcutaneous) administration. Also described herein are formulations and dosages useful in alternative delivery routes, including oral, nasal, buccal, sublingual and pulmonary.

The feasibility of alternate routes of delivery for exendin-4 has been explored by measuring exendin-4 in the circulation in conjunction with observation of a biologic response, such as plasma glucose lowering in diabetic animals, after administration. Passage of exendin-4 has been investigated across several surfaces, the respiratory tract (nasal, tracheal and pulmonary routes) and the gut (sublingual, gavage and intraduodenal routes). Biologic effect and appearance of exendin-4 in blood have been observed with each route of administration via the respiratory tract, and with sublingual and gavaged peptide via the gastrointestinal tract. Intra-tracheal administration, nasal administration, administration via the gut, and sublingual administration have all been described.

In some cases, it will be convenient to provide a modified exendin or exendin agonist and another anti-gastric-emptying agent, such as glucagon, an amylin, or an amylin agonist, in a single composition or solution for administration together. In other cases, it may be more advantageous to administer another anti-emptying agent separately from the modified exendin or exendin agonist. In yet other cases, it may be beneficial to provide a modified exendin or exendin agonist either co-formulated or separately with other glucose lowering agents such as insulin. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2 S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 4.0 to about 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compounds will be provided in dosage unit form containing an amount of an exendin agonist, with or without another anti-emptying agent. Therapeutically effective amounts of an exendin agonist for use in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, an effective amount of therapeutic agent will vary with many factors including the age and weight of the patient, the patient's physical condition, the blood sugar level or level of inhibition of gastric emptying to be obtained, and other factors.

Such pharmaceutical compositions are useful in causing gastric hypomotility in a subject and may be used as well in other disorders where gastric motility is beneficially reduced.

The effective daily anti-emptying dose of the compounds will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular. Orally active compounds may be taken orally, however dosages should be increased 5-10 fold.

Generally, in treating or preventing elevated, inappropriate, or undesired post-prandial blood glucose levels, the compounds of this invention may be administered to patients in need of such treatment in a dosage ranges similar to those given above, however, the compounds are administered more frequently, for example, one, two, or three times a day.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of Exendin-3

(SEQ ID NO: 1)
His Ser Asp Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 19.2 minutes.

EXAMPLE 2

Preparation of Exendin-4

```
                                         (SEQ ID NO: 2)
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser-NH2
```

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Exendin-3 as describe in Example 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 14.9 minutes. Electrospray Mass Spectrometry (M): calculated 4186.6; found 4186.0 to 4186.8 (four lots).

EXAMPLE 3

Clearance by the Kidney

The kidney can play a major role in the elimination of some molecules (drugs, peptides, proteins). For some molecules, this process begins when the kidney filters the blood at the glomerulus to produce the ultrafiltrate described below. The glomerular filter discriminates not only on the basis of molecular weight but also by acting as a negatively charged selective barrier, promoting retention of anionic compounds. The free fraction of molecules in the plasma (not protein bound) with a molecular weight less than 5 kD and an effective radii less than 15 Å are easily filtered. For larger molecular weight molecules they are filtered on a more restrictive and limited basis, principally by molecular size, structure and net charge. The cutoff point for glomerular filtration lies between albumin (67 kD) which is retained and hemoglobin (68 kD) which is filtered. Albumin, with an effective radius of about 36 Å is filtered less than 1% at the glomerulus.

Once in the glomerulus a molecule travels to the proximal tubule where it is either reabsorbed or it passes on through the loop of Henle to the distal tubule where collecting ducts drain the filtrate into the bladder. Filtered proteins and peptides are typically cleaved by brush border enzymes in the proximal tubule, from where they are efficiently retrieved by sodium/amino cotransporters (scavenging pumps). Otherwise, molecules which are polar, ionized and of large molecular weight will not be reabsorbed. Throughout this process metabolizing enzymes in the renal cortex (proximal tubules) may also degrade the molecule into more polar molecules, thereby increasing the probability for excretion into the urine. Many peptide hormones (for example, amylin, calcitonins, and GLP-1) are degraded by passage through the renal circulation, presumably by vascular ectoenzymes accessible to the plasma, independently of the process of glomerular filtration. In those examples, rates of peptide clearance from the plasma are similar to the rate of renal plasma flow, which is 3-fold greater than the rate of glomerular filtration.

Figure 6:
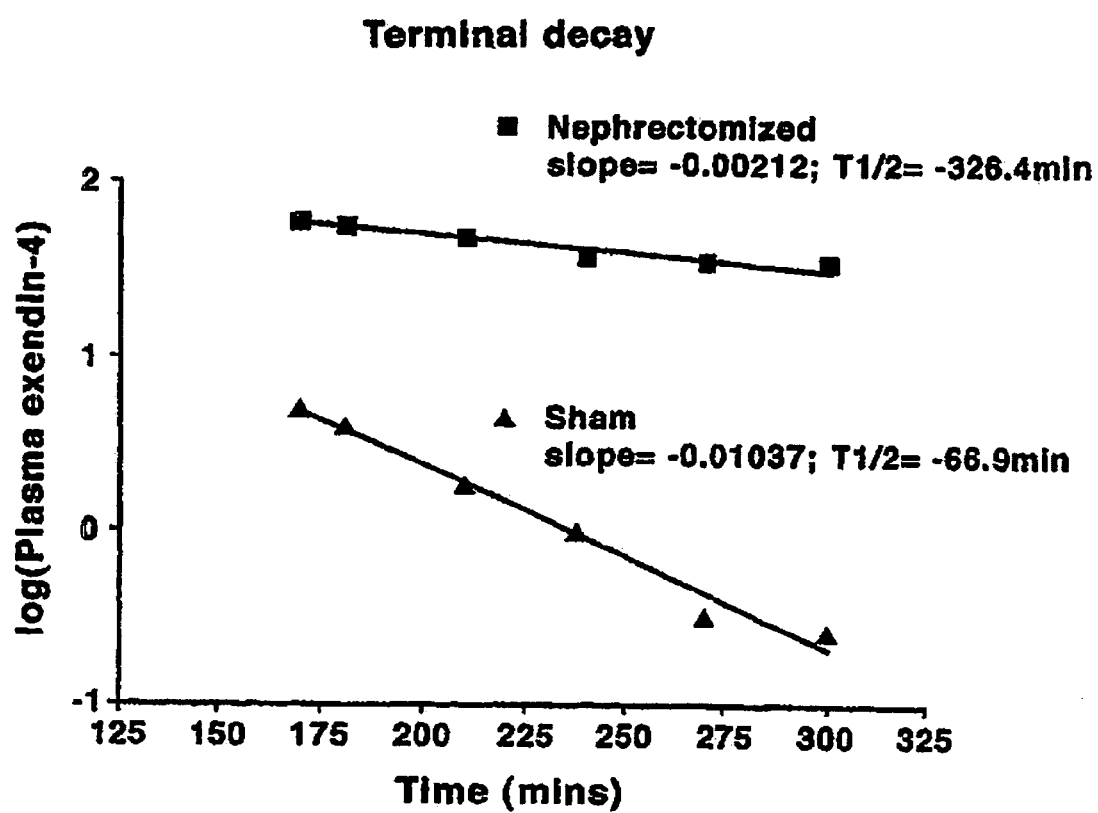
FIG. 6 is a graph showing the terminal decay of exendin-4 plasma levels in nephrectomized and sham subjects.

To test whether renal filtration could be the principal mode of exendin elimination, studies were performed in overnight fasted nephrectomized male rats infused with exendin-4 at a constant rate. Steady-state plasma levels of exendin-4 were greatly increased in nephrectomized rats compared to rats with their kidneys intact. This data indicated that the kidney was responsible for at least 80% of the clearance of exendin-4 (see FIGS. 5 and 6). Exendin-4 clearance rates in intact rats were similar to glomerular filtration rates expected in those rats (4.2 mL/min). Taken together these results indicate that very little metabolism seems to occur systemically and that most of the clearance of exendin-4 is through the kidney via filtration (but not by renal intravascular proteolysis). The low amounts of immunoreactive full-length exendin-4 in the urine are consistent with it being cleaved by brush border enzymes in the proximal tubule after filtration. These results are also consistent with the fact that studies performed to identify plasma circulating metabolites of exendin-4 yielded very little evidence of proteolytic degradation; following large intravenous doses in animals, HPLC analysis of plasma showed only the presence of intact exendin, and negligible appearance of "daughter" peaks indicative of the buildup of degradation products. This is in contrast to other peptides studied (for example amylin and GLP-1), where the disappearance of the "parent" HPLC peak was associated with the appearance of "daughter" HPLC peaks, subsequently identified as subpeptide degradants.

EXAMPLE 4

PEG Modified Exendin-4

Different spectra of biological activities of exendin-4 may be selected by putting a PEG group at appropriate positions. Loss or alteration of bioactivity has been reported for PEGylated proteins which may be due to the presence of the PEG chains themselves, the particular site occupied by the PEG chain, or the coupling conditions having an adverse effect on the protein.

Primary considerations for PEG modification in terms of filtration at the kidney of exendin and exendin agonists are size and charge. Unmodified, exendin-4 has a molecular weight of approximately 4.2 kD and is anionic in nature with an overall net charge of approximately −2 at physiological pH. One to ten, preferably one, two or three PEG constituents may be covalently linked to exendin-4 or an analog of exendin-4, for example, with one PEG constituent being preferred. The size of each independent PEG constituent can vary from a molecular weight of 500 to 20,000, preferably between 5,000 and 12,000.

Many of the methods for covalent attachment of PEG involve the epsilon-amino group on lysine. Exendin-4 has two lysines that could be modified by attachment of PEG (see compounds 201 and 202, below). In addition, the epsilon-amino groups at these positions may be masked, thereby increasing the anionic nature of the peptide.

(201) (SEQ ID NO: 211):
HGEGTFTSDLSK(PEG)QMEEEAVRLFIEWLKNGGPSSGAPPPS-NH2

(202) (SEQ ID NO: 212):
HGEGTFTSDLSKQMEEEAVRLFIEWLK(PEG)NGGPSSGAPPPS-NH2

Other positions that may be modified by substitution of a Lys-PEG or equivalent, for example, are:

(203) (SEQ ID NO: 213):
HK(PEG)EGTFTSDLSKQMEEEAVRLFIEWLKNGGPSSGAPPPS-NH₂

(204) (SEQ ID NO: 214):
HGEGK(PEG)FTSDLSKQMEEEAVRLFIEWLKNGGPSSGAPPPS-NH₂

(205) (SEQ ID NO: 215):
HGEGTFTK(PEG)DLSKQMEEEAVRLFIEWLKNGGPSSGAPPPS-NH₂

(206) (SEQ ID NO: 216):
HGEGTFTSDK(PEG)SKQMEEEAVRLFIEWLKNGGPSSGAPPPS-NH₂

(207) (SEQ ID NO: 217):
HGEGTFTSDLK(PEG)KQMEEEAVRLFIEWLKNGGPSSGAPPPS-NH₂

(208) (SEQ ID NO: 218):
HGEGTFTSDLSKK(PEG)MEEEAVRLFIEWLKNGGPSSGAPPPS-NH₂

(209) (SEQ ID NO: 219):
HGEGTFTSDLSKQMEK(PEG)EAVRLFIEWLKNGGPSSGAPPPS-NH₂

(210) (SEQ ID NO: 220):
HGEGTFTSDLSKQMEEK(PEG)AVRLFIEWLKNGGPSSGAPPPS-NH₂

(211) (SEQ ID NO: 221):
HGEGTFTSDLSKQMEEEAK(PEG)RLFIEWLKNGGPSSGAPPPS-NH₂

(212) (SEQ ID NO: 222):
HGEGTFTSDLSKQMEEEAVRK(PEG)FIEWLKNGGPSSGAPPPS-NH₂

(213) (SEQ ID NO: 223):
HGEGTFTSDLSKQMEEEAVRLFIK(PEG)WLKNGGPSSGAPPPS-NH₂

(214) (SEQ ID NO: 224):
HGEGTFTSDLSKQMEEEAVRLFIEK(PEG)LKNGGPSSGAPPPS-NH₂

(215) (SEQ ID NO: 225):
HGEGTFTSDLSKQMEEEAVRLFIEWLKK(PEG)GGPSSGAPPPS-NH₂

The peptides having the amino acid sequences of SEQ ID NOs:219, 220, and 223 contain a PEGylated Lys residue substituted for a glutamic acid at the specified location. Those in the art will appreciate that non-K(PEG) substituted molecules at these positions can instead be modified by conjugation of a PEG moiety to the glutamic acid side chain carboxyl group, which modification is referred to herein as E(PEG).

Other analogs in which Lys-PEG can be substituted include:

(216) (SEQ ID NO: 226):
HGEGTFTSDLSKQMEEEAVRLFIEWLKNK(PEG)GPSSGAPPPS-NH₂

(217) (SEQ ID NO: 227):
HGEGTFTSDLSKQMEEEAVRLFIEWLKNGK(PEG)PSSGAPPPS-NH₂

Various molecules, including K(PEG) modified and arginine substituted exendins, used in Examples 5-10 are shown in Table I, below.

TABLE I

| exendin-4 | (SEQ ID NO: 2) HGEGTFTSDLSKQMEEEAVRLFIEWLKNGGPSSGA-PPPS-NH₂ |
|---|---|
| (218) | (SEQ ID NO: 228) (CH₃)-COHGEGTFTSDLSKQMEEEAVRLFIEWLK-NGGPSSGAPPPS-NH₂ |
| (219) | (SEQ ID NO: 229) (CH₃)-CH₂HGEGTFTSDLSKQMEEEAVRLFIE-WLKNGGPSSGAPPPS-NH₂ |

TABLE I-continued

| (220) | (SEQ ID NO: 230) HGEGTFTSDLSRQMEEEAVRLFIEWLK(PEG)-NGGPSSGAPPPS-NH₂ |
|---|---|
| (221) | (SEQ ID NO: 231) HGEGTFTSDLSK(PEG)QMEEEAVRLFIEWLRN-GGPSSGAPPPS-NH₂ |
| (222) | (SEQ ID NO: 232) HGEGTFTSDLSRQMEEEAVRLFIEWLRN-GGPSSGAPPPS-NH₂ |
| (223) | (SEQ ID NO: 233) HGEGTFTSDLSRQMEEEAVRLFIEWLRN-GGPSSGAPPPK(PEG)-NH₂ |
| (224) | (SEQ ID NO: 234) HGEGTFTSDLSRQMEEEAVRLFIEWLRNGK-(PEG)PSSGAPPPS-NH₂ |
| (225) | (SEQ ID NO: 235) HGEGTFTSDLSRQMEEEAVRLFIEWLK(PEG)-NGGPSSGAPPP-NH₂ |
| (226) | (SEQ ID NO: 236) HGEGTFTSDLSK(PEG)QMEEEAVRLFIEWLRN-GGPSSGAPPPS-NH₂ |
| (227) | (SEQ ID NO: 237) (PEG)COHGEGTFTSDLSRQMEEEAVRLFIEWLRN-GGPSSGAPPPS-NH₂ |
| (228) | (SEQ ID NO: 238) (PEG)CH₂HGEGTFTSDLSRQMEEEAVRLFIEWLR-NGGPSSGAPPPS-NH₂ |
| (229) | (SEQ ID NO: 239) HGEGTFTSDLSRQMEEEAVRLFIEWLRN-GGPSSGAPPPK(PEG)-NH₂ |
| (230) | (SEQ ID NO: 240) HGEGTFTSDLSRQMEEEAVRLFIEWLRNGK(PEG)-PSSGAPPPS-NH₂ |

The various PEG modified exendins used in Examples 5-10, below, are provided in Table I, with the corresponding results being provided in Table II (see the end of Example 9). GLP-1[7-36]NH₂ (GLP-1) was purchased from Bachem (Torrance, Calif.). All other peptides were prepared using synthesis methods such as those described herein. All chemicals were of the highest commercial grade. The cAMP SPA immunoassay was purchased from Amersham. The radioligands were purchased from New England Nuclear (Boston, Mass.). RINm5F cells (American Type Tissue Collection, Rockville, Md.) were grown in DME/F12 medium containing 10% fetal bovine serum and 2 mM L-glutamine. Cells were grown at 37° C. and 5% CO₂/95% humidified air and medium was replaced every 2 to 3 days. Cells were grown to confluence then harvested and homogenized using on a Polytron homogenizer. Cell homogenates were stored frozen at −70° C. until used.

EXAMPLE 5

GLP-1 Receptor Binding Studies

Receptor binding can be assessed by measuring displacement of [$^{125}$I]GLP-1 or [$^{125}$I]exendin(9-39) from RINm5f membranes. Assay buffer contained 5 µg/ml bestatin, 1 µg/ml phosphoramidon, 1 mg/ml bovine serum albumin (fraction V), 1 mg/ml bacitracin, and 1 mM MgCl₂ in 20 mM HEPES, pH 7.4. To measure binding, 30 µg membrane protein (Bradford protein assay) is resuspended in 200 µl assay buffer and incubated with 60 pM [$^{125}$I]GLP-1 or [$^{125}$I]exendin(9-39) and unlabeled peptides for 120 minutes at 23° C. in 96 well plates (Nagle Nunc, Rochester, N.Y.). Incubations are terminated by rapid filtration with cold phosphate buffered saline, pH 7.4, through polyethyleneimine-treated GF/B glass fiber filters (Wallac Inc., Gaithersburg, Md.) using a Tomtec Mach II plate harvester (Wallac Inc., Gaithersburg, Md.). Filters are dried, combined with scintillant, and radioactivity determined in a Betaplate liquid scintillant counter (Wallac Inc.).

Peptide samples are run in the assay as duplicate points at 6 dilutions over a concentration range of $10^{-6}$M to $10^{-12}$M to generate response curves. The biological activity of a sample can be expressed as an $IC_{50}$ value, calculated from the raw data using an iterative curve-fitting program using a 4-parameter logistic equation (Prizm, GraphPAD Software).

EXAMPLE 6

Cyclase Activation Study

Assay buffer contained 10 µM GTP, 0.75 mM ATP, 2.5 mM MgCl$_2$, 0.5 mM phosphocreatine, 12.5 U/ml creatine kinase, 0.4 mg/ml aprotinin, 1 µM IBMX in 50 mM HEPES, pH 7.4. Membranes and peptides was combined in 100 ml of assay buffer in 96 well filter-bottom plates (Millipore Corp., Bedford, Mass.). After 20 minutes incubation at 37° C., the assay was terminated by transfer of supernatant by filtration into a fresh 96 well plate using a Millipore vacuum manifold. Supernatant cAMP contents were quantitated by SPA immunoassay. Peptide samples were run in the assay as triplicate points at 7 dilutions over a concentration range of $10^{-6}$M to $10^{-12}$M to generate response curves. The biological activity of a particular sample was expressed as an $EC_{50}$ value calculated as described above.

EXAMPLE 7

Determination of Blood Glucose Levels in db/db Mice

C57BLKS/J-m-db mice at least 3 months of age are utilized for the study. The mice can be obtained from The Jackson Laboratory and allowed to acclimate for at least one week before use. Mice can be housed in groups often at 22° C.±1° C. with a 12:12 light:dark cycle, with lights on at 6 a.m. All animals can be deprived of food for 2 hours before taking baseline blood samples. Approximately 70 µl of blood is drawn from each mouse via eye puncture, after a light anesthesia with metophane. After collecting baseline blood samples, to measure plasma glucose concentrations, all animals receive subcutaneous injections of either vehicle (10.9% NaCl), exendin-4 or test compound (1 µg) in vehicle. Blood samples were drawn again, using the same procedure, after exactly one hour from the injections, and plasma glucose concentrations were measured. For each animal, the % change in plasma value, from baseline value, was calculated.

EXAMPLE 8

Dose Response Determination of Blood Glucose Levels in db/db Mice

C57BLKS/J-m-db/db mice, at least 3 months of age, were utilized. The mice were obtained from The Jackson Laboratory and allowed to acclimate for at least one week before use. Mice were housed in groups often at 22° C.±1° C. with a 12:12 light:dark cycle, with lights on at 6 a.m. All animals were deprived of food for 2 hours before taking baseline blood samples. Approximately 70 µl of blood was drawn from each mouse via eye puncture, after a light anesthesia with metophane. After collecting baseline blood samples, to measure plasma glucose concentrations, all animals receive subcutaneous injections of either vehicle, exendin-4 or test compound. Blood samples were drawn again, using the same procedure, after exactly one hour from the injections, and plasma glucose concentrations were measured. For each animal, the % change in plasma value, from baseline value, was calculated and a dose dependent relationship was evaluated using Graphpad Prizm™ software.

EXAMPLE 9

Gastric Emptying

A gastric emptying study may also be carried out to examine the effects of exendin-4 and/or an exendin agonist compound on gastric emptying in rats. Such experiments typically follow a modification of the method of Scarpignato, et al., *Arch. Int. Pharmacodyn. Ther.* 246:286-94, 1980. Male Harlan Sprague Dawley (HSD) rats are used. All animals are housed at 22.7±0.8° C. in a 12:12 hour light:dark cycle (experiments being performed during the light cycle) and were fed and watered ad libitum (Diet LM-485, Teklad, Madison, Wis.). The determination of gastric emptying by the method described below can be performed after a fast of ~20 hours to ensure that the stomach contained no chyme that would interfere with spectrophotometric absorbance measurements.

Conscious rats receive by gavage 1.5 ml of an acaloric gel containing 1.5% methyl cellulose (M-0262, Sigma Chemical Co, St Louis, Mo.) and 0.05% phenol red indicator. Twenty minutes after gavage, rats are anesthetized using 5% halothane, the stomach is exposed and clamped at the pyloric and lower esophageal sphincters using artery forceps, removed and opened into an alkaline solution made up to a fixed volume. Stomach content is derived from the intensity of the phenol red in the alkaline solution, measured by absorbance at a wavelength of 560 nm. In separate experiments on several other rats, the stomach and small intestine can be both excised and opened into an alkaline solution. The quantity of phenol red that could be recovered from the upper gastrointestinal tract within 20 minutes of gavage can then be determined. Dye which appears to bind irrecoverably to the gut luminal surface accounts for the balance. To account for a maximal dye recovery of less than 100%, the percentage of stomach contents remaining after 20 min. are expressed as a fraction of the gastric contents recovered from control rats sacrificed immediately after gavage in the same experiment. Percent gastric contents remaining=(absorbance at 20 min)/(absorbance at 0 mm)×100.

EXAMPLE 10

Test Compound Injections Reduced Food Intake in Normal Mice

All mice (NIH:Swiss mice) were housed in a stable environment of 22 (±2)° C., 60 (±10) % humidity and a 12:12 light:dark cycle; with lights on at 0600. Mice were housed in groups of four in standard cages with ad libitum access to food (Teklad: LM 485; Madison, Wis.) and water except as noted, for at least two weeks before the experiments.

All experiments were conducted between the hours of 0700 and 0900. The mice were food deprived (food removed at 1600 hr from all animals on day prior to experiment) and thereafter individually housed. All mice received an intraperitoneal injection (5 µl/kg) of either saline or test compound at doses of 0.1, 1.0, 10, and 100 µg/kg, and were immediately presented with a pre-weighed food pellet (Teklad LM 485). The food pellet was weighed at 30-minute, 1-hr, 2-hr and 6-hr intervals to determine the amount of food eaten. The $ED_{50}$ for inhibition of food intake over 30 min was determined for several test compounds, and the results appear in Table II, below.

TABLE II

|  | GLP-1 Cyclase EC50 nM | Appetite Suppression ED50 ug/kg |
|---|---|---|
| exendin-4 | 0.27 | 0.21 |
| 218 | >1000 | 1.80 |
| 219 | 1.11 | 0.08 |
| 220 | 0.8 | 0.12 |
| 221 | 0.69 | 6.70 |
| 222 | 2.70 | weak |
| 223 | 0.46 | 2.40 |
| 224 | 3.22 | weak |
| 225 | 23 | weak |
| 226 | 102 | 2.40 |
| 227 | 149 | NA |
| 228 | 458 | NA |
| 229 | 60.4 | 14.50 |
| 230 | 157 | NA |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments and are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference in its entirety to the same extent as if each individual publication was specifically and individually indicated to be so incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

SEQUENCE LISTING

<160> NUMBER OF SEQ ID NOS: 240

<210> SEQ ID NO 1
<211> LENGTH: 39
<212> TYPE: PRT
<213> ORGANISM: Heloderma Horridum
<220> FEATURE:
<221> NAME/KEY: AMIDATION
<222> LOCATION: 39
<223> OTHER INFORMATION: Ser in position 39 is amidated

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser

```
<210> SEQ ID NO 2
<211> LENGTH: 39
<212> TYPE: PRT
<213> ORGANISM: Heloderma Suspectum
<220> FEATURE:
<221> NAME/KEY: AMIDATION
<222> LOCATION: 39
<223> OTHER INFORMATION: Ser in position 39 is amidated

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 3
<211> LENGTH: 30
<212> TYPE: PRT
<213> ORGANISM: Artificial Sequence
<220> FEATURE:
<223> OTHER INFORMATION: Synthetic Amino Acid Sequence

<400> SEQUENCE: 3

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 30
<223> OTHER INFORMATION: Gly in position 30 is amidated

<400> SEQUENCE: 4

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 5
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25
```

-continued

```
<210> SEQ ID NO 6
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 39
<223> OTHER INFORMATION: Ser in position 39 is amidated

<400> SEQUENCE: 6

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 7
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 7

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 8

His Gly Glu Gly Thr Phe Thr Ser Asp Leu Ser Lys Gln Leu Glu Glu
 1               5                  10                  15

Glu Ala Val Arg Leu Ala Ile Glu Phe Leu Lys Asn
            20                  25

<210> SEQ ID NO 9
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 9
<223> OTHER INFORMATION: Xaa stands for Pgly
<220> FEATURE:
<221> NAME/KEY: AMIDATION
<222> LOCATION: 18
<223> OTHER INFORMATION: Ser in position 18 is amidated
```

```
<400> SEQUENCE: 9

His Gly Glu Phe Thr Ser Asp Leu Xaa Phe Ile Glu Phe Pro Pro Pro
 1               5                  10                  15

Pro Ser

<210> SEQ ID NO 10
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 10
<223> OTHER INFORMATION: Xaa stands for naph
<220> FEATURE:
<221> NAME/KEY: AMIDATION
<222> LOCATION: 18
<223> OTHER INFORMATION: Ser in position 18 is amidated

<400> SEQUENCE: 10

His Gly Glu Phe Thr Ser Asp Leu Met Xaa Ile Glu Trp Pro Pro Pro
 1               5                  10                  15

Pro Ser

<210> SEQ ID NO 11
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 18
<223> OTHER INFORMATION: Ser in position 18 is amidated

<400> SEQUENCE: 11

His Gly Glu Phe Thr Ser Asp Leu Met Phe Val Glu Trp Pro Pro Pro
 1               5                  10                  15

Pro Ser

<210> SEQ ID NO 12
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 18
<223> OTHER INFORMATION: Ser in position 18 is amidated

<400> SEQUENCE: 12

His Gly Glu Phe Thr Ser Asp Leu Leu Phe Val Glu Phe Pro Pro Pro
 1               5                  10                  15

Pro Ser

<210> SEQ ID NO 13
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 11
<223> OTHER INFORMATION: Xaa stands for tBug
```

```
<220> FEATURE:
<221> NAME/KEY: AMIDATION
<222> LOCATION: 18
<223> OTHER INFORMATION: Ser in position 18 is amidated

<400> SEQUENCE: 13

His Gly Glu Phe Thr Ser Asp Leu Met Phe Xaa Glu Trp Pro Pro Pro
 1               5                  10                  15

Pro Ser

<210> SEQ ID NO 14
<211> LENGTH: 18
<212> TYPE: PRT
<213> ORGANISM: Artificial Sequence
<220> FEATURE:
<223> OTHER INFORMATION: Syntheic Amino Acid Sequence
<220> FEATURE:
<221> NAME/KEY: VARIANT
<222> LOCATION: 11
<223> OTHER INFORMATION: Xaa in position 11 stands of tBug
<220> FEATURE:
<221> NAME/KEY: AMIDATION
<222> LOCATION: 18
<223> OTHER INFORMATION: Ser in position 18 is amidated

<400> SEQUENCE: 14

His Gly Glu Phe Thr Ser Asp Leu Leu Phe Xaa Glu Phe Pro Pro Pro
 1               5                  10                  15

Pro Ser

<210> SEQ ID NO 15
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 18
<223> OTHER INFORMATION: Ser in position 18 is amidated

<400> SEQUENCE: 15

His Gly Glu Phe Thr Ser Asp Leu Met Phe Ile Asp Trp Pro Pro Pro
 1               5                  10                  15

Pro Ser

<210> SEQ ID NO 16
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 18
<223> OTHER INFORMATION: Ser in position 18 is amidated

<400> SEQUENCE: 16

His Ala Glu Phe Thr Ser Asp Leu Leu Phe Ile Glu Phe Pro Pro Pro
 1               5                  10                  15

Pro Ser

<210> SEQ ID NO 17
<211> LENGTH: 18
<212> TYPE: PRT
<213> ORGANISM: Artificial Sequence
<220> FEATURE:
```

```
<223> OTHER INFORMATION: Synthetic Amino Acid Sequence
<220> FEATURE:
<221> NAME/KEY: VARIANT
<222> LOCATION: (14)...(17)
<223> OTHER INFORMATION: Xaa in positions 14-17 is tPro
<220> FEATURE:
<221> NAME/KEY: AMIDATION
<222> LOCATION: 18
<223> OTHER INFORMATION: Ser in position 18 is amidated

<400> SEQUENCE: 17

His Gly Glu Phe Thr Ser Asp Leu Met Phe Ile Glu Trp Xaa Xaa Xaa
 1               5                  10                  15

Xaa Ser

<210> SEQ ID NO 18
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (15)...(17)
<223> OTHER INFORMATION: Xaa in positions 15-17 is tPro
<220> FEATURE:
<221> NAME/KEY: AMIDATION
<222> LOCATION: 18
<223> OTHER INFORMATION: Ser in position 18 is amidated

<400> SEQUENCE: 18

His Gly Glu Phe Thr Ser Asp Leu Met Phe Ile Glu Trp Pro Xaa Xaa
 1               5                  10                  15

Xaa Ser

<210> SEQ ID NO 19
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (14)...(17)
<223> OTHER INFORMATION: Xaa in positions 14-17 is hPro
<220> FEATURE:
<221> NAME/KEY: AMIDATION
<222> LOCATION: 18
<223> OTHER INFORMATION: Ser in position 18 is amidated

<400> SEQUENCE: 19

His Gly Glu Phe Thr Ser Asp Leu Met Phe Ile Glu Trp Xaa Xaa Xaa
 1               5                  10                  15

Xaa Ser

<210> SEQ ID NO 20
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (15)...(17)
<223> OTHER INFORMATION: Xaa in positions 15-17 is hPro
<220> FEATURE:
<221> NAME/KEY: AMIDATION
<222> LOCATION: 18
<223> OTHER INFORMATION: Ser in position 18 is amidated
```

-continued

```
<400> SEQUENCE: 20

His Gly Glu Phe Thr Ser Asp Leu Met Phe Ile Glu Trp Pro Xaa Xaa
1               5                   10                  15

Xaa Ser

<210> SEQ ID NO 21
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (14)...(17)
<223> OTHER INFORMATION: Xaa in positions 14-17 is tPro
<220> FEATURE:
<221> NAME/KEY: AMIDATION
<222> LOCATION: 18
<223> OTHER INFORMATION: Ser in position 18 is amidated

<400> SEQUENCE: 21

His Gly Glu Phe Thr Ser Asp Leu Leu Phe Ile Glu Phe Xaa Xaa Xaa
1               5                   10                  15

Xaa Ser

<210> SEQ ID NO 22
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (14)...(17)
<223> OTHER INFORMATION: Xaa in positions 14-17 is hPro
<220> FEATURE:
<221> NAME/KEY: AMIDATION
<222> LOCATION: 18
<223> OTHER INFORMATION: Ser in position 18 is amidated

<400> SEQUENCE: 22

His Gly Glu Phe Thr Ser Asp Leu Leu Phe Ile Glu Phe Xaa Xaa Xaa
1               5                   10                  15

Xaa Ser

<210> SEQ ID NO 23
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (14)...(17)
<223> OTHER INFORMATION: Xaa in positions 14-17 is MeAla
<220> FEATURE:
<221> NAME/KEY: AMIDATION
<222> LOCATION: 18
<223> OTHER INFORMATION: Ser in position 18 is amidated

<400> SEQUENCE: 23

His Gly Glu Phe Thr Ser Asp Leu Met Phe Ile Glu Trp Xaa Xaa Xaa
1               5                   10                  15

Xaa Ser

<210> SEQ ID NO 24
<211> LENGTH: 18
```

```
<212> TYPE: PRT
<213> ORGANISM: Artificial Sequence
<220> FEATURE:
<223> OTHER INFORMATION: Sythetic Amino Acid Sequence
<220> FEATURE:
<221> NAME/KEY: VARIANT
<222> LOCATION: (15)...(17)
<223> OTHER INFORMATION: Xaa in positions 15-17 is MeAla
<220> FEATURE:
<221> NAME/KEY: AMIDATION
<222> LOCATION: 18
<223> OTHER INFORMATION: Ser in position 18 is amidated

<400> SEQUENCE: 24

His Gly Glu Phe Thr Ser Asp Leu Met Phe Ile Glu Trp Pro Xaa Xaa
 1               5                  10                  15

Xaa Ser

<210> SEQ ID NO 25
<211> LENGTH: 18
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: (14)...(17)
<223> OTHER INFORMATION: Xaa in positions 14-17 is MeAla
<220> FEATURE:
<221> NAME/KEY: AMIDATION
<222> LOCATION: 18
<223> OTHER INFORMATION: Ser in position 18 is amidated

<400> SEQUENCE: 25

His Gly Glu Phe Thr Ser Asp Leu Leu Phe Ile Glu Phe Xaa Xaa Xaa
 1               5                  10                  15

Xaa Ser

<210> SEQ ID NO 26
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 30
<223> OTHER INFORMATION: Gly in position 30 is amidated

<400> SEQUENCE: 26

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
             20                  25                  30

<210> SEQ ID NO 27
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 27

His Gly Glu Gly Thr Phe Thr Ser Asp Leu Ser Lys Gln Met Glu Glu
 1               5                  10                  15
```

```
Glu Ala Val Arg Leu Phe Ile Glu Trp Leu Lys Asn
            20                  25

<210> SEQ ID NO 28
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 28

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 29

His Ala Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 30

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 31
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 31

His Gly Glu Gly Thr Ala Thr Ser Asp Leu Ser Lys Gln Leu Glu Glu
```

```
                1               5                  10                  15
Glu Ala Val Arg Leu Phe Ile Glu Phe Leu Lys Asn
            20                  25

<210> SEQ ID NO 32
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 32

His Gly Glu Gly Thr Phe Thr Ala Asp Leu Ser Lys Gln Leu Glu Glu
  1               5                  10                  15

Glu Ala Val Arg Leu Phe Ile Glu Phe Leu Lys Asn
            20                  25

<210> SEQ ID NO 33
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 33

His Gly Glu Gly Thr Phe Thr Ser Asp Ala Ser Lys Gln Leu Glu Glu
  1               5                  10                  15

Glu Ala Val Arg Leu Phe Ile Glu Phe Leu Lys Asn
            20                  25

<210> SEQ ID NO 34
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 34

His Gly Glu Gly Thr Phe Thr Ser Asp Leu Ala Lys Gln Leu Glu Glu
  1               5                  10                  15

Glu Ala Val Arg Leu Phe Ile Glu Phe Leu Lys Asn
            20                  25

<210> SEQ ID NO 35
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 35
```

His Gly Glu Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 36
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 36

His Gly Glu Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 37
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 37

His Gly Glu Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 38
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 38

His Gly Glu Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 39

His Gly Glu Gly Thr Phe Thr Ser Asp Leu Ser Lys Gln Leu Glu Ala
 1               5                  10                  15

Glu Ala Val Arg Leu Phe Ile Glu Phe Leu Lys Asn
             20                  25

<210> SEQ ID NO 40
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 40

His Gly Glu Gly Thr Phe Thr Ser Asp Leu Ser Lys Gln Leu Glu Glu
 1               5                  10                  15

Ala Ala Val Arg Leu Phe Ile Glu Phe Leu Lys Asn
             20                  25

<210> SEQ ID NO 41
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 41

His Gly Glu Gly Thr Phe Thr Ser Asp Leu Ser Lys Gln Leu Glu Glu
 1               5                  10                  15

Glu Ala Ala Arg Leu Phe Ile Glu Phe Leu Lys Asn
             20                  25

<210> SEQ ID NO 42
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 42

His Gly Glu Gly Thr Phe Thr Ser Asp Leu Ser Lys Gln Leu Glu Glu
 1               5                  10                  15

Glu Ala Val Ala Leu Phe Ile Glu Phe Leu Lys Asn
             20                  25

<210> SEQ ID NO 43
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

```
<400> SEQUENCE: 43

His Gly Glu Gly Thr Phe Thr Ser Asp Leu Ser Lys Gln Leu Glu Glu
 1               5                  10                  15

Glu Ala Val Arg Ala Phe Ile Glu Phe Leu Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 44

His Gly Glu Gly Thr Phe Thr Ser Asp Leu Ser Lys Gln Leu Glu Glu
 1               5                  10                  15

Glu Ala Val Arg Leu Phe Ile Ala Phe Leu Lys Asn
            20                  25

<210> SEQ ID NO 45
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 45

His Gly Glu Gly Thr Phe Thr Ser Asp Leu Ser Lys Gln Leu Glu Glu
 1               5                  10                  15

Glu Ala Val Arg Leu Phe Ile Glu Ala Leu Lys Asn
            20                  25

<210> SEQ ID NO 46
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 46

His Gly Glu Gly Thr Phe Thr Ser Asp Leu Ser Lys Gln Leu Glu Glu
 1               5                  10                  15

Glu Ala Val Arg Leu Phe Ile Glu Phe Ala Lys Asn
            20                  25

<210> SEQ ID NO 47
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated
```

```
<400> SEQUENCE: 47

His Gly Glu Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 48
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Ala in position 28 is amidated

<400> SEQUENCE: 48

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 49
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 38
<223> OTHER INFORMATION: Pro in position 38 is amidated

<400> SEQUENCE: 49

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 50
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 38
<223> OTHER INFORMATION: Pro in position 38 is amidated

<400> SEQUENCE: 50

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 51
<211> LENGTH: 37
<212> TYPE: PRT
```

```
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 37
<223> OTHER INFORMATION: Pro in position 37 is amidated

<400> SEQUENCE: 51

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 52
<211> LENGTH: 37
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 37
<223> OTHER INFORMATION: Pro in position 37 is amidated

<400> SEQUENCE: 52

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 53
<211> LENGTH: 36
<212> TYPE: PRT
<213> ORGANISM: Artificial Sequence
<220> FEATURE:
<223> OTHER INFORMATION: Synthetic Amino Aoid Sequence
<220> FEATURE:
<221> NAME/KEY: AMIDATION
<222> LOCATION: 36
<223> OTHER INFORMATION: Pro in position 36 is amidated

<400> SEQUENCE: 53

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 54
<211> LENGTH: 36
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 36
<223> OTHER INFORMATION: Pro in position 36 is amidated

<400> SEQUENCE: 54
```

```
His Gly Glu Gly Thr Phe Thr Ser Asp Leu Ser Lys Gln Leu Glu Glu
1               5                   10                  15
Glu Ala Val Arg Leu Phe Ile Glu Phe Leu Lys Asn Gly Gly Pro Ser
            20                  25                  30
Ser Gly Ala Pro
        35

<210> SEQ ID NO 55
<211> LENGTH: 35
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 35
<223> OTHER INFORMATION: Ala in position 35 is amidated

<400> SEQUENCE: 55

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
            20                  25                  30
Ser Gly Ala
        35

<210> SEQ ID NO 56
<211> LENGTH: 35
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 35
<223> OTHER INFORMATION: Ala in position 35 is amidated

<400> SEQUENCE: 56

His Gly Glu Gly Thr Phe Thr Ser Asp Leu Ser Lys Gln Leu Glu Glu
1               5                   10                  15
Glu Ala Val Arg Leu Phe Ile Glu Phe Leu Lys Asn Gly Gly Pro Ser
            20                  25                  30
Ser Gly Ala
        35

<210> SEQ ID NO 57
<211> LENGTH: 34
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 34
<223> OTHER INFORMATION: Gly in position 34 is amidated

<400> SEQUENCE: 57

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
            20                  25                  30
Ser Gly

<210> SEQ ID NO 58
```

<211> LENGTH: 34
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 34
<223> OTHER INFORMATION: Gly in position 34 is amidated

<400> SEQUENCE: 58

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly

<210> SEQ ID NO 59
<211> LENGTH: 33
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 33
<223> OTHER INFORMATION: Ser in position 33 is amidated

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 60
<211> LENGTH: 33
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 33
<223> OTHER INFORMATION: Ser in position 33 is amidated

<400> SEQUENCE: 60

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

<210> SEQ ID NO 61
<211> LENGTH: 32
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 32
<223> OTHER INFORMATION: Ser in position 32 is amidated

<400> SEQUENCE: 61

His Gly Glu Gly Thr Phe Thr Ser Asp Leu Ser Lys Gln Met Glu Glu

```
                1               5                  10                 15
Glu Ala Val Arg Leu Phe Ile Glu Trp Leu Lys Asn Gly Gly Pro Ser
                20                 25                 30
```

<210> SEQ ID NO 62
<211> LENGTH: 32
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 32
<223> OTHER INFORMATION: Ser in position 32 is amidated

<400> SEQUENCE: 62

```
His Gly Glu Gly Thr Phe Thr Ser Asp Leu Ser Lys Gln Leu Glu Glu
 1               5                  10                 15
Glu Ala Val Arg Leu Phe Ile Glu Phe Leu Lys Asn Gly Gly Pro Ser
                20                 25                 30
```

<210> SEQ ID NO 63
<211> LENGTH: 31
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 31
<223> OTHER INFORMATION: Pro in position 31 is amidated

<400> SEQUENCE: 63

```
His Gly Glu Gly Thr Phe Thr Ser Asp Leu Ser Lys Gln Met Glu Glu
 1               5                  10                 15
Glu Ala Val Arg Leu Phe Ile Glu Trp Leu Lys Asn Gly Gly Pro
                20                 25                 30
```

<210> SEQ ID NO 64
<211> LENGTH: 31
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 31
<223> OTHER INFORMATION: Pro in position 31 is amidated

<400> SEQUENCE: 64

```
His Gly Glu Gly Thr Phe Thr Ser Asp Leu Ser Lys Gln Leu Glu Glu
 1               5                  10                 15
Glu Ala Val Arg Leu Phe Ile Glu Phe Leu Lys Asn Gly Gly Pro
                20                 25                 30
```

<210> SEQ ID NO 65
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 30
<223> OTHER INFORMATION: Gly in position 30 is amidated

<400> SEQUENCE: 65

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 66
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 29
<223> OTHER INFORMATION: Gly in position 29 is amidated

<400> SEQUENCE: 66

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 67
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 29
<223> OTHER INFORMATION: Gly in position 29 is amidated

<400> SEQUENCE: 67

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 68
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36-38
<223> OTHER INFORMATION: Xaa in positions 31, 36-38 is tPro
<220> FEATURE:
<221> NAME/KEY: AMIDATION
<222> LOCATION: 38
<223> OTHER INFORMATION: tPro in postion 38 is amidated

<400> SEQUENCE: 68

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa
        35

<210> SEQ ID NO 69
<211> LENGTH: 38
<212> TYPE: PRT
<213> ORGANISM: Artificial Sequence
<220> FEATURE:

<223> OTHER INFORMATION: Synthetic Amino Acid Sequence
<220> FEATURE:
<221> NAME/KEY: VARIANT
<222> LOCATION: (36)...(38)
<223> OTHER INFORMATION: Xaa in positions 36-38 is tPro
<220> FEATURE:
<221> NAME/KEY: AMIDATION
<222> LOCATION: 38
<223> OTHER INFORMATION: tPro in position 38 is amidated

<400> SEQUENCE: 69

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 70
<211> LENGTH: 37
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31
<223> OTHER INFORMATION: Xaa in position 31 stands for Nme
<220> FEATURE:
<221> NAME/KEY: AMIDATION
<222> LOCATION: 37
<223> OTHER INFORMATION: Pro in position 37 is amidated

<400> SEQUENCE: 70

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Pro Pro
        35

<210> SEQ ID NO 71
<211> LENGTH: 37
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36-37
<223> OTHER INFORMATION: Xaa in position 31, 36-37 is Nme
<220> FEATURE:
<221> NAME/KEY: AMIDATION
<222> LOCATION: 37
<223> OTHER INFORMATION: Nme in position 37 is amidated

<400> SEQUENCE: 71

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 72
<211> LENGTH: 37
<212> TYPE: PRT

```
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36-37
<223> OTHER INFORMATION: Xaa in positions 31, 36-37 stands for hPro
<220> FEATURE:
<221> NAME/KEY: AMIDATION
<222> LOCATION: 37
<223> OTHER INFORMATION: hPro in position 37 is amidated

<400> SEQUENCE: 72

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 73
<211> LENGTH: 36
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36
<223> OTHER INFORMATION: Xaa in positions 31 and 36 stands for hPro
<220> FEATURE:
<221> NAME/KEY: AMIDATION
<222> LOCATION: 36
<223> OTHER INFORMATION: hPro in position 36 is amidated

<400> SEQUENCE: 73

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 74
<211> LENGTH: 35
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 35
<223> OTHER INFORMATION: Ala in position 35 is amidated

<400> SEQUENCE: 74

Arg Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 75
<211> LENGTH: 30
<212> TYPE: PRT
<213> ORGANISM: Artificial Sequence
<220> FEATURE:
```

```
<223> OTHER INFORMATION: Synthetic Amino Acid Sequence
<220> FEATURE:
<221> NAME/KEY: AMIDATION
<222> LOCATION: 30
<223> OTHER INFORMATION: Gly in position 30 is amidated

<400> SEQUENCE: 75

His Gly Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 76
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 6
<223> OTHER INFORMATION: Xaa in position 6 stands for naph
<220> FEATURE:
<221> NAME/KEY: AMIDATION
<222> LOCATION: 28
<223> OTHER INFORMATION: Asn in position 28 is amidated

<400> SEQUENCE: 76

His Gly Glu Gly Thr Xaa Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 77
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 77

His Gly Glu Gly Thr Phe Ser Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 78
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 78

His Gly Glu Gly Thr Phe Ser Thr Asp Leu Ser Lys Gln Met Glu Glu
 1               5                  10                  15

Glu Ala Val Arg Leu Phe Ile Glu Trp Leu Lys Asn
            20                  25
```

<210> SEQ ID NO 79
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 79

His Gly Glu Gly Thr Phe Thr Ser Glu Leu Ser Lys Gln Met Ala Glu
1               5                   10                  15

Glu Ala Val Arg Leu Phe Ile Glu Trp Leu Lys Asn
            20                  25

<210> SEQ ID NO 80
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 10
<223> OTHER INFORMATION: Xaa in position 10 stands for pGly
<220> FEATURE:
<221> NAME/KEY: AMIDATION
<222> LOCATION: 28
<223> OTHER INFORMATION: Asn in position 28 is amidated

<400> SEQUENCE: 80

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 81
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 22
<223> OTHER INFORMATION: Xaa in position 22 stands for naph
<220> FEATURE:
<221> NAME/KEY: AMIDATION
<222> LOCATION: 28
<223> OTHER INFORMATION: Asn in position 28 is amidated

<400> SEQUENCE: 81

His Gly Glu Gly Thr Phe Thr Ser Asp Leu Ser Lys Gln Leu Glu Glu
1               5                   10                  15

Glu Ala Val Arg Leu Xaa Ile Glu Phe Leu Lys Asn
            20                  25

<210> SEQ ID NO 82
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 23
<223> OTHER INFORMATION: Xaa in position 23 stands for tBug
<220> FEATURE:

```
<221> NAME/KEY: AMIDATION
<222> LOCATION: 28
<223> OTHER INFORMATION: Asn in position 28 is amidated

<400> SEQUENCE: 82
```

His Gly Glu Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

```
<210> SEQ ID NO 83
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 83
```

His Gly Glu Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

```
<210> SEQ ID NO 84
<211> LENGTH: 33
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 33
<223> OTHER INFORMATION: Ser in position 33 is amidated

<400> SEQUENCE: 84
```

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

```
<210> SEQ ID NO 85
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 29
<223> OTHER INFORMATION: Gly in position 29 is amidated

<400> SEQUENCE: 85
```

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly
            20                  25

```
<210> SEQ ID NO 86
<211> LENGTH: 37
<212> TYPE: PRT
<213> ORGANISM: Artificial Sequence
```

```
<220> FEATURE:
<223> OTHER INFORMATION: Synthetic Amino Acid Sequence
<220> FEATURE:
<221> NAME/KEY: VARIANT
<222> LOCATION: 31, 36-37
<223> OTHER INFORMATION: Xaa in positions 31, 36-37 stands for hPro
<220> FEATURE:
<221> NAME/KEY: AMIDATION
<222> LOCATION: 37
<223> OTHER INFORMATION: hPro in position 37 is amidated

<400> SEQUENCE: 86

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 87
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 27
<223> OTHER INFORMATION: Asn in position 27 is amidated

<400> SEQUENCE: 87

Xaa Glu Gly Thr Phe Thr Ser Asp Leu Ser Lys Gln Met Glu Glu Glu
 1               5                  10                  15

Ala Val Arg Leu Phe Ile Glu Trp Leu Xaa Asn
            20                  25

<210> SEQ ID NO 88
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 27
<223> OTHER INFORMATION: Asn in position 27 is amidated

<400> SEQUENCE: 88

Xaa Glu Gly Thr Phe Thr Ser Asp Leu Ser Lys Gln Leu Glu Glu Glu
 1               5                  10                  15
```

```
Ala Val Arg Leu Phe Ile Glu Phe Leu Xaa Asn
            20                  25
```

<210> SEQ ID NO 89
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 89

```
Xaa Glu Gly Thr Phe Thr Ser Asp Leu Ser Lys Gln Met Glu Glu Glu
1               5                   10                  15
Ala Val Arg Leu Phe Ile Glu Trp Leu Xaa Asn Gly Gly
            20                  25
```

<210> SEQ ID NO 90
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 90

```
Xaa Glu Gly Thr Phe Thr Ser Asp Leu Ser Lys Gln Leu Glu Glu Glu
1               5                   10                  15
Ala Val Arg Leu Phe Ile Glu Phe Leu Xaa Asn Gly Gly
            20                  25
```

<210> SEQ ID NO 91
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)

```
      octanoyl
<220> FEATURE:
<221> NAME/KEY: AMIDATION
<222> LOCATION: 27
<223> OTHER INFORMATION: Lys-NH(epsilon) octanoyl in position 27 is
      amidated

<400> SEQUENCE: 91

Xaa Glu Gly Thr Phe Thr Ser Asp Leu Ser Lys Gln Met Glu Glu Glu
 1               5                  10                  15

Ala Val Arg Leu Phe Ile Glu Trp Leu Asn Xaa
            20                  25

<210> SEQ ID NO 92
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 27
<223> OTHER INFORMATION: Lys-NH(epsilon) octanoyl in position 27 is
      amidated

<400> SEQUENCE: 92

Xaa Glu Gly Thr Phe Thr Ser Asp Leu Ser Lys Gln Leu Glu Glu Glu
 1               5                  10                  15

Ala Val Arg Leu Phe Ile Glu Phe Leu Asn Xaa
            20                  25

<210> SEQ ID NO 93
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 93

Xaa Glu Gly Thr Phe Thr Ser Asp Leu Ser Lys Gln Met Glu Glu Glu
 1               5                  10                  15

Ala Val Arg Leu Phe Ile Glu Trp Leu Asn Xaa Gly Gly
            20                  25

<210> SEQ ID NO 94
<211> LENGTH: 29
```

```
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 29
<223> OTHER INFORMATION: Gly in postion 29 is amidated

<400> SEQUENCE: 94

Xaa Glu Gly Thr Phe Thr Ser Asp Leu Ser Lys Gln Leu Glu Glu
 1               5                  10                  15

Ala Val Arg Leu Phe Ile Glu Phe Leu Asn Xaa Gly Gly
            20                  25

<210> SEQ ID NO 95
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 95

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 96
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 96

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 97
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated
```

<400> SEQUENCE: 97

His Gly Glu Ala Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 98
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 98

His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 99
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 99

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 100
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 100

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

```
<400> SEQUENCE: 101

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 102

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25

<210> SEQ ID NO 103
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 103

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn
            20                  25

<210> SEQ ID NO 104
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 104

Ala Ala Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 105
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
```

<223> OTHER INFORMATION: Asn in position 28 is amidated

<400> SEQUENCE: 105

Ala Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 106

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 107
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 107

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 108
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 108

Ala Gly Asp Gly Ala Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 109
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 109

Ala Gly Asp Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 110
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 6
<223> OTHER INFORMATION: Xaa in position 6 stands for Nala
<220> FEATURE:
<221> NAME/KEY: AMIDATION
<222> LOCATION: 28
<223> OTHER INFORMATION: Asn in position 28 is amidated

<400> SEQUENCE: 110

Ala Gly Asp Gly Thr Xaa Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 111
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 6
<223> OTHER INFORMATION: Xaa in position 6 stands for Nala
<220> FEATURE:
<221> NAME/KEY: AMIDATION
<222> LOCATION: 28
<223> OTHER INFORMATION: Asn in position 28 is amidated

<400> SEQUENCE: 111

Ala Gly Asp Gly Thr Xaa Thr Ser Asp Leu Ser Lys Gln Leu Glu Glu
1               5                   10                  15

Glu Ala Leu Ser Val Arg Leu Phe Ile Glu Phe Leu Lys Asn
            20                  25                  30

<210> SEQ ID NO 112
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 112

Ala Gly Asp Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

```
<210> SEQ ID NO 113
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 113

Ala Gly Asp Gly Thr Phe Ser Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 114
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 114

Ala Gly Asp Gly Thr Phe Thr Ala Asp Leu Ser Lys Gln Met Glu Glu
 1               5                  10                  15

Glu Ala Val Arg Leu Phe Ile Glu Trp Leu Lys Asn
            20                  25

<210> SEQ ID NO 115
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 115

Ala Gly Asp Gly Thr Phe Thr Ala Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 116
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 116

Ala Gly Asp Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25
```

<210> SEQ ID NO 117
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 117

Ala Gly Asp Gly Thr Phe Thr Ser Ala Leu Ser Lys Gln Leu Glu Glu
 1               5                  10                  15

Glu Ala Val Arg Leu Phe Ile Glu Phe Leu Lys Asn
            20                  25

<210> SEQ ID NO 118
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 118

Ala Gly Asp Gly Thr Phe Thr Ser Glu Leu Ser Lys Gln Met Glu Glu
 1               5                  10                  15

Glu Ala Val Arg Leu Phe Ile Glu Trp Leu Lys Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 119

Ala Gly Asp Gly Thr Phe Thr Ser Glu Leu Ser Lys Gln Leu Glu Glu
 1               5                  10                  15

Glu Ala Val Arg Leu Phe Ile Glu Phe Leu Lys Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 120

Ala Gly Asp Gly Thr Phe Thr Ser Asp Ala Ser Lys Gln Met Glu Glu
 1               5                  10                  15

Glu Ala Val Arg Leu Phe Ile Glu Trp Leu Lys Asn

<210> SEQ ID NO 121
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 121

Ala Gly Asp Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 10
<223> OTHER INFORMATION: Xaa in position 10 stands for Pgly
<220> FEATURE:
<221> NAME/KEY: AMIDATION
<222> LOCATION: 28
<223> OTHER INFORMATION: Asn in position 28 is amidated

<400> SEQUENCE: 122

Ala Gly Asp Gly Thr Phe Thr Ser Asp Xaa Ser Lys Gln Met Glu Glu
1               5                   10                  15

Glu Ala Val Arg Leu Phe Ile Glu Trp Leu Lys Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 10
<223> OTHER INFORMATION: Xaa in position 10 stands for Pgly
<220> FEATURE:
<221> NAME/KEY: AMIDATION
<222> LOCATION: 28
<223> OTHER INFORMATION: Asn in position 28 is amidated

<400> SEQUENCE: 123

Ala Gly Asp Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 124
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION -continued

```
<222> LOCATION: 28
<223> OTHER INFORMATION: Asn in position 28 is amidated

<400> SEQUENCE: 124

Ala Gly Asp Gly Thr Phe Thr Ser Asp Leu Ala Lys Gln Met Glu Glu
 1               5                  10                  15

Glu Ala Val Arg Leu Phe Ile Glu Trp Leu Lys Asn
            20                  25

<210> SEQ ID NO 125
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 125

Ala Gly Asp Gly Thr Phe Thr Ser Asp Leu Ala Lys Gln Leu Glu Glu
 1               5                  10                  15

Glu Ala Val Arg Leu Phe Ile Glu Phe Leu Lys Asn
            20                  25

<210> SEQ ID NO 126
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 126

Ala Gly Asp Gly Thr Phe Thr Ser Asp Leu Ser Ala Gln Met Glu Glu
 1               5                  10                  15

Glu Ala Val Arg Leu Phe Ile Glu Trp Leu Lys Asn
            20                  25

<210> SEQ ID NO 127
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 127

Ala Gly Asp Gly Thr Phe Thr Ser Asp Leu Ser Ala Gln Leu Glu Glu
 1               5                  10                  15

Glu Ala Val Arg Leu Phe Ile Glu Phe Leu Lys Asn
            20                  25

<210> SEQ ID NO 128
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
```

-continued

<221> NAME/KEY: AMIDATION
<222> LOCATION: 28
<223> OTHER INFORMATION: Asn in position 28 is amidated

<400> SEQUENCE: 128

Ala Gly Asp Gly Thr Phe Thr Ser Asp Leu Ser Lys Ala Met Glu Glu
1               5                   10                  15

Glu Ala Val Arg Leu Phe Ile Glu Trp Leu Lys Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 129

Ala Gly Asp Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 130
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 130

Ala Gly Asp Gly Thr Phe Thr Ser Asp Leu Ser Lys Gln Ala Glu Glu
1               5                   10                  15

Glu Ala Val Arg Leu Phe Ile Glu Trp Leu Lys Asn
            20                  25

<210> SEQ ID NO 131
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 131

Ala Gly Asp Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: Synthetic Amino Acid Sequence

```
<220> FEATURE:
<221> NAME/KEY: VARIANT
<222> LOCATION: 14
<223> OTHER INFORMATION: Xaa in position 14 stands for pGly
<220> FEATURE:
<221> NAME/KEY: AMIDATION
<222> LOCATION: 28
<223> OTHER INFORMATION: Asn in position 28 is amidated

<400> SEQUENCE: 132

Ala Gly Asp Gly Thr Phe Thr Ser Asp Leu Ser Lys Gln Xaa Glu Glu
 1               5                  10                  15

Glu Ala Val Arg Leu Phe Ile Glu Trp Leu Lys Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 14
<223> OTHER INFORMATION: Xaa in position 14 stands for pGly
<220> FEATURE:
<221> NAME/KEY: AMIDATION
<222> LOCATION: 28
<223> OTHER INFORMATION: Asn in position 28 is amidated

<400> SEQUENCE: 133

Ala Gly Asp Gly Thr Phe Thr Ser Asp Leu Ser Lys Gln Xaa Glu Glu
 1               5                  10                  15

Glu Ala Val Arg Leu Phe Ile Glu Phe Leu Lys Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 134

Ala Gly Asp Gly Thr Phe Thr Ser Asp Leu Ser Lys Gln Met Ala Glu
 1               5                  10                  15

Glu Ala Val Arg Leu Phe Ile Glu Trp Leu Lys Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 135

Ala Gly Asp Gly Thr Phe Thr Ser Asp Leu Ser Lys Gln Leu Ala Glu
 1               5                  10                  15

Glu Ala Val Arg Leu Phe Ile Glu Phe Leu Lys Asn
```

```
            20                  25

<210> SEQ ID NO 136
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 136

Ala Gly Asp Gly Thr Phe Thr Ser Asp Leu Ser Lys Gln Met Glu Ala
1               5                   10                  15

Glu Ala Val Arg Leu Phe Ile Glu Trp Leu Lys Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 137

Ala Gly Asp Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 138
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 138

Ala Gly Asp Gly Thr Phe Thr Ser Asp Leu Ser Lys Gln Met Glu Glu
1               5                   10                  15

Ala Ala Val Arg Leu Phe Ile Glu Trp Leu Lys Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 139

Ala Gly Asp Gly Thr Phe Thr Ser Asp Leu Ser Lys Gln Leu Glu Glu
1               5                   10                  15
```

```
Ala Ala Val Arg Leu Phe Ile Glu Phe Leu Lys Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 140

Ala Gly Asp Gly Thr Phe Thr Ser Asp Leu Ser Lys Gln Met Glu Glu
1               5                   10                  15

Glu Ala Ala Arg Leu Phe Ile Glu Trp Leu Lys Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 141

Ala Gly Asp Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 142

Ala Gly Asp Gly Thr Phe Thr Ser Asp Leu Ser Lys Gln Met Glu Glu
1               5                   10                  15

Glu Ala Val Ala Leu Phe Ile Glu Trp Leu Lys Asn
            20                  25

<210> SEQ ID NO 143
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 143

Ala Gly Asp Gly Thr Phe Thr Ser Asp Leu Ser Lys Gln Leu Glu Glu
1               5                   10                  15
```

Glu Ala Val Ala Leu Phe Ile Glu Phe Leu Lys Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 144

Ala Gly Asp Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 145
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 145

Ala Gly Asp Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 146
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 22
<223> OTHER INFORMATION: Xaa in position 22 stands for Nala
<220> FEATURE:
<221> NAME/KEY: AMIDATION
<222> LOCATION: 28
<223> OTHER INFORMATION: Asn in position 28 is amidated

<400> SEQUENCE: 146

Ala Gly Asp Gly Thr Phe Thr Ser Asp Leu Ser Lys Gln Met Glu Glu
1               5                   10                  15

Glu Ala Val Arg Leu Xaa Ile Glu Trp Leu Lys Asn
            20                  25

<210> SEQ ID NO 147
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 22
<223> OTHER INFORMATION: Xaa in position 22 stands for Nala

```
<220> FEATURE:
<221> NAME/KEY: AMIDATION
<222> LOCATION: 28
<223> OTHER INFORMATION: Asn in position 28 is amidated

<400> SEQUENCE: 147

Ala Gly Asp Gly Thr Phe Thr Ser Asp Leu Ser Lys Gln Leu Glu Glu
1               5                   10                  15

Glu Ala Val Arg Leu Xaa Ile Glu Phe Leu Lys Asn
            20                  25

<210> SEQ ID NO 148
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 148

Ala Gly Asp Gly Thr Phe Thr Ser Asp Leu Ser Lys Gln Met Glu Glu
1               5                   10                  15

Glu Ala Val Arg Leu Phe Val Glu Trp Leu Lys Asn
            20                  25

<210> SEQ ID NO 149
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 149

Ala Gly Asp Gly Thr Phe Thr Ser Asp Leu Ser Lys Gln Leu Glu Glu
1               5                   10                  15

Glu Ala Val Arg Leu Phe Val Glu Phe Leu Lys Asn
            20                  25

<210> SEQ ID NO 150
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 23
<223> OTHER INFORMATION: Xaa in position 23 stands for tGly
<220> FEATURE:
<221> NAME/KEY: AMIDATION
<222> LOCATION: 28
<223> OTHER INFORMATION: Asn in position 28 is amidated

<400> SEQUENCE: 150

Ala Gly Asp Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 151
```

```
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 23
<223> OTHER INFORMATION: Xaa in position 23 stands for tGly
<220> FEATURE:
<221> NAME/KEY: AMIDATION
<222> LOCATION: 28
<223> OTHER INFORMATION: Asn in position 28 is amidated

<400> SEQUENCE: 151

Ala Gly Asp Gly Thr Phe Thr Ser Asp Leu Ser Lys Gln Leu Glu Glu
 1               5                  10                  15

Glu Ala Val Arg Leu Phe Xaa Glu Phe Leu Lys Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 152

Ala Gly Asp Gly Thr Phe Thr Ser Asp Leu Ser Lys Gln Met Glu Gly
 1               5                  10                  15

Glu Ala Val Arg Leu Phe Ile Asp Trp Leu Lys Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 153

Ala Gly Asp Gly Thr Phe Thr Ser Asp Leu Ser Lys Gln Leu Glu Glu
 1               5                  10                  15

Glu Ala Val Arg Leu Phe Ile Asp Phe Leu Lys Asn
            20                  25

<210> SEQ ID NO 154
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 154

Ala Gly Asp Gly Thr Phe Thr Ser Asp Leu Ser Lys Gln Met Glu Glu
 1               5                  10                  15
```

```
Glu Ala Val Arg Leu Phe Ile Glu Ala Leu Lys Asn
            20                  25

<210> SEQ ID NO 155
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 155

Ala Gly Asp Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 156
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 156

Ala Gly Asp Gly Thr Phe Thr Ser Asp Leu Ser Lys Gln Met Glu Glu
1               5                   10                  15

Glu Ala Val Arg Leu Phe Ile Glu Trp Ala Lys Asn
            20                  25

<210> SEQ ID NO 157
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 157

Ala Gly Asp Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 158

Ala Gly Asp Gly Thr Phe Thr Ser Asp Leu Ser Lys Gln Met Glu Glu
1               5                   10                  15
```

```
Glu Ala Val Arg Leu Phe Ile Glu Trp Leu Ala Asn
            20                  25

<210> SEQ ID NO 159
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Asn in position 28 is amidated

<400> SEQUENCE: 159

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 160
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Ala in position 28 is amidated

<400> SEQUENCE: 160

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Ala
            20                  25

<210> SEQ ID NO 161
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 28
<223> OTHER INFORMATION: Ala in position 28 is amidated

<400> SEQUENCE: 161

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 162
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 38
<223> OTHER INFORMATION: Pro in position 38 is amidated

<400> SEQUENCE: 162

Ala Gly Glu Gly Thr Phe Thr Ser Asp Leu Ser Lys Gln Met Glu Glu
```

-continued

```
                1               5                  10                  15
Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 163
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 38
<223> OTHER INFORMATION: Pro in position 38 is amidated

<400> SEQUENCE: 163

His Gly Ala Gly Thr Phe Thr Ser Asp Leu Ser Lys Gln Leu Glu Glu
1               5                  10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 164
<211> LENGTH: 37
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 37
<223> OTHER INFORMATION: Pro in position 37 is amidated

<400> SEQUENCE: 164

His Gly Glu Ala Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 165
<211> LENGTH: 36
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 36
<223> OTHER INFORMATION: Pro in position 36 is amidated

<400> SEQUENCE: 165

His Gly Glu Gly Thr Phe Thr Ser Ala Leu Ser Lys Gln Met Glu Glu
1               5                  10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 166
```

```
<211> LENGTH: 36
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 36
<223> OTHER INFORMATION: Pro in position 36 is amidated

<400> SEQUENCE: 166

Ala Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 167
<211> LENGTH: 35
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 35
<223> OTHER INFORMATION: Ala in position 35 is amidated

<400> SEQUENCE: 167

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 168
<211> LENGTH: 35
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 35
<223> OTHER INFORMATION: Ala in position 35 is amidated

<400> SEQUENCE: 168

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala
        35

<210> SEQ ID NO 169
<211> LENGTH: 34
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 34
<223> OTHER INFORMATION: Gly in position 34 is amidated
```

```
<400> SEQUENCE: 169

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 170
<211> LENGTH: 33
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 33
<223> OTHER INFORMATION: Ser in position 33 is amidated

<400> SEQUENCE: 170

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 171
<211> LENGTH: 32
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 32
<223> OTHER INFORMATION: Ser in position 32 is amidated

<400> SEQUENCE: 171

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 32
<223> OTHER INFORMATION: Ser in position 32 is amidated

<400> SEQUENCE: 172

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

<210> SEQ ID NO 173
<211> LENGTH: 31
<212> TYPE: PRT
<213> ORGANISM: Artificial Sequence
<220> FEATURE:
<223> OTHER INFORMATION: Synthetic Amino Acid Sequence
```

```
<220> FEATURE:
<221> NAME/KEY: AMIDATION
<222> LOCATION: 31
<223> OTHER INFORMATION: Pro in position 31 is amidated

<400> SEQUENCE: 173

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 30
<223> OTHER INFORMATION: Gly in position 30 is amidated

<400> SEQUENCE: 174

His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 175
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 29
<223> OTHER INFORMATION: Gly in position 29 is amidated

<400> SEQUENCE: 175

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 176
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36-38
<223> OTHER INFORMATION: Xaa in positions 31, 36-38 stands for tPro
<220> FEATURE:
<221> NAME/KEY: AMIDATION
<222> LOCATION: 38
<223> OTHER INFORMATION: tPro in position 38 is amidated

<400> SEQUENCE: 176

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Glu Gly Xaa Ser
            20                  25                  30

Ser Gly Ala Xaa Xaa Xaa
        35
```

```
<210> SEQ ID NO 177
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 36-38
<223> OTHER INFORMATION: Xaa in positions 36-38 stands for tPro
<220> FEATURE:
<221> NAME/KEY: AMIDATION
<222> LOCATION: 38
<223> OTHER INFORMATION: tPro in position 38 is amidated

<400> SEQUENCE: 177

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 178
<211> LENGTH: 37
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36-37
<223> OTHER INFORMATION: Xaa in positions 31, 36-37 stands for Nme
<220> FEATURE:
<221> NAME/KEY: AMIDATION
<222> LOCATION: 37
<223> OTHER INFORMATION: Nme in position 37 is amidated

<400> SEQUENCE: 178

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 179
<211> LENGTH: 36
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 31, 36
<223> OTHER INFORMATION: Xaa in position 31 and 36 stands for hPro
<220> FEATURE:
<221> NAME/KEY: AMIDATION
<222> LOCATION: 36
<223> OTHER INFORMATION: hPro in position 36 is amidated

<400> SEQUENCE: 179

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30
```

Ser Gly Ala Xaa
        35

<210> SEQ ID NO 180
<211> LENGTH: 35
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 35
<223> OTHER INFORMATION: Ala in position 35 is amidated

<400> SEQUENCE: 180

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 181
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 30
<223> OTHER INFORMATION: Gly in position 30 is amidated

<400> SEQUENCE: 181

His Gly Asp Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 182
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 39
<223> OTHER INFORMATION: Ser in position 39 is amidated

<400> SEQUENCE: 182

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 183
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: AMIDATION
<222> LOCATION: 39

<223> OTHER INFORMATION: Ser in position 39 is amidated

<400> SEQUENCE: 183

Ala Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 184
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 27
<223> OTHER INFORMATION: Asn in position 27 is amidated

<400> SEQUENCE: 184

Xaa Glu Gly Thr Phe Thr Ser Ala Leu Ser Lys Gln Met Glu Glu Glu
1               5                   10                  15

Ala Val Arg Leu Phe Ile Glu Trp Leu Xaa Asn
            20                  25

<210> SEQ ID NO 185
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 27
<223> OTHER INFORMATION: Asn in position 27 is amidated

<400> SEQUENCE: 185

Xaa Glu Gly Thr Phe Thr Ser Ala Leu Ser Lys Gln Leu Glu Glu Glu
1               5                   10                  15

Ala Val Arg Leu Phe Ile Glu Phe Leu Xaa Asn
            20                  25

<210> SEQ ID NO 186
<211> LENGTH: 29
<212> TYPE: PRT
<213> ORGANISM: Artificial Sequence
<220> FEATURE:

<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 186

Xaa Glu Gly Thr Phe Thr Ser Ala Leu Ser Lys Gln Met Glu Glu
 1               5                  10                  15

Ala Val Arg Leu Phe Ile Glu Trp Leu Xaa Asn Gly Gly
            20                  25

<210> SEQ ID NO 187
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 26
<223> OTHER INFORMATION: Xaa in position 26 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 187

Xaa Glu Gly Thr Phe Thr Ser Ala Leu Ser Lys Gln Leu Glu Glu
 1               5                  10                  15

Ala Val Arg Leu Phe Ile Glu Phe Leu Xaa Asn Gly Gly
            20                  25

<210> SEQ ID NO 188
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 27
<223> OTHER INFORMATION: Lys-NH(epsilon) octanoyl in position 27 is
      amidated

<400> SEQUENCE: 188

```
Xaa Glu Gly Thr Phe Thr Ser Ala Leu Ser Lys Gln Met Glu Glu Glu
 1               5                   10                  15

Ala Val Arg Leu Phe Ile Glu Trp Leu Asn Xaa
             20                  25

<210> SEQ ID NO 189
<211> LENGTH: 27
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 27
<223> OTHER INFORMATION: Lys-NH(epsilon) octanoyl

<400> SEQUENCE: 189

Xaa Glu Gly Thr Phe Thr Ser Ala Leu Ser Lys Gln Leu Glu Glu Glu
 1               5                   10                  15

Ala Val Arg Leu Phe Ile Glu Phe Leu Asn Xaa
             20                  25

<210> SEQ ID NO 190
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in positon 1 stands for
      4-Imidazolylpropionyl-Gly
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 190

Xaa Glu Gly Thr Phe Thr Ser Ala Leu Ser Lys Gln Met Glu Glu Glu
 1               5                   10                  15

Ala Val Arg Leu Phe Ile Glu Trp Leu Asn Xaa Gly Gly
             20                  25

<210> SEQ ID NO 191
<211> LENGTH: 29
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for
      4-Imidazolylpropionyl-Gly
<220> FEATURE:
```

```
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 29
<223> OTHER INFORMATION: Gly in position 29 is amidated

<400> SEQUENCE: 191

Xaa Glu Gly Thr Phe Thr Ser Ala Leu Ser Lys Gln Leu Glu Glu Glu
1               5                   10                  15

Ala Val Arg Leu Phe Ile Glu Phe Leu Asn Xaa Gly Gly
            20                  25

<210> SEQ ID NO 192
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 28
<223> OTHER INFORMATION: Asn in position 28 is amidated

<400> SEQUENCE: 192

Ala Gly Glu Gly Thr Phe Thr Ser Asp Leu Ser Lys Gln Met Glu Glu
1               5                   10                  15

Glu Ala Val Arg Leu Phe Ile Glu Trp Leu Xaa Asn
            20                  25

<210> SEQ ID NO 193
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 28
<223> OTHER INFORMATION: Asn in position 28 is amidated

<400> SEQUENCE: 193

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Xaa Asn
            20                  25

<210> SEQ ID NO 194
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 27
<223> OTHER INFORMATION: Xaa in position 27 stands for Lys-NH(epsilon)
      octanoyl
```

```
<220> FEATURE:
<221> NAME/KEY: AMIDATION
<222> LOCATION: 30
<223> OTHER INFORMATION: Gly in position 30 is amidated

<400> SEQUENCE: 194

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Xaa Asn Gly Gly
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 27
<223> OTHER INFORMATION: Xaa in position 27 stands for Lys-NH(epsilon)
      octanoyl
<220> FEATURE:
<221> NAME/KEY: AMIDATION
<222> LOCATION: 30
<223> OTHER INFORMATION: Gly in position 30 is amidated

<400> SEQUENCE: 195

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Xaa Asn Gly Gly
            20                  25                  30

<210> SEQ ID NO 196
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 28
<223> OTHER INFORMATION: Xaa in position 28 stands for Lys-NH(epsilon)
      octanoyl
<220> FEATURE:
<221> NAME/KEY: AMIDATION
<222> LOCATION: 28
<223> OTHER INFORMATION: Lys-NH(epsilon) octanoyl in position 28 is
      amidated

<400> SEQUENCE: 196

Ala Gly Glu Gly Thr Phe Thr Ser Asp Leu Ser Lys Gln Met Glu Glu
1                5                  10                  15

Glu Ala Val Arg Leu Phe Ile Glu Trp Leu Asn Xaa
            20                  25

<210> SEQ ID NO 197
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 28
<223> OTHER INFORMATION: Xaa in position 28 stands for Lys-NH(epsilon)
      octanoyl
<220> FEATURE:
<221> NAME/KEY: AMIDATION
<222> LOCATION: 28
```

<223> OTHER INFORMATION: Lys-NH(epsilon) octanoyl in position 28 is
      amidated

<400> SEQUENCE: 197

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Asn Xaa
            20                  25

<210> SEQ ID NO 198
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 28
<223> OTHER INFORMATION: Xaa in position 28 stands for Lys-NH(epsilon)
      octanoyl
<220> FEATURE:
<221> NAME/KEY: AMIDATION
<222> LOCATION: 30
<223> OTHER INFORMATION: Gly in position 30 is amidated

<400> SEQUENCE: 198

Ala Gly Glu Gly Thr Phe Thr Ser Asp Leu Ser Lys Gln Met Glu Glu
1               5                   10                  15

Glu Ala Val Arg Leu Phe Ile Glu Trp Leu Asn Xaa Gly Gly
            20                  25                  30

<210> SEQ ID NO 199
<211> LENGTH: 30
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 28
<223> OTHER INFORMATION: Xaa in position 28 stands for Lys-NH(epsilon)
      octanoyl
<220> FEATURE:
<221> NAME/KEY: AMIDATION
<222> LOCATION: 30
<223> OTHER INFORMATION: Gly in position 30 is amidated

<400> SEQUENCE: 199

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Asn Xaa Gly Gly
            20                  25                  30

<210> SEQ ID NO 200
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His, Arg or Tyr
<220> FEATURE:
<221> NAME/KEY: VARIANT
<222> LOCATION: 2
<223> OTHER INFORMATION: Xaa in position 2 stands for Ser, Gly, Ala or
      Thr
<220> FEATURE:
<221> NAME/KEY: VARIANT -continued

```
<222> LOCATION: 3
<223> OTHER INFORMATION: Xaa in position 3 stands for Asp or Glu
<220> FEATURE:
<221> NAME/KEY: VARIANT
<222> LOCATION: 5
<223> OTHER INFORMATION: Xaa in position 5 stands for Ala or Thr
<220> FEATURE:
<221> NAME/KEY: VARIANT
<222> LOCATION: 6
<223> OTHER INFORMATION: Xaa in position 6 stands for Ala, Phe, Tyr or
      naphthylalanine
<220> FEATURE:
<221> NAME/KEY: VARIANT
<222> LOCATION: 7
<223> OTHER INFORMATION: Xaa in position 7 stands for Thr or Ser
<220> FEATURE:
<221> NAME/KEY: VARIANT
<222> LOCATION: 8
<223> OTHER INFORMATION: Xaa in position 8 stands for Ala, Ser or Thr
<220> FEATURE:
<221> NAME/KEY: VARIANT
<222> LOCATION: 9
<223> OTHER INFORMATION: Xaa in position 9 stands for Asp or Glu
<220> FEATURE:
<221> NAME/KEY: VARIANT
<222> LOCATION: 10
<223> OTHER INFORMATION: Xaa in position 10 stands for Ala, Leu, Ile,
      Val, pentylglycine or Met
<220> FEATURE:
<221> NAME/KEY: VARIANT
<222> LOCATION: 11
<223> OTHER INFORMATION: Xaa in position 11 stands for Ala or Ser
<220> FEATURE:
<221> NAME/KEY: VARIANT
<222> LOCATION: 12
<223> OTHER INFORMATION: Xaa in position 12 stands for Ala or Lys
<220> FEATURE:
<221> NAME/KEY: VARIANT
<222> LOCATION: 13
<223> OTHER INFORMATION: Xaa in position 13 stands for Ala or Gln
<220> FEATURE:
<221> NAME/KEY: VARIANT
<222> LOCATION: 14
<223> OTHER INFORMATION: Xaa in position 14 stands for Ala, Leu, Ile,
      pentylglycine, Val or Met
<220> FEATURE:
<221> NAME/KEY: VARIANT
<222> LOCATION: (15)...(17)
<223> OTHER INFORMATION: Xaa in positions 15-17 stands for Ala or Glu
<220> FEATURE:
<221> NAME/KEY: VARIANT
<222> LOCATION: 19
<223> OTHER INFORMATION: Xaa in position 19 stands for Ala or Val
<220> FEATURE:
<221> NAME/KEY: VARIANT
<222> LOCATION: 20
<223> OTHER INFORMATION: Xaa in position 20 stands for Ala or Arg
<220> FEATURE:
<221> NAME/KEY: VARIANT
<222> LOCATION: 21
<223> OTHER INFORMATION: Xaa in position 21 stands for Ala or Leu
<220> FEATURE:
<221> NAME/KEY: VARIANT
<222> LOCATION: 22
<223> OTHER INFORMATION: Xaa in position 22 stands for Ala, Phe, Tyr
      or naphthylalanine
<220> FEATURE:
<221> NAME/KEY: VARIANT
<222> LOCATION: 23
<223> OTHER INFORMATION: Xaa in position 23 stands for Ile, Val, Leu,
      pentylglycine, tert-butylglycine or Met
<220> FEATURE:
<221> NAME/KEY: VARIANT
<222> LOCATION: 24
<223> OTHER INFORMATION: Xaa in position stands for Ala, Glu or Asp
<220> FEATURE:
<221> NAME/KEY: VARIANT
<222> LOCATION: 25
<223> OTHER INFORMATION: Xaa in position stands for Ala, Trp Phe Tyr
```

```
        or naphthylalanine
<220> FEATURE:
<221> NAME/KEY: VARIANT
<222> LOCATION: 26
<223> OTHER INFORMATION: Xaa in position 26 stands for Ala or Leu
<220> FEATURE:
<221> NAME/KEY: VARIANT
<222> LOCATION: 27
<223> OTHER INFORMATION: Xaa in position 27 stands for Ala or Lys
<220> FEATURE:
<221> NAME/KEY: VARIANT
<222> LOCATION: 28
<223> OTHER INFORMATION: Xaa in position 28 stands for Ala or Asn and
        is optionally amidated

<400> SEQUENCE: 200

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa
            20                  25

<210> SEQ ID NO 201
<211> LENGTH: 10
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 1
<223> OTHER INFORMATION: Amidation, Gly at position 1 is optionally
        amidated in the case that residues in positions
        2-10 are absent
<220> FEATURE:
<221> NAME/KEY: MOD_RES
<222> LOCATION: 2
<223> OTHER INFORMATION: Amidation, Gly at position 2 is optionally
        amidated in the case that residues in position
        3-10 are absent
<220> FEATURE:
<221> NAME/KEY: MOD_RES
<222> LOCATION: 3
<223> OTHER INFORMATION: Xaa is selected from Pro, homoproline, 3Hyp,
        4Hyp, thioproline, N-alkylglycine, N-alkylpentylglycine
        or N-alkylalanine and optionally amidated in
        the case that residues in positions 4-10 are absent
<220> FEATURE:
<221> NAME/KEY: MOD_RES
<222> LOCATION: 4
<223> OTHER INFORMATION: Amidation, Ser at position 4 is optionally
        amidated in the case that residues in positions
        5-10 are absent
<220> FEATURE:
<221> NAME/KEY: MOD_RES
<222> LOCATION: 5
<223> OTHER INFORMATION: Amidation, Ser at position 5 is optionally
        amidated in the case that residues in positions
        6-10 are absent
<220> FEATURE:
<221> NAME/KEY: MOD_RES
<222> LOCATION: 6
<223> OTHER INFORMATION: Amidation, Gly at position 6 is optionally
        amidated in the case that residues in positions
        7-10 are absent
<220> FEATURE:
<221> NAME/KEY: MOD_RES
<222> LOCATION: 7
<223> OTHER INFORMATION: Amidation, Ala at position 7 is optionally
        amidated in the case that residues in positions
        8-10 are absent
<220> FEATURE:
<221> NAME/KEY: MOD_RES
<222> LOCATION: 8
<223> OTHER INFORMATION: Xaa is selected from Pro, homoproline, 3Hyp,
        4Hyp, thioproline, N-alkylglycine, N-alkylpentylglycine
        or N-alkylalanine and is optionally amidated in
```

```
        the case that residues in positions 9-10 are
        absent
<220> FEATURE:
<221> NAME/KEY: MOD_RES
<222> LOCATION: 9
<223> OTHER INFORMATION: Xaa is selected from Pro, homoproline, 3Hyp,
      4Hyp, thioproline, N-alkylglycine, N-alkylpentylglycine
      or N-alkylalanine and is optionally amidated in
      the case that residues in position 10 are absent
<220> FEATURE:
<221> NAME/KEY: MOD_RES
<222> LOCATION: 10
<223> OTHER INFORMATION: Xaa is selected from Pro, homoproline, 3Hyp,
      4Hyp, thioproline, N-alkylglycine, N-alkylpentylglycine
      or N-alkylalanine and is optionally amidated

<400> SEQUENCE: 201

Gly Gly Xaa Ser Ser Gly Ala Xaa Xaa Xaa
 1               5                  10

<210> SEQ ID NO 202
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His, Arg, Tyr,
      Ala, Norval, Val or Norleu
<220> FEATURE:
<221> NAME/KEY: VARIANT
<222> LOCATION: 2
<223> OTHER INFORMATION: Xaa in position 2 stands for Ser, Gly, Ala or
      Thr
<220> FEATURE:
<221> NAME/KEY: VARIANT
<222> LOCATION: 3
<223> OTHER INFORMATION: Xaa in position 3 stands for Ala, Asp or Glu
<220> FEATURE:
<221> NAME/KEY: VARIANT
<222> LOCATION: 4
<223> OTHER INFORMATION: Xaa in position 4 stands for Ala, Norval, Val,
      Norleu or Gly
<220> FEATURE:
<221> NAME/KEY: VARIANT
<222> LOCATION: 5
<223> OTHER INFORMATION: Xaa in position 5 stands for Ala or Thr
<220> FEATURE:
<221> NAME/KEY: VARIANT
<222> LOCATION: 6
<223> OTHER INFORMATION: Xaa in position 6 stands for Phe, Tyr or
      naphthylalanine
<220> FEATURE:
<221> NAME/KEY: VARIANT
<222> LOCATION: 7
<223> OTHER INFORMATION: Xaa in position 7 stands for Thr or Ser
<220> FEATURE:
<221> NAME/KEY: VARIANT
<222> LOCATION: 8
<223> OTHER INFORMATION: Xaa in position 8 stands for Ala, Ser or Thr
<220> FEATURE:
<221> NAME/KEY: VARIANT
<222> LOCATION: 9
<223> OTHER INFORMATION: Xaa in position 9 stands for Ala, Norval, Val
      Norleu, Asp or Glu
<220> FEATURE:
<221> NAME/KEY: VARIANT
<222> LOCATION: 10
<223> OTHER INFORMATION: Xaa in position 10 stands for Ala, Leu Ile,
      Val, pentylglycine or Met
<220> FEATURE:
<221> NAME/KEY: VARIANT
<222> LOCATION: 11
<223> OTHER INFORMATION: Xaa in position 11 stands for Ala or Ser
<220> FEATURE:
```

```
<221> NAME/KEY: VARIANT
<222> LOCATION: 12
<223> OTHER INFORMATION: Xaa in position 12 stands for Ala or Lys
<220> FEATURE:
<221> NAME/KEY: VARIANT
<222> LOCATION: 13
<223> OTHER INFORMATION: Xaa in position 13 stands for Ala or Gln
<220> FEATURE:
<221> NAME/KEY: VARIANT
<222> LOCATION: 14
<223> OTHER INFORMATION: Xaa in position 14 stands for Ala, Leu, Ile,
      pentylglycine, Val or Met
<220> FEATURE:
<221> NAME/KEY: VARIANT
<222> LOCATION: (15)...(17)
<223> OTHER INFORMATION: Xaa in positions 15-17 stands for Ala or Glu
<220> FEATURE:
<221> NAME/KEY: VARIANT
<222> LOCATION: 19
<223> OTHER INFORMATION: Xaa in position 19 stands for Ala or Val
<220> FEATURE:
<221> NAME/KEY: VARIANT
<222> LOCATION: 20
<223> OTHER INFORMATION: Xaa in position 20 stands for Ala or Arg
<220> FEATURE:
<221> NAME/KEY: VARIANT
<222> LOCATION: 21
<223> OTHER INFORMATION: Xaa in position 21 stands for Ala or Leu
<220> FEATURE:
<221> NAME/KEY: VARIANT
<222> LOCATION: 22
<223> OTHER INFORMATION: Xaa in position 22 stands for Phe, Tyr or
      naphthylalanine
<220> FEATURE:
<221> NAME/KEY: VARIANT
<222> LOCATION: 23
<223> OTHER INFORMATION: Xaa in position 23 stands for Ile, Val, Leu,
      pentylglycine, tert-butylglycine or Met
<220> FEATURE:
<221> NAME/KEY: VARIANT
<222> LOCATION: 24
<223> OTHER INFORMATION: Xaa in position 24 stands for Ala, Glu or Asp
<220> FEATURE:
<221> NAME/KEY: VARIANT
<222> LOCATION: 25
<223> OTHER INFORMATION: Xaa in position 25 stands for Ala, Trp, Phe,
      Tyr or naphthylalanine
<220> FEATURE:
<221> NAME/KEY: VARIANT
<222> LOCATION: 26
<223> OTHER INFORMATION: Xaa in position 26 stands for Ala or Leu
<220> FEATURE:
<221> NAME/KEY: VARIANT
<222> LOCATION: 27
<223> OTHER INFORMATION: Xaa in position 27 stands for Ala or Lys
<220> FEATURE:
<221> NAME/KEY: VARIANT
<222> LOCATION: 28
<223> OTHER INFORMATION: Xaa in position 28 stands for Ala or Asn and
      is optionally amidated

<400> SEQUENCE: 202

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa
                20                  25

<210> SEQ ID NO 203
<211> LENGTH: 11
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 1
```

```
<223> OTHER INFORMATION: Amidation, Gly at position 1 is optionally
      amidated in the case that residues in positions 2-11 are absent
<220> FEATURE:
<221> NAME/KEY: MOD_RES
<222> LOCATION: 2
<223> OTHER INFORMATION: Amidation, Gly at position 2 is optionally
      amidated in the case that residues in positions 3-11 are absent
<220> FEATURE:
<221> NAME/KEY: MOD_RES
<222> LOCATION: 3
<223> OTHER INFORMATION: Xaa is selected from Pro, homoproline,
      thioproline, 3Hyp, 4Hyp, N-alkylglycine, N-alkylpentylglycine
      or N-alkylalanine and is optionally amidated in
      the case that residues in positions 4-11 are absent
<220> FEATURE:
<221> NAME/KEY: MOD_RES
<222> LOCATION: 4
<223> OTHER INFORMATION: Amidation, Ser at position 4 is optional and
      optionally amidated in the case that residues in
      positions 5-11 are absent
<220> FEATURE:
<221> NAME/KEY: MOD_RES
<222> LOCATION: 5
<223> OTHER INFORMATION: Amidation, Ser at position 5 is optional and
      optionally amidated in the case that residues in
      positions 6-11 are absent
<220> FEATURE:
<221> NAME/KEY: MOD_RES
<222> LOCATION: 6
<223> OTHER INFORMATION: Amidation, Gly at position 6 is optional and
      optionally amidated in the case that residues in
      positions 7-11 are absent
<220> FEATURE:
<221> NAME/KEY: MOD_RES
<222> LOCATION: 7
<223> OTHER INFORMATION: Amidation, Ala at position 7 is optional and
      optionally amidated in the case that residues in
      positions 8-11 are absent
<220> FEATURE:
<221> NAME/KEY: MOD_RES
<222> LOCATION: 8
<223> OTHER INFORMATION: Xaa is selected from Pro, homoproline,
      thioproline, 3Hyp, 4Hyp, N-alkylglycine, N-alkylpentylglycine
      or N-alkylalanine and is optionally amidated in
      the case that residues in positions 9-11 are absent
<220> FEATURE:
<221> NAME/KEY: MOD_RES
<222> LOCATION: 9
<223> OTHER INFORMATION: Xaa is selected from Pro, homoproline,
      thioproline, 3Hyp, 4Hyp, N-alkylglycine, N-alkylpentylglycine
      or N-alkylalanine and is optionally amidated in
      the case that residues in positions 10-11 are absent
<220> FEATURE:
<221> NAME/KEY: MOD_RES
<222> LOCATION: 10
<223> OTHER INFORMATION: Xaa is selected from Pro, homoproline,
      thioproline, 3Hyp, 4Hyp, N-alkylglycine, N-alkylpentylglycine
      or N-alkylalanine and is optionally amidated in
      the case that the residue in position 11 is absent
<220> FEATURE:
<221> NAME/KEY: MOD_RES
<222> LOCATION: 11
<223> OTHER INFORMATION: Xaa is selected from Ser or Tyr and is
      optionally amidated

<400> SEQUENCE: 203

Gly Gly Xaa Ser Ser Gly Ala Xaa Xaa Xaa Xaa
 1               5                  10

<210> SEQ ID NO 204
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
```

```
<222> LOCATION: 1
<223> OTHER INFORMATION: Xaa in position 1 stands for His or Arg
<220> FEATURE:
<221> NAME/KEY: VARIANT
<222> LOCATION: 2
<223> OTHER INFORMATION: Xaa in position 2 stands for Gly or Ala
<220> FEATURE:
<221> NAME/KEY: VARIANT
<222> LOCATION: 3
<223> OTHER INFORMATION: Xaa in position 3 stands for Asp or Glu
<220> FEATURE:
<221> NAME/KEY: VARIANT
<222> LOCATION: 5
<223> OTHER INFORMATION: Xaa in position 5 stands for Ala or Thr
<220> FEATURE:
<221> NAME/KEY: VARIANT
<222> LOCATION: 6
<223> OTHER INFORMATION: Xaa in position 6 stands for Ala, Phe or
     naphthylalanine
<220> FEATURE:
<221> NAME/KEY: VARIANT
<222> LOCATION: 7
<223> OTHER INFORMATION: Xaa in position 7 stands for Thr or Ser
<220> FEATURE:
<221> NAME/KEY: VARIANT
<222> LOCATION: 8
<223> OTHER INFORMATION: Xaa in position 8 stands for Ala, Ser or Thr
<220> FEATURE:
<221> NAME/KEY: VARIANT
<222> LOCATION: 9
<223> OTHER INFORMATION: Xaa in position 9 stands for Asp or Glu
<220> FEATURE:
<221> NAME/KEY: VARIANT
<222> LOCATION: 10
<223> OTHER INFORMATION: Xaa in position 10 stands for Ala, Leu or
     pentylglycine
<220> FEATURE:
<221> NAME/KEY: VARIANT
<222> LOCATION: 11
<223> OTHER INFORMATION: Xaa in position 11 stands for Ala or Ser
<220> FEATURE:
<221> NAME/KEY: VARIANT
<222> LOCATION: 12
<223> OTHER INFORMATION: Xaa in position 12 stands for Ala or Lys
<220> FEATURE:
<221> NAME/KEY: VARIANT
<222> LOCATION: 13
<223> OTHER INFORMATION: Xaa in position 13 stands for Ala or Gln
<220> FEATURE:
<221> NAME/KEY: VARIANT
<222> LOCATION: 14
<223> OTHER INFORMATION: Xaa in position 14 stands for Ala, Leu or
     pentylglycine
<220> FEATURE:
<221> NAME/KEY: VARIANT
<222> LOCATION: (15)...(17)
<223> OTHER INFORMATION: Xaa in positions 15-17 stands for Ala or Glu
<220> FEATURE:
<221> NAME/KEY: VARIANT
<222> LOCATION: 19
<223> OTHER INFORMATION: Xaa in position 19 stands for Ala or Val
<220> FEATURE:
<221> NAME/KEY: VARIANT
<222> LOCATION: 20
<223> OTHER INFORMATION: Xaa in position 20 stands for Ala or Val
<220> FEATURE:
<221> NAME/KEY: VARIANT
<222> LOCATION: 21
<223> OTHER INFORMATION: Xaa in position 21 stands for Ala or Arg
<220> FEATURE:
<221> NAME/KEY: VARIANT
<222> LOCATION: 22
<223> OTHER INFORMATION: Xaa in position 22 stands for Ala or Leu
<220> FEATURE:
<221> NAME/KEY: VARIANT
<222> LOCATION: 23
<223> OTHER INFORMATION: Xaa in position 23 stands for Phe or
     naphthylalanine
<220> FEATURE:
```

-continued

```
<221> NAME/KEY: VARIANT
<222> LOCATION: 24
<223> OTHER INFORMATION: Xaa in position 24 stands for Ile, Val or
      tert-butylglycine
<220> FEATURE:
<221> NAME/KEY: VARIANT
<222> LOCATION: 25
<223> OTHER INFORMATION: Xaa in position 25 stands for Ala, Glu or Asp
<220> FEATURE:
<221> NAME/KEY: VARIANT
<222> LOCATION: 26
<223> OTHER INFORMATION: Xaa in position 26 stands for Ala, Trp, or Phe
<220> FEATURE:
<221> NAME/KEY: VARIANT
<222> LOCATION: 27
<223> OTHER INFORMATION: Xaa in position 27 stands for Ala or Leu
<220> FEATURE:
<221> NAME/KEY: VARIANT
<222> LOCATION: 28
<223> OTHER INFORMATION: Xaa in position 28 stands for Ala or Lys
<220> FEATURE:
<221> NAME/KEY: VARIANT
<222> LOCATION: 29
<223> OTHER INFORMATION: Xaa in position 29, if present, is Gly and is
      optionally amidated if Xaa at positions 30-38 are
      absent
<220> FEATURE:
<221> NAME/KEY: VARIANT
<222> LOCATION: 30
<223> OTHER INFORMATION: Xaa in position 30, if present, is Gly and is
      optionally amidated if Xaa at positions 31-38 are
      absent
<220> FEATURE:
<221> NAME/KEY: VARIANT
<222> LOCATION: 31
<223> OTHER INFORMATION: Xaa in position 31, if present, is Pro,
      homoproline, thioproline or N-methylalanine, and is optionally
      amidated if Xaa at positions 32-38 are absent
<220> FEATURE:
<221> NAME/KEY: VARIANT
<222> LOCATION: 32
<223> OTHER INFORMATION: Xaa in position 32, if present, is Ser and is
      optionally amidated if Xaa at positions 33-38 are
      absent
<220> FEATURE:
<221> NAME/KEY: VARIANT
<222> LOCATION: 33
<223> OTHER INFORMATION: Xaa in position 33, if present, is Ser and is
      optionally amidated if Xaa at positions 34-38 are
      absent
<220> FEATURE:
<221> NAME/KEY: VARIANT
<222> LOCATION: 34
<223> OTHER INFORMATION: Xaa in position 34, if present, is Gly and is
      optionally amidated if Xaa at positions 35-38 are
      absent
<220> FEATURE:
<221> NAME/KEY: VARIANT
<222> LOCATION: 35
<223> OTHER INFORMATION: Xaa in position 35, if present, is Ala and is
      optionally amidated if Xaa at positions 36-38 are
      absent
<220> FEATURE:
<221> NAME/KEY: VARIANT
<222> LOCATION: 36
<223> OTHER INFORMATION: Xaa in position 36, if present, is Pro,
      homoproline, thioproline or N-methylalanine, and is optionally
      amidated if Xaa at positions 37-38 are absent
<220> FEATURE:
<221> NAME/KEY: VARIANT
<222> LOCATION: 37
<223> OTHER INFORMATION: Xaa in position 37, if present, is Pro,
      homoproline, thioproline or N-methylalanine, and is optionally
      amidated if Xaa at position 38 is absent
<220> FEATURE:
<221> NAME/KEY: VARIANT
<222> LOCATION: 38
<223> OTHER INFORMATION: Xaa in position 38, if present, is Pro,
      homoproline, thioproline or N-methylalanine, and is optionally
``` amidated

<400> SEQUENCE: 204

Xaa Xaa Xaa Gly Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa
            20                  25                  30

Xaa Xaa Xaa Xaa Xaa Xaa
            35

<210> SEQ ID NO 205
<211> LENGTH: 28
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His or Ala
<220> FEATURE:
<221> NAME/KEY: VARIANT
<222> LOCATION: 2
<223> OTHER INFORMATION: Xaa in position 2 stands for Gly or Ala
<220> FEATURE:
<221> NAME/KEY: VARIANT
<222> LOCATION: 3
<223> OTHER INFORMATION: Xaa in position 3 stands for Ala, Asp or Glu
<220> FEATURE:
<221> NAME/KEY: VARIANT
<222> LOCATION: 4
<223> OTHER INFORMATION: Xaa in position 4 stands for Ala or Gly
<220> FEATURE:
<221> NAME/KEY: VARIANT
<222> LOCATION: 5
<223> OTHER INFORMATION: Xaa in position 5 stands for Ala or Thr
<220> FEATURE:
<221> NAME/KEY: VARIANT
<222> LOCATION: 6
<223> OTHER INFORMATION: Xaa in position 6 stands for Phe or
      naphthylalanine
<220> FEATURE:
<221> NAME/KEY: VARIANT
<222> LOCATION: 7
<223> OTHER INFORMATION: Xaa in position 7 stands for Thr or Ser
<220> FEATURE:
<221> NAME/KEY: VARIANT
<222> LOCATION: 8
<223> OTHER INFORMATION: Xaa in position 8 stands for Ala, Ser or Thr
<220> FEATURE:
<221> NAME/KEY: VARIANT
<222> LOCATION: 9
<223> OTHER INFORMATION: Xaa in position 9 stands for Ala, Asp or Glu
<220> FEATURE:
<221> NAME/KEY: VARIANT
<222> LOCATION: 10
<223> OTHER INFORMATION: Xaa in position 10 stands for Ala, Leu or
      pentylglycine
<220> FEATURE:
<221> NAME/KEY: VARIANT
<222> LOCATION: 11
<223> OTHER INFORMATION: Xaa in position 11 stands for Ala or Ser
<220> FEATURE:
<221> NAME/KEY: VARIANT
<222> LOCATION: 12
<223> OTHER INFORMATION: Xaa in position 12 stands for Ala or Lys
<220> FEATURE:
<221> NAME/KEY: VARIANT
<222> LOCATION: 13
<223> OTHER INFORMATION: Xaa in position 13 stands for Ala or Gln
<220> FEATURE:
<221> NAME/KEY: VARIANT
<222> LOCATION: 14
<223> OTHER INFORMATION: Xaa in position 14 stands for Ala, Leu, Met or
      pentylglycine

```
<220> FEATURE:
<221> NAME/KEY: VARIANT
<222> LOCATION: (15)...(17)
<223> OTHER INFORMATION: Xaa in positions 15-17 stands for Ala or Glu
<220> FEATURE:
<221> NAME/KEY: VARIANT
<222> LOCATION: 19
<223> OTHER INFORMATION: Xaa in position 19 stands for Ala or Val
<220> FEATURE:
<221> NAME/KEY: VARIANT
<222> LOCATION: 20
<223> OTHER INFORMATION: Xaa in position 20 stands for Ala or Arg
<220> FEATURE:
<221> NAME/KEY: VARIANT
<222> LOCATION: 21
<223> OTHER INFORMATION: Xaa in position 21 stands for Ala or Leu
<220> FEATURE:
<221> NAME/KEY: VARIANT
<222> LOCATION: 22
<223> OTHER INFORMATION: Xaa in position 22 stands for Phe or
      naphthylalanine
<220> FEATURE:
<221> NAME/KEY: VARIANT
<222> LOCATION: 23
<223> OTHER INFORMATION: Xaa in position 23 stands for Ile, Val or
      tert-butylglycine
<220> FEATURE:
<221> NAME/KEY: VARIANT
<222> LOCATION: 24
<223> OTHER INFORMATION: Xaa in position 24 stands for Ala, Glu or Asp
<220> FEATURE:
<221> NAME/KEY: VARIANT
<222> LOCATION: 25
<223> OTHER INFORMATION: Xaa in position 25 stands for Ala, Trp or Phe
<220> FEATURE:
<221> NAME/KEY: VARIANT
<222> LOCATION: 26
<223> OTHER INFORMATION: Xaa in position 26 stands for Ala or Leu
<220> FEATURE:
<221> NAME/KEY: VARIANT
<222> LOCATION: 27
<223> OTHER INFORMATION: Xaa in position 27 stands for Ala or Lys
<220> FEATURE:
<221> NAME/KEY: VARIANT
<222> LOCATION: 28
<223> OTHER INFORMATION: Xaa in position 28 stands for Ala or Asn which
      is optionally amidated

<400> SEQUENCE: 205

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa
            20                  25

<210> SEQ ID NO 206
<211> LENGTH: 11
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 1
<223> OTHER INFORMATION: Amidation, Gly at position 1 is optional and
      optionally amidated in the case that residues in
      positions 2-11 are absent
<220> FEATURE:
<221> NAME/KEY: MOD_RES
<222> LOCATION: 2
<223> OTHER INFORMATION: Amidation, Gly at position 2 is optional and
      optionally amidated in the case that residues in
      positions 3-11 are absent
<220> FEATURE:
<221> NAME/KEY: MOD_RES
<222> LOCATION: 3
<223> OTHER INFORMATION: Xaa is selected from Pro, homoproline,
```

```
      thioproline or N-methylylalanine and is optionally amidated in
      the case that residues in position 4-11 are absent
<220> FEATURE:
<221> NAME/KEY: MOD_RES
<222> LOCATION: 4
<223> OTHER INFORMATION: Amidation, Ser at position 4 is optional and
      optionally amidated in the case that residues in
      positions 5-11 are absent
<220> FEATURE:
<221> NAME/KEY: MOD_RES
<222> LOCATION: 5
<223> OTHER INFORMATION: Amidation, Ser at position 5 is optional and
      optionally amidated in the case that residues in
      positions 6-11 are absent
<220> FEATURE:
<221> NAME/KEY: MOD_RES
<222> LOCATION: 6
<223> OTHER INFORMATION: Amidation, Gly at position 6 is optional and
      optionally amidated in the case that residues in
      positions 7-11 are absent
<220> FEATURE:
<221> NAME/KEY: MOD_RES
<222> LOCATION: 7
<223> OTHER INFORMATION: Amidation, Ala at position 7 is optional and
      optionally amidated in the case that residues in
      positions 8-11 are absent
<220> FEATURE:
<221> NAME/KEY: MOD_RES
<222> LOCATION: 8
<223> OTHER INFORMATION: Xaa is selected from Pro, homoproline,
      thioproline or N-methylylalanine and is optionally amidated in
      the case that residues in position 9-11 are absent
<220> FEATURE:
<221> NAME/KEY: MOD_RES
<222> LOCATION: 9
<223> OTHER INFORMATION: Xaa is selected from Pro, homoproline,
      thioproline or N-methylylalanine and is optionally amidated in
      the case that residues in position 10-11 are
      absent
<220> FEATURE:
<221> NAME/KEY: MOD_RES
<222> LOCATION: 10
<223> OTHER INFORMATION: Xaa is selected from Pro, homoproline,
      thioproline or N-methylylalanine and is optionally amidated in
      the case that residues in position 10-11 are
      absent
<220> FEATURE:
<221> NAME/KEY: MOD_RES
<222> LOCATION: 11
<223> OTHER INFORMATION: Ser at position 11 is optional and is
      optionally amidated

<400> SEQUENCE: 206

Gly Gly Xaa Ser Ser Gly Ala Xaa Xaa Xaa Ser
 1               5                  10

<210> SEQ ID NO 207
<211> LENGTH: 38
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His, Arg, Tyr or
      4-Imidazopropionyl
<220> FEATURE:
<221> NAME/KEY: VARIANT
<222> LOCATION: 2
<223> OTHER INFORMATION: Xaa in position 2 stands for Ser, Gly, Ala or
      Thr
<220> FEATURE:
<221> NAME/KEY: VARIANT
<222> LOCATION: 3
<223> OTHER INFORMATION: Xaa in position 3 stands for Asp or Glu
<220> FEATURE:
```

-continued

```
<221> NAME/KEY: VARIANT
<222> LOCATION: 5
<223> OTHER INFORMATION: Xaa in position 5 stands for Ala or Thr
<220> FEATURE:
<221> NAME/KEY: VARIANT
<222> LOCATION: 6
<223> OTHER INFORMATION: Xaa in position 6 stands for Ala, Phe, Tyr or
      naphthylalanine
<220> FEATURE:
<221> NAME/KEY: VARIANT
<222> LOCATION: 7
<223> OTHER INFORMATION: Xaa in position 7 stands for Thr and Ser
<220> FEATURE:
<221> NAME/KEY: VARIANT
<222> LOCATION: 8
<223> OTHER INFORMATION: Xaa in position 8 stands for Ala, Ser or Thr
<220> FEATURE:
<221> NAME/KEY: VARIANT
<222> LOCATION: 9
<223> OTHER INFORMATION: Xaa in position 9 stands for Asp or Glu
<220> FEATURE:
<221> NAME/KEY: VARIANT
<222> LOCATION: 10
<223> OTHER INFORMATION: Xaa in position 10 stands for Ala, Leu, Ile,
      Val pentylglycine or Met
<220> FEATURE:
<221> NAME/KEY: VARIANT
<222> LOCATION: 11
<223> OTHER INFORMATION: Xaa in position 11 stands for Ala or Ser
<220> FEATURE:
<221> NAME/KEY: VARIANT
<222> LOCATION: 12
<223> OTHER INFORMATION: Xaa in position 12 stands for Ala or Lys
<220> FEATURE:
<221> NAME/KEY: VARIANT
<222> LOCATION: 13
<223> OTHER INFORMATION: Xaa in position 13 stands for Ala or Gln
<220> FEATURE:
<221> NAME/KEY: VARIANT
<222> LOCATION: 14
<223> OTHER INFORMATION: Xaa in position 14 stands for Ala, Leu, Ile,
      pentylglycine, Val or Met
<220> FEATURE:
<221> NAME/KEY: VARIANT
<222> LOCATION: (15)...(17)
<223> OTHER INFORMATION: Xaa in positions 15-17 stands for Ala or Glu
<220> FEATURE:
<221> NAME/KEY: VARIANT
<222> LOCATION: 19
<223> OTHER INFORMATION: Xaa in position 19 stands for Ala or Val
<220> FEATURE:
<221> NAME/KEY: VARIANT
<222> LOCATION: 20
<223> OTHER INFORMATION: Xaa in position 20 stands for Ala or Arg
<220> FEATURE:
<221> NAME/KEY: VARIANT
<222> LOCATION: 21
<223> OTHER INFORMATION: Xaa in position 21 stands for Ala, Leu or
      Lys-NH3-R where R is Lys, Arg, C1-C10 straight
      chain or branched alklnoyl or cycloalkylalkanoyl
<220> FEATURE:
<221> NAME/KEY: VARIANT
<222> LOCATION: 22
<223> OTHER INFORMATION: Xaa in position 22 stands for Phe, Tyr or
      napthylalanine
<220> FEATURE:
<221> NAME/KEY: VARIANT
<222> LOCATION: 23
<223> OTHER INFORMATION: Xaa in position 23 stands for Ile, Val Leu,
      pentylglycine, tert-butylglycine or Met
<220> FEATURE:
<221> NAME/KEY: VARIANT
<222> LOCATION: 24
<223> OTHER INFORMATION: Xaa in position 24 stands for Ala, Glu or Asp
<220> FEATURE:
<221> NAME/KEY: VARIANT
<222> LOCATION: 25
<223> OTHER INFORMATION: Xaa in position 25 stands for Ala, Trp, Phe,
      Tyr or naphthylalanine
```

```
-continued

<220> FEATURE:
<221> NAME/KEY: VARIANT
<222> LOCATION: 26
<223> OTHER INFORMATION: Xaa in position 26 stands for Ala or Leu
<220> FEATURE:
<221> NAME/KEY: VARIANT
<222> LOCATION: 27
<223> OTHER INFORMATION: Xaa in position 27 stands for Lys, Asn, or Ala,
      and Lys, is optionally Lys-NH3-R where R is Lys, Arg, C1-C10
      straight chain or branched alkanoyl or cycloalkylalkanoyl
<220> FEATURE:
<221> NAME/KEY: VARIANT
<222> LOCATION: 28
<223> OTHER INFORMATION: Xaa in position 28 stands for Lys, Asn, or Ala,
      and Lys, is optionally Lys-NH3-R where R is Lys, Arg, C1-C10
      straight chain or branched alkanoyl or cycloalkylalkanoyl
      and is optionally amidated if positions 29-38 are absent
<220> FEATURE:
<221> NAME/KEY: VARIANT
<222> LOCATION: 29
<223> OTHER INFORMATION: Xaa in position 29, if present, stands for Gly
      and is optionally amidated if positions 30-38 are absent
<220> FEATURE:
<221> NAME/KEY: VARIANT
<222> LOCATION: 30
<223> OTHER INFORMATION: Xaa in position 30, if present, stands for Gly
      and is optionally amidated if positions 31-38 are absent
<220> FEATURE:
<221> NAME/KEY: VARIANT
<222> LOCATION: 31
<223> OTHER INFORMATION: Xaa in position 31, if present, stands for Pro,
      homoproline, 3Hyp, 4Hyp, thioproline, N-alkylglycine,
      N-alkylpentylglycine or N-alkylalanine and is optionally amidated
      if positions 32-38 are absent
<220> FEATURE:
<221> NAME/KEY: VARIANT
<222> LOCATION: 32
<223> OTHER INFORMATION: Xaa in position 32, if present, stands for Ser
      and is optionally amidated if positions 33-38 are absent
<220> FEATURE:
<221> NAME/KEY: VARIANT
<222> LOCATION: 33
<223> OTHER INFORMATION: Xaa in position 33, if present, stands for Ser
      and is optionally amidated if positions 34-38 are absent
<220> FEATURE:
<221> NAME/KEY: VARIANT
<222> LOCATION: 34
<223> OTHER INFORMATION: Xaa in position 34, if present, stands for Gly
      and is optionally amidated if positions 35-38 are absent
<220> FEATURE:
<221> NAME/KEY: VARIANT
<222> LOCATION: 35
<223> OTHER INFORMATION: Xaa in position 35, if present, stands for Ala
      and is optionally amidated if positions 36-38 are absent
<220> FEATURE:
<221> NAME/KEY: VARIANT
<222> LOCATION: 36
<223> OTHER INFORMATION: Xaa in position 36, if present, stands for Pro,
      homoproline, 3Hyp, 4Hyp, thioproline, N-alkylglycine,
      N-alkylpentylglycine or N-alkylalanine and is optionally amidated
      if positions 37-38 are absent
<220> FEATURE:
<221> NAME/KEY: VARIANT
<222> LOCATION: 37
<223> OTHER INFORMATION: Xaa in position 37, if present, stands for Pro,
      homoproline, 3Hyp, 4Hyp, thioproline, N-alkylglycine,
      N-alkylpentylglycine or N-alkylalanine and is optionally amidated
      if position 38 is absent
<220> FEATURE:
<221> NAME/KEY: VARIANT
<222> LOCATION: 38
<223> OTHER INFORMATION: Xaa in position 38, if present, stands for Pro,
      homoproline, 3Hyp, 4Hyp, thioproline, N-alkylglycine,
      N-alkylpentylglycine or N-alkylalanine and is optionally amidated

<400> SEQUENCE: 207

Xaa Xaa Xaa Gly Xaa Xaa Xaa Xaa Xaa Xaa Xaa Xaa Xaa Xaa Xaa Xaa
 1               5                  10                  15
```

```
Xaa Ala Xaa Xaa Xaa Xaa Xaa Xaa Xaa Xaa Xaa Xaa Xaa Xaa Xaa
        20                  25                  30

Xaa Xaa Xaa Xaa Xaa Xaa
        35

<210> SEQ ID NO 208
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His, Arg, Tyr,
      Ala, Norval, Val, Norleu or 4-Imidazopropionyl
<220> FEATURE:
<221> NAME/KEY: VARIANT
<222> LOCATION: 2
<223> OTHER INFORMATION: Xaa in position 2 stands for Ser, Gly, Ala or
      Thr
<220> FEATURE:
<221> NAME/KEY: VARIANT
<222> LOCATION: 3
<223> OTHER INFORMATION: Xaa in position 3 stands for Ala, Asp or Glu
<220> FEATURE:
<221> NAME/KEY: VARIANT
<222> LOCATION: 4
<223> OTHER INFORMATION: Xaa in position 4 stands for Ala, Norval,Val,
      Norleu or Gly
<220> FEATURE:
<221> NAME/KEY: VARIANT
<222> LOCATION: 5
<223> OTHER INFORMATION: Xaa in position 5 stands for Ala or Thr
<220> FEATURE:
<221> NAME/KEY: VARIANT
<222> LOCATION: 6
<223> OTHER INFORMATION: Xaa in position 6 stands for Phe, Tyr or
      naphthylalanine
<220> FEATURE:
<221> NAME/KEY: VARIANT
<222> LOCATION: 7
<223> OTHER INFORMATION: Xaa in position 7 stands for Thr or Ser
<220> FEATURE:
<221> NAME/KEY: VARIANT
<222> LOCATION: 8
<223> OTHER INFORMATION: Xaa in position 8 stands for Ala, Ser or Thr
<220> FEATURE:
<221> NAME/KEY: VARIANT
<222> LOCATION: 9
<223> OTHER INFORMATION: Xaa in position 9 stands for Ala, Norval, Val,
      Norleu, Asp or Glu
<220> FEATURE:
<221> NAME/KEY: VARIANT
<222> LOCATION: 10
<223> OTHER INFORMATION: Xaa in position 10 stands for Ala, Leu, Ile,
      Val, pentylglycine or Met
<220> FEATURE:
<221> NAME/KEY: VARIANT
<222> LOCATION: 11
<223> OTHER INFORMATION: Xaa in position 11 stands for Ala or Ser
<220> FEATURE:
<221> NAME/KEY: VARIANT
<222> LOCATION: 12
<223> OTHER INFORMATION: Xaa in position 12 stands for Ala or Lys
<220> FEATURE:
<221> NAME/KEY: VARIANT
<222> LOCATION: 13
<223> OTHER INFORMATION: Xaa in position 13 stands for Ala or Gln
<220> FEATURE:
<221> NAME/KEY: VARIANT
<222> LOCATION: 14
<223> OTHER INFORMATION: Xaa in position 14 stands for Ala, Leu, Ile,
      pentylglycine, Val or Met
<220> FEATURE:
<221> NAME/KEY: VARIANT
```

```
<222> LOCATION: (15)...(17)
<223> OTHER INFORMATION: Xaa in positions 15-17 stands for Ala or Glu
<220> FEATURE:
<221> NAME/KEY: VARIANT
<222> LOCATION: 19
<223> OTHER INFORMATION: Xaa in position 19 stands for Ala or Val
<220> FEATURE:
<221> NAME/KEY: VARIANT
<222> LOCATION: 20
<223> OTHER INFORMATION: Xaa in position 20 stands for Ala or Arg
<220> FEATURE:
<221> NAME/KEY: VARIANT
<222> LOCATION: 21
<223> OTHER INFORMATION: Xaa in position 21 stands for Ala, Leu or
      Lys-NH3-R where R is Lys, Arg, C1-C10 straight chain or branched
      alkanoyl or cycloalleyl-alkanoyl
<220> FEATURE:
<221> NAME/KEY: VARIANT
<222> LOCATION: 22
<223> OTHER INFORMATION: Xaa in position 22 stands for Phe, Tyr or
      naphthylalanine
<220> FEATURE:
<221> NAME/KEY: VARIANT
<222> LOCATION: 23
<223> OTHER INFORMATION: Xaa in position 23 stands for Ile, Val, Leu,
      pentylglycine, tert-butylglycine or Met
<220> FEATURE:
<221> NAME/KEY: VARIANT
<222> LOCATION: 24
<223> OTHER INFORMATION: Xaa in position 24 stands for Ala, Glu or Asp
<220> FEATURE:
<221> NAME/KEY: VARIANT
<222> LOCATION: 25
<223> OTHER INFORMATION: Xaa in position Ala, Trp, Phe Tyr or
      napthylalanine
<220> FEATURE:
<221> NAME/KEY: VARIANT
<222> LOCATION: 26
<223> OTHER INFORMATION: Xaa in position 26 stands for Ala or Leu
<220> FEATURE:
<221> NAME/KEY: VARIANT
<222> LOCATION: 27
<223> OTHER INFORMATION: Xaa in position 27 stands for Lys, Asn, or Ala,
      and Lys, is optionally Lys-NH3-R where R is Lys, Arg, C1-C10
      straight chain or branched alkanoyl or cycloalkylalkanoyl
<220> FEATURE:
<221> NAME/KEY: VARIANT
<222> LOCATION: 28
<223> OTHER INFORMATION: Xaa in position 28 stands for Lys, Asn, or Ala,
      and Lys, is optionally Lys-NH3-R where R is Lys, Arg, C1-C10
      straight chain or branched alkanoyl or cycloalkylalkanoyl
      and is optionally amidated if positions 29-39 are absent
<220> FEATURE:
<221> NAME/KEY: VARIANT
<222> LOCATION: 29
<223> OTHER INFORMATION: Xaa in position 29, if present, stands for Gly
      and is optionally amidated if positions 30-39 are absent
<220> FEATURE:
<221> NAME/KEY: VARIANT
<222> LOCATION: 30
<223> OTHER INFORMATION: Xaa in position 30, if present, stands for Gly
      and is optionally amidated if positions 31-39 are absent
<220> FEATURE:
<221> NAME/KEY: VARIANT
<222> LOCATION: 31
<223> OTHER INFORMATION: Xaa in position 31, if present, stands for Pro,
      homoproline, 3Hyp, 4Hyp, thioproline, N-alkylglycine,
      N-alkylpentylglycine or N-alkylalanine and is optionally amidated
      if positions 32-39 are absent
<220> FEATURE:
<221> NAME/KEY: VARIANT
<222> LOCATION: 32
<223> OTHER INFORMATION: Xaa in position 32, if present, stands for Ser
      and is optionally amidated if positions 33-39 are absent
<220> FEATURE:
<221> NAME/KEY: VARIANT
<222> LOCATION: 33
<223> OTHER INFORMATION: Xaa in position 33, if present, stands for Ser
      and is optionally amidated if positions 34-39 are absent
```

```
<220> FEATURE:
<221> NAME/KEY: VARIANT
<222> LOCATION: 34
<223> OTHER INFORMATION: Xaa in position 34, if present, stands for Gly
      and is optionally amidated if positions 35-39 are absent
<220> FEATURE:
<221> NAME/KEY: VARIANT
<222> LOCATION: 35
<223> OTHER INFORMATION: Xaa in position 35, if present, stands for Ala
      and is optionally amidated if positions 36-39 are absent
<220> FEATURE:
<221> NAME/KEY: VARIANT
<222> LOCATION: 36
<223> OTHER INFORMATION: Xaa in position 36, if present, stands for Pro,
      homoproline, 3Hyp, 4Hyp, thioproline, N-alkylglycine,
      N-alkylpentylglycine or N-alkylalanine and is optionally amidated
      if positions 37-39 are absent
<220> FEATURE:
<221> NAME/KEY: VARIANT
<222> LOCATION: 37
<223> OTHER INFORMATION: Xaa in position 37, if present, stands for Pro,
      homoproline, 3Hyp, 4Hyp, thioproline, N-alkylglycine,
      N-alkylpentylglycine or N-alkylalanine and is optionally amidated
      if positions 38 and 39 are absent
<220> FEATURE:
<221> NAME/KEY: VARIANT
<222> LOCATION: 38
<223> OTHER INFORMATION: Xaa in position 38, if present, stands for Pro,
      homoproline, 3Hyp, 4Hyp, thioproline, N-alkylglycine,
      N-alkylpentylglycine or N-alkylalanine and is optionally amidated
      if position 39 is absent
<220> FEATURE:
<221> NAME/KEY: VARIANT
<222> LOCATION: 39
<223> OTHER INFORMATION: Xaa in position 39, if present, stands for Ser
      or Tyr and is optionally amidated

<400> SEQUENCE: 208

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa
         35

<210> SEQ ID NO 209
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His, Arg or Tyr
<220> FEATURE:
<221> NAME/KEY: VARIANT
<222> LOCATION: 2
<223> OTHER INFORMATION: Xaa in position 2 stands for Ser, Gly, Ala or
      Thr
<220> FEATURE:
<221> NAME/KEY: VARIANT
<222> LOCATION: 3, 9
<223> OTHER INFORMATION: Xaa in position 3 stands for Asp or Glu
<220> FEATURE:
<221> NAME/KEY: VARIANT
<222> LOCATION: 6
<223> OTHER INFORMATION: Xaa in position 6 stands for Phe, Tyr or
      naphthalanine
<220> FEATURE:
<221> NAME/KEY: VARIANT
<222> LOCATION: 7, 8
<223> OTHER INFORMATION: Xaa in position 7 stands for Thr or Ser
<220> FEATURE:
<221> NAME/KEY: VARIANT
```

```
<222> LOCATION: 10, 14
<223> OTHER INFORMATION: Xaa in position 10 and 14 stands for Leu, Ile,
      Val pentylglycine or Met
<220> FEATURE:
<221> NAME/KEY: VARIANT
<222> LOCATION: 22
<223> OTHER INFORMATION: Xaa in position 22 stands for Phe, Tyr or
      naphthalanine
<220> FEATURE:
<221> NAME/KEY: VARIANT
<222> LOCATION: 23
<223> OTHER INFORMATION: Xaa in position 23 stands for Ile, Val, Leu,
      pentylglycine, tert-butylglycine or Met
<220> FEATURE:
<221> NAME/KEY: VARIANT
<222> LOCATION: 24
<223> OTHER INFORMATION: Xaa in position 24 stands for Glu or Asp
<220> FEATURE:
<221> NAME/KEY: VARIANT
<222> LOCATION: 25
<223> OTHER INFORMATION: Xaa in position 25 stands for Trp, Phe, Tyr or
      naphthylalanine
<220> FEATURE:
<221> NAME/KEY: VARIANT
<222> LOCATION: 31, 36-38
<223> OTHER INFORMATION: Xaa in positions 31, 36-38 is selected from
      Pro, homoproline, 3Hyp, 4Hyp, thioproline, N-alkylglycine,
      N-alkylpentylglycine or N-alkylalanine
<220> FEATURE:
<221> NAME/KEY: VARIANT
<222> LOCATION: 39
<223> OTHER INFORMATION: Xaa in position 39 stands for Ser, Thr or Tyr
      and is optionally amidated

<400> SEQUENCE: 209

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
            35

<210> SEQ ID NO 210
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: VARIANT
<222> LOCATION: 1
<223> OTHER INFORMATION: Xaa in position 1 stands for His, Arg, Tyr or
      4-Imidazopropionyl
<220> FEATURE:
<221> NAME/KEY: VARIANT
<222> LOCATION: 2
<223> OTHER INFORMATION: Xaa in position 2 stands for Ser, Gly, Ala or
      Thr
<220> FEATURE:
<221> NAME/KEY: VARIANT
<222> LOCATION: 3, 9
<223> OTHER INFORMATION: Xaa in position 3 stands for Asp or Glu
<220> FEATURE:
<221> NAME/KEY: VARIANT
<222> LOCATION: 6
<223> OTHER INFORMATION: Xaa in position 6 stands for Phe, Tyr or
      naphthylalanine
<220> FEATURE:
<221> NAME/KEY: VARIANT
<222> LOCATION: 7, 8
<223> OTHER INFORMATION: Xaa in positions 7-8 stands for Thr or Ser
<220> FEATURE:
<221> NAME/KEY: VARIANT
<222> LOCATION: 10, 14
<223> OTHER INFORMATION: Xaa in positions 10 and 14 stands for Leu, Ile,
```

```
        Val, pentylglycine or Met
<220> FEATURE:
<221> NAME/KEY: VARIANT
<222> LOCATION: 22
<223> OTHER INFORMATION: Xaa in position 22 stands for Phe, Tyr or
      naphthylalanine
<220> FEATURE:
<221> NAME/KEY: VARIANT
<222> LOCATION: 23
<223> OTHER INFORMATION: Xaa in position 23 stands for Ile, Val, Leu,
      pentylglycine, tert-butylglycine or Met
<220> FEATURE:
<221> NAME/KEY: VARIANT
<222> LOCATION: 24
<223> OTHER INFORMATION: Xaa in position 24 stands for Glu or Asp
<220> FEATURE:
<221> NAME/KEY: VARIANT
<222> LOCATION: 25
<223> OTHER INFORMATION: Xaa in position 25 stands for Trp, Phe, Tyr or
      naphthylalanine
<220> FEATURE:
<221> NAME/KEY: VARIANT
<222> LOCATION: 27
<223> OTHER INFORMATION: Xaa in position 27 stands for Lys or Asn, and
      Lys is optionally Lys-NH3-R where R is Lys, Arg, C1-C10
      straight chain or branched alkanoyl or
      cycloalkylalkanoyl
<220> FEATURE:
<221> NAME/KEY: VARIANT
<222> LOCATION: 28
<223> OTHER INFORMATION: Xaa in position 28 stands for Lys or Asn, and
      Lys is optionally Lys-NH3-R where R is Lys, Arg, C1-C10
      straight chain or branched alkanoyl or
      cycloalkylalkanoyl
<220> FEATURE:
<221> NAME/KEY: VARIANT
<222> LOCATION: 31, 36-38
<223> OTHER INFORMATION: Xaa in positions 31, 35-38 are selected from
      Pro, homoproline, 3Hyp, 4Hyp, thioproline,
      N-alkylglycine, N-alkylpentylglycine or
      N-alkylalanine
<220> FEATURE:
<221> NAME/KEY: VARIANT
<222> LOCATION: 39
<223> OTHER INFORMATION: Xaa in position 39 stands for Ser, Thr or Tyr
      and is optionally amidated

<400> SEQUENCE: 210

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Xaa Xaa Gly Gly Xaa Ser
                20                  25                  30

Ser Gly Ala Xaa Xaa Xaa Xaa
                35

<210> SEQ ID NO 211
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 12
<223> OTHER INFORMATION: Lys in position 12 is PEGylated
<220> FEATURE:
<221> NAME/KEY: AMIDATION
<222> LOCATION: 39
<223> OTHER INFORMATION: Ser in position 39 is amidated

<400> SEQUENCE: 211

His Gly Glu Gly Thr Phe Thr Ser Asp Leu Ser Lys Gln Met Glu Glu
 1               5                  10                  15
```

```
Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 212
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 27
<223> OTHER INFORMATION: Lys at position 27 is PEGylated
<220> FEATURE:
<221> NAME/KEY: AMIDATION
<222> LOCATION: 39
<223> OTHER INFORMATION: Ser in position 39 is amidated

<400> SEQUENCE: 212

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 213
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 2
<223> OTHER INFORMATION: Lys at position 2 is PEGylated
<220> FEATURE:
<221> NAME/KEY: AMIDATION
<222> LOCATION: 39
<223> OTHER INFORMATION: Ser in position 39 is amidated

<400> SEQUENCE: 213

His Lys Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 214
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 5
<223> OTHER INFORMATION: Lys in position 5 is PEGylated
<220> FEATURE:
<221> NAME/KEY: AMIDATION
<222> LOCATION: 39
<223> OTHER INFORMATION: Ser in position 39 is amidated

<400> SEQUENCE: 214

His Gly Glu Gly Lys Phe Thr Ser Asp Leu Ser Lys Gln Met Glu Glu
```

-continued

```
                1               5                  10                 15
Glu Ala Val Arg Leu Phe Ile Glu Trp Leu Lys Asn Gly Gly Pro Ser
                20                 25                 30

Ser Gly Ala Pro Pro Ser
        35

<210> SEQ ID NO 215
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 8
<223> OTHER INFORMATION: Lys in position 8 is PEGylated
<220> FEATURE:
<221> NAME/KEY: AMIDATION
<222> LOCATION: 39
<223> OTHER INFORMATION: Ser in position 39 is amidated

<400> SEQUENCE: 215

His Gly Glu Gly Thr Phe Thr Lys Asp Leu Ser Lys Gln Met Glu Glu
  1               5                  10                 15

Glu Ala Val Arg Leu Phe Ile Glu Trp Leu Lys Asn Gly Gly Pro Ser
                20                 25                 30

Ser Gly Ala Pro Pro Ser
        35

<210> SEQ ID NO 216
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 10
<223> OTHER INFORMATION: Lys in position 10 is PEGylated
<220> FEATURE:
<221> NAME/KEY: AMIDATION
<222> LOCATION: 39
<223> OTHER INFORMATION: Ser in position 39 is amidated

<400> SEQUENCE: 216

His Gly Glu Gly Thr Phe Thr Ser Asp Lys Ser Lys Gln Met Glu Glu
  1               5                  10                 15

Glu Ala Val Arg Leu Phe Ile Glu Trp Leu Lys Asn Gly Gly Pro Ser
                20                 25                 30

Ser Gly Ala Pro Pro Ser
        35

<210> SEQ ID NO 217
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 11
<223> OTHER INFORMATION: Lys in position 11 is PEGylated
<220> FEATURE:
<221> NAME/KEY: AMIDATION
<222> LOCATION: 39
<223> OTHER INFORMATION: Ser in position 39 is amidated

<400> SEQUENCE: 217
```

His Gly Glu Gly Thr Phe Thr Ser Asp Leu Lys Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 218
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 13
<223> OTHER INFORMATION: Lys in position 13 is PEGylated
<220> FEATURE:
<221> NAME/KEY: AMIDATION
<222> LOCATION: 39
<223> OTHER INFORMATION: Ser in position 39 is amidated

<400> SEQUENCE: 218

His Gly Glu Gly Thr Phe Thr Ser Asp Leu Ser Lys Lys Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 219
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 16
<223> OTHER INFORMATION: Lys in position 16 is PEGylated
<220> FEATURE:
<221> NAME/KEY: AMIDATION
<222> LOCATION: 39
<223> OTHER INFORMATION: Ser in position 39 is amidated

<400> SEQUENCE: 219

His Gly Glu Gly Thr Phe Thr Ser Asp Leu Ser Lys Gln Met Glu Lys
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 220
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 17
<223> OTHER INFORMATION: Lys in position 17 is PEGylated
<220> FEATURE:
<221> NAME/KEY: AMIDATION
<222> LOCATION: 39
<223> OTHER INFORMATION: Ser in position 39 is amidated

```
<400> SEQUENCE: 220

His Gly Glu Gly Thr Phe Thr Ser Asp Leu Ser Lys Gln Met Glu Glu
 1               5                  10                  15

Lys Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 221
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 19
<223> OTHER INFORMATION: Lys in position 19 is PEGylated
<220> FEATURE:
<221> NAME/KEY: AMIDATION
<222> LOCATION: 39
<223> OTHER INFORMATION: Ser in position 39 is amidated

<400> SEQUENCE: 221

His Gly Glu Gly Thr Phe Thr Ser Asp Leu Ser Lys Gln Met Glu Glu
 1               5                  10                  15

Glu Ala Lys Arg Leu Phe Ile Glu Trp Leu Lys Asn Gly Gly Pro Ser
            20                  25                  30

Ser Gly Ala Pro Pro Pro Ser
        35

<210> SEQ ID NO 222
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 21
<223> OTHER INFORMATION: Lys in position 21 is PEGylated
<220> FEATURE:
<221> NAME/KEY: AMIDATION
<222> LOCATION: 39
<223> OTHER INFORMATION: Ser in position 39 is amidated

<400> SEQUENCE: 222

His Gly Glu Gly Thr Phe Thr Ser Asp Leu Ser Lys Gln Met Glu Glu
 1               5                  10                  15

Glu Ala Val Arg Lys Phe Ile Glu Trp Leu Lys Asn Gly Gly Pro Ser
            20                  25                  30

Ser Gly Ala Pro Pro Pro Ser
        35

<210> SEQ ID NO 223
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 24
<223> OTHER INFORMATION: Lys in position 24 is PEGylated
<220> FEATURE:
<221> NAME/KEY: AMIDATION
```

<222> LOCATION: 39
<223> OTHER INFORMATION: Ser in position 39 is amidated

<400> SEQUENCE: 223

His Gly Glu Gly Thr Phe Thr Ser Asp Leu Ser Lys Gln Met Glu Glu
1               5                   10                  15

Glu Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 224
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 25
<223> OTHER INFORMATION: Lys in position 25 is PEGylated
<220> FEATURE:
<221> NAME/KEY: AMIDATION
<222> LOCATION: 39
<223> OTHER INFORMATION: Ser in position 39 is amidated

<400> SEQUENCE: 224

His Gly Glu Gly Thr Phe Thr Ser Asp Leu Ser Lys Gln Met Glu Glu
1               5                   10                  15

Glu Ala Val Arg Leu Phe Ile Glu Lys Leu Lys Asn Gly Gly Pro Ser
            20                  25                  30

Ser Gly Ala Pro Pro Pro Ser
        35

<210> SEQ ID NO 225
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 28
<223> OTHER INFORMATION: Lys in position 28 is PEGylated
<220> FEATURE:
<221> NAME/KEY: AMIDATION
<222> LOCATION: 39
<223> OTHER INFORMATION: Ser in position 39 is amidated

<400> SEQUENCE: 225

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 226
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 29
<223> OTHER INFORMATION: Lys in position 29 is PEGylated

```
<220> FEATURE:
<221> NAME/KEY: AMIDATION
<222> LOCATION: 39
<223> OTHER INFORMATION: Ser in position 39 is amidated

<400> SEQUENCE: 226

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Lys Gly Pro Ser
            20                  25                  30

Ser Gly Ala Pro Pro Pro Ser
        35

<210> SEQ ID NO 227
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 30
<223> OTHER INFORMATION: Lys in position 30 is PEGylated
<220> FEATURE:
<221> NAME/KEY: AMIDATION
<222> LOCATION: 39
<223> OTHER INFORMATION: Ser in position 39 is amidated

<400> SEQUENCE: 227

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Lys Pro Ser
            20                  25                  30

Ser Gly Ala Pro Pro Pro Ser
        35

<210> SEQ ID NO 228
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 1
<223> OTHER INFORMATION: His at position 1 is acylated
<220> FEATURE:
<221> NAME/KEY: AMIDATION
<222> LOCATION: 39
<223> OTHER INFORMATION: Ser in position 39 is amidated

<400> SEQUENCE: 228

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 229
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
```

```
<222> LOCATION: 1
<223> OTHER INFORMATION: His at position 1 is alkylated
<220> FEATURE:
<221> NAME/KEY: AMIDATION
<222> LOCATION: 39
<223> OTHER INFORMATION: Ser in position 39 is amidated

<400> SEQUENCE: 229

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 230
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 27
<223> OTHER INFORMATION: Lys in position 27 is PEGylated
<220> FEATURE:
<221> NAME/KEY: AMIDATION
<222> LOCATION: 39
<223> OTHER INFORMATION: Ser in position 39 is amidated

<400> SEQUENCE: 230

His Gly Glu Gly Thr Phe Thr Ser Asp Leu Ser Arg Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 231
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 12
<223> OTHER INFORMATION: Lys in position 12 is PEGylated
<220> FEATURE:
<221> NAME/KEY: AMIDATION
<222> LOCATION: 39
<223> OTHER INFORMATION: Ser in position 39 is amidated

<400> SEQUENCE: 231

His Gly Glu Gly Thr Phe Thr Ser Asp Leu Ser Lys Gln Met Glu Glu
 1               5                  10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 232
<211> LENGTH: 39
<212> TYPE: PRT
<213> ORGANISM: Artificial Sequence
<220> FEATURE:
<223> OTHER INFORMATION: Synthetic Amino Acid Sequence
```

```
<220> FEATURE:
<221> NAME/KEY: AMIDATION
<222> LOCATION: 39
<223> OTHER INFORMATION: Ser in position 39 is amidated

<400> SEQUENCE: 232

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 233
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 39
<223> OTHER INFORMATION: Lys in position 39 is PEGylated
<220> FEATURE:
<221> NAME/KEY: AMIDATION
<222> LOCATION: 39
<223> OTHER INFORMATION: Lys in position 39 is amidated

<400> SEQUENCE: 233

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Lys
        35

<210> SEQ ID NO 234
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 30
<223> OTHER INFORMATION: Lys in position 30 is PEGylated
<220> FEATURE:
<221> NAME/KEY: AMIDATION
<222> LOCATION: 39
<223> OTHER INFORMATION: Ser in position 39 is amidated

<400> SEQUENCE: 234

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Lys Pro Ser
            20                  25                  30

Ser Gly Ala Pro Pro Pro Ser
        35

<210> SEQ ID NO 235
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
```

<222> LOCATION: 27
<223> OTHER INFORMATION: Lys in position 27 is PEGylated
<220> FEATURE:
<221> NAME/KEY: AMIDATION
<222> LOCATION: 39
<223> OTHER INFORMATION: Ser in position 39 is amidated

<400> SEQUENCE: 235

His Gly Glu Gly Thr Phe Thr Ser Asp Leu Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 236
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 12
<223> OTHER INFORMATION: Lys in position 12 is PEGylated
<220> FEATURE:
<221> NAME/KEY: AMIDATION
<222> LOCATION: 39
<223> OTHER INFORMATION: Ser in position 39 is amidated

<400> SEQUENCE: 236

His Gly Glu Gly Thr Phe Thr Ser Asp Leu Ser Lys Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 237
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 1
<223> OTHER INFORMATION: His in position 1 is PEGylated
<220> FEATURE:
<221> NAME/KEY: AMIDATION
<222> LOCATION: 39
<223> OTHER INFORMATION: Ser in position 39 is amidated

<400> SEQUENCE: 237

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 238
<211> LENGTH: 39
<212> TYPE: PRT
<213> ORGANISM: Artificial Sequence
<220> FEATURE:
<223> OTHER INFORMATION: Synthetic Amino Acid Sequence

```
<220> FEATURE:
<221> NAME/KEY: MOD_RES
<222> LOCATION: 1
<223> OTHER INFORMATION: His in position 1 is PEGylated
<220> FEATURE:
<221> NAME/KEY: AMIDATION
<222> LOCATION: 39
<223> OTHER INFORMATION: Ser in position 39 is amidated

<400> SEQUENCE: 238

His Gly Glu Gly Thr Phe Thr Ser Asp Leu Ser Arg Gln Met Glu Glu
 1               5                  10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 239
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 39
<223> OTHER INFORMATION: Lys in position 39 is PEGylated
<220> FEATURE:
<221> NAME/KEY: AMIDATION
<222> LOCATION: 39
<223> OTHER INFORMATION: Lys in position 39 is amidated

<400> SEQUENCE: 239

His Gly Glu Gly Thr Phe Thr Ser Asp Leu Ser Arg Gln Met Glu Glu
 1               5                  10                  15

Glu Ala Val Arg Leu Phe Ile Glu Trp Leu Arg Asn Gly Gly Pro Ser
            20                  25                  30

Ser Gly Ala Pro Pro Pro Lys
        35

<210> SEQ ID NO 240
<211> LENGTH: 39
<212> TYPE: PRT
<213> ORGANISM: Artificial Sequence
<220> FEATURE:
<223> OTHER INFORMATION: Synthetic Amino Acid Sequence
<220> FEATURE:
<221> NAME/KEY: MOD_RES
<222> LOCATION: 30
<223> OTHER INFORMATION: Lys in position 30 is PEGylated
<220> FEATURE:
<221> NAME/KEY: AMIDATION
<222> LOCATION: 39
<223> OTHER INFORMATION: Ser in position 39 is amidated

<400> SEQUENCE: 240

His Gly Glu Gly Thr Phe Thr Ser Asp Leu Ser Arg Gln Met Glu Glu
 1               5                  10                  15

Glu Ala Val Arg Leu Phe Ile Glu Trp Leu Arg Asn Gly Lys Pro Ser
            20                  25                  30

Ser Gly Ala Pro Pro Pro Ser
        35
```

What is claimed is:

1. A compound comprising an exendin-4 agonist analog which comprises the amino acid sequence of SEQ ID NO:51 linked to a polylysine through the C-terminal amino acid residue.

2. A pharmaceutical composition comprising (A) a compound which comprises an exendin-4 agonist analog which comprises the amino acid sequence of SEQ ID NO:51 linked to a polylysine through the C-terminal amino acid residue; and (B) a pharmaceutically acceptable carrier.

3. A kit comprising the pharmaceutical composition of claim 2 and instructions for use.

4. A pharmaceutical composition comprising (A) a compound which comprises an exendin-4 which comprises the amino acid sequence of SEQ ID NO:2 or an exendin-4 agonist analog which comprises the amino acid sequence of SEQ ID NO:51 linked to a polylysine through (i) the C-terminal amino acid residue, (ii) an internal lysine amino acid at position 12 or 27, (iii) an internal aspartic acid amino acid, (iv) an internal glutamic acid amino acid, or (v) the N-terminal amino acid residue; and (B) a pharmaceutically acceptable carrier.

5. The pharmaceutical composition of claim 4, wherein the exendin-4 or the exendin-4 agonist analog is linked to the polylysine through the C-terminal amino acid residue.

6. The pharmaceutical composition of claim 4, wherein the exendin-4 or the exendin-4 agonist analog is linked to the polylysine through the internal lysine amino acid at position 12.

7. The pharmaceutical composition of claim 4, wherein the exendin-4 or the exendin-4 agonist analog is linked to the polylysine through the internal lysine amino acid at position 27.

8. The pharmaceutical composition of claim 4, wherein the exendin-4 or the exendin-4 agonist analog is linked to the polylysine through the internal aspartic acid amino acid.

9. The pharmaceutical composition of claim 4, wherein the exendin-4 or the exendin-4 agonist analog is linked to the polylysine through the internal glutamic acid amino acid.

10. The pharmaceutical composition of claim 4, wherein the exendin-4 or the exendin-4 agonist analog is linked to the polylysine through the N-terminal amino acid residue.

11. A pharmaceutical composition comprising (A) a compound which comprises exendin-4 which comprises the amino acid sequence of SEQ ID NO:2 or an exendin-4 agonist analog which comprises the amino acid sequence of SEQ ID NO:51 linked to a polyamino acid through the C-terminal amino acid residue; and (B) a pharmaceutically acceptable carrier.

12. The pharmaceutical composition of claim 11, wherein the polyamino acid is polylysine.

13. The pharmaceutical composition of claim 11, wherein the polyamino acid is polyglutamic acid.

14. The pharmaceutical composition of claim 11, wherein the polyamino acid is polyaspartic acid.

15. A pharmaceutical composition comprising (A) a compound which comprises exendin-4 which comprises the amino acid sequence of SEQ ID NO:2 or an exendin-4 agonist analog which comprises the amino acid sequence of SEQ ID NO:51 linked to a polyamino acid through (i) the C-terminal amino acid residue, (ii) the internal lysine amino acid at position 12 or 27, (iii) the internal aspartic acid amino acid, (iv) the internal glutamic acid amino acid, or (v) the N-terminal amino acid residue; and (B) a pharmaceutically acceptable carrier.

16. The pharmaceutical composition of claim 15, wherein the polyamino acid is polylysine.

17. The pharmaceutical composition of claim 15, wherein the polyamino acid is polyglutamic acid.

18. The pharmaceutical composition of claim 15, wherein the polyamino acid is polyaspartic acid.

19. The pharmaceutical composition of claim 15, wherein the exendin-4 or exendin-4 agonist analog is linked to the polyamino acid through the C-terminal amino acid residue.

20. The pharmaceutical composition of claim 15, wherein the a therapeutically effective amount is 30 µg/day to 5 mg/day.

* * * * *